US009905781B2

(12) United States Patent
Jeong et al.

(10) Patent No.: US 9,905,781 B2
(45) Date of Patent: Feb. 27, 2018

(54) CONDENSED CYCLIC COMPOUND AND ORGANIC LIGHT-EMITTING DEVICE INCLUDING THE SAME

(71) Applicant: Samsung Display Co., Ltd., Yongin-si, Gyeonggi-do (KR)

(72) Inventors: Hyein Jeong, Yongin-si (KR); Jungsub Lee, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 30 days.

(21) Appl. No.: 15/267,095

(22) Filed: Sep. 15, 2016

(65) Prior Publication Data

US 2017/0104166 A1 Apr. 13, 2017

(30) Foreign Application Priority Data

Oct. 8, 2015 (KR) ........................ 10-2015-0141690

(51) Int. Cl.
*H01L 51/00* (2006.01)
*C07D 471/04* (2006.01)
(Continued)

(52) U.S. Cl.
CPC ........ *H01L 51/0072* (2013.01); *C07D 471/04* (2013.01); *C09K 11/025* (2013.01);
(Continued)

(58) Field of Classification Search
None
See application file for complete search history.

(56) References Cited

U.S. PATENT DOCUMENTS 5,645,948 A 7/1997 Shi et al.
6,083,634 A 7/2000 Shi
(Continued)

FOREIGN PATENT DOCUMENTS

EP 0700917 A2 3/1996
JP 10-17860 A 1/1998
(Continued)

*Primary Examiner* — J. L. Yang
(74) *Attorney, Agent, or Firm* — Lewis Roca Rothgerber Christie LLP

(57) ABSTRACT

An organic light-emitting device includes: a first electrode; a second electrode facing the first electrode; and an organic layer between the first electrode and the second electrode, the organic layer including an emission layer; wherein the organic layer includes a condensed cyclic compound of Formula 1:

Formula 1

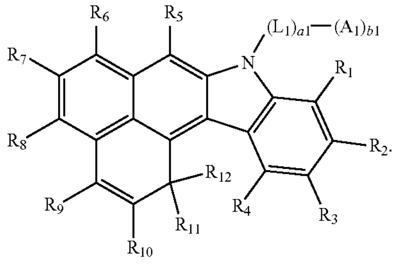

The organic light-emitting device including the condensed cyclic compound may exhibit low driving voltage, high efficiency, high luminance, and long lifespan characteristics.

20 Claims, 4 Drawing Sheets

(51) Int. Cl.

| | |
|---|---|
| ***C09K 11/02*** | (2006.01) |
| ***C09K 11/06*** | (2006.01) |
| *H01L 51/50* | (2006.01) |
| *H01L 51/52* | (2006.01) |

(52) U.S. Cl.
CPC .......... *C09K 11/06* (2013.01); *H01L 51/0052* (2013.01); *C09K 2211/1007* (2013.01); *C09K 2211/1029* (2013.01); *C09K 2211/185* (2013.01); *H01L 51/0081* (2013.01); *H01L 51/0085* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5206* (2013.01); *H01L 51/5221* (2013.01)

(56) References Cited

U.S. PATENT DOCUMENTS

| | | | | |
|---|---|---|---|---|
| 6,171,715 | B1 | 1/2001 | Sato et al. | |
| 2012/0097924 | A1* | 4/2012 | Kim .................... | C07D 209/56 257/40 |
| 2014/0361257 | A1 | 12/2014 | Park et al. | |
| 2015/0008394 | A1 | 1/2015 | Oh et al. | |
| 2016/0197289 | A1 | 7/2016 | Sado et al. | |

FOREIGN PATENT DOCUMENTS

| | | | |
|---|---|---|---|
| JP | 11-87067 | A | 3/1999 |
| JP | 11-345686 | A | 12/1999 |
| JP | 2014-123687 | A | 7/2014 |
| KR | 10-2010-0007143 | A | 1/2010 |
| KR | 10-2012-0030009 | A | 3/2012 |
| KR | 10-2012-0050557 | A | 5/2012 |
| WO | WO 2012/036482 | A1 | 3/2012 |

* cited by examiner

30

CONDENSED CYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2015-0141690, filed on Oct. 8, 2015, in the Korean Intellectual Property Office, the entire content of which is incorporated herein by reference.

BACKGROUND

1. Field

One or more aspects of example embodiments of the present disclosure relate to a condensed cyclic compound and an organic light-emitting device including the same.

2. Description of the Related Art

Organic light-emitting devices are self-emitting devices that have wide viewing angles, high contrast ratios, short response times, and excellent luminance, driving voltage, and response speed characteristics, and can produce full-color images, compared to organic light-emitting devices of the related art.

The organic light-emitting device of the present disclosure may include a first electrode disposed (e.g., positioned) on a substrate, and a hole transport region, an emission layer, an electron transport region, and a second electrode that are sequentially formed on the first electrode. Holes injected from the first electrode, for example, are transported to the emission layer through the hole transport region, and electrons injected from the second electrode, for example, are transported to the emission layer through the electron transport region. Carriers, such as the holes and electrons, can then recombine in the emission layer to generate excitons. When the excitons drop from an excited state to a ground state, light is emitted.

SUMMARY

One or more aspects of example embodiments of the present disclosure are directed toward a novel condensed cyclic compound and an organic light-emitting device including the same.

Additional aspects will be set forth in part in the description which follows and, in part, will be apparent from the description, or may be learned by practice of the presented embodiments.

According to one or more example embodiments, there is provided a condensed cyclic compound represented by Formula 1:

Formula 1

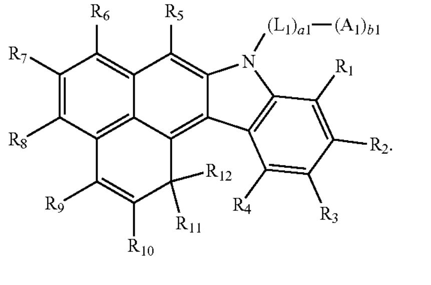

In Formula 1, $L_1$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 may be 0, 1, 2, or 3, and when a1 is 2 or more, 2 or more $L_1$s may be identical to or different from each other, $A_1$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, b1 may be 1, 2, or 3, and when b1 is 2 or more, 2 or more $A_1$s may be identical to or different from each other, $R_1$ to $R_{12}$ may be each independently selected from hydrogen, deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, and —$B(Q_6)(Q_7)$, at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$, where $Q_1$ to $Q_7$, $Q_{11}$ to $Q_{17}$, $Q_{21}$ to $Q_{27}$, and $Q_{31}$ to $Q_{37}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to one or more example embodiments, there is provided an organic light-emitting device including: a first electrode; a second electrode facing the first electrode; and an organic layer between the first electrode and the second electrode and including an emission layer; wherein the organic layer includes the condensed cyclic compound described above.

BRIEF DESCRIPTION OF THE DRAWINGS

These and/or other aspects will become apparent and more readily appreciated from the following description of the example embodiments, taken in conjunction with the accompanying drawings in which.

DETAILED DESCRIPTION

Figure 1:
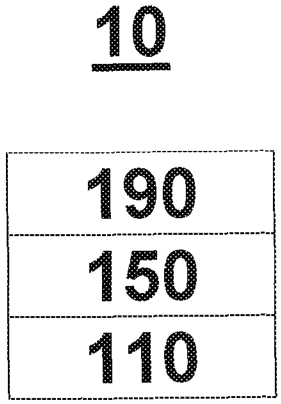
FIG. 1 is a diagram schematically illustrating an organic light-emitting device according to an example embodiment of the present disclosure.

Reference will now be made in more detail to example embodiments, examples of which are illustrated in the accompanying drawings, wherein like reference numerals refer to like elements throughout. In this regard, the present example embodiments may have different forms and should not be construed as being limited to the descriptions set forth herein. Accordingly, the example embodiments are merely described below, by referring to the drawings, to explain aspects of the present description. Expressions such as "at least one of," "one of," "at least one selected from," and "one selected from," when preceding a list of elements, modify the entire list of elements and do not modify the individual elements of the list. Further, the use of "may" when describing embodiments of the present invention refers to "one or more embodiments of the present invention."

In an example embodiment, a condensed cyclic compound may be represented by Formula 1:

Formula 1

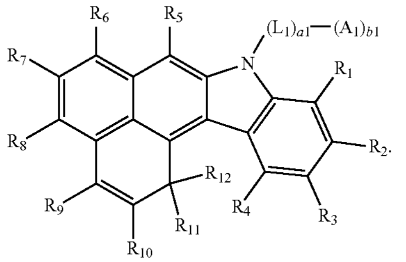

$L_1$ in Formula 1 may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In an example embodiment, $L_1$ in Formula 1 may be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —$Si(Q_{33})(Q_{34})(Q_{35})$, where $Q_{33}$ to $Q_{35}$ may be each independently selected from a $C_1$-$C_{10}$ alkyl group, a $C_1$-$C_{10}$ alkoxy group, a phenyl group, a biphenyl group, a terphenyl group, and a naphthyl group.

In another example embodiment, $L_1$ in Formula 1 may be selected from:

a phenylene group, a naphthylene group, a phenanthrenylene group, an anthracenylene group, a fluoranthenylene group, a triphenylenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a phenanthrolinylene group, a triazinylene group, a benzoimidazolylene group, an imidazopyridinylene group, and an imidazopyrimidinylene group; and a phenylene group, a naphthylene group, a phenanthrenylene group, an anthracenylene group, a fluoranthenylene group, a triphenylenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a phenanthrolinylene group, a triazinylene group, a benzoimidazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a phenanthrolinyl group, a triazinyl group, a benzoimidazolyl group, an imidazopyridinyl group, an imidazopyrimidinyl group, and —Si($Q_{33}$)($Q_{34}$)($Q_{35}$), where $Q_{33}$ to $Q_{35}$ may be each independently selected from a $C_1$-$C_{10}$ alkyl group, a $C_1$-$C_{10}$ alkoxy group, a phenyl group, a biphenyl group, a terphenyl group, and a naphthyl group.

In another example embodiment, $L_1$ in Formula 1 may be selected from groups represented by Formulae 3-1 to 3-46:

Formula 3-1

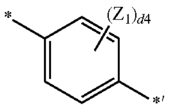

Formula 3-2

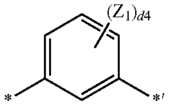

Formula 3-3

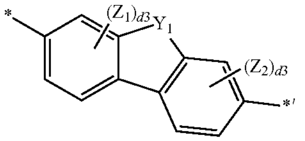

Formula 3-4

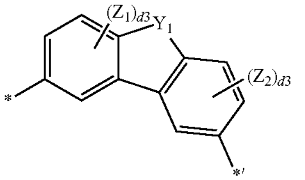

Formula 3-5

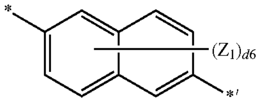

Formula 3-6

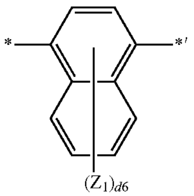

Formula 3-7

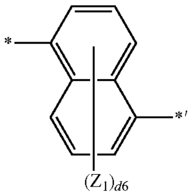

-continued

Formula 3-8

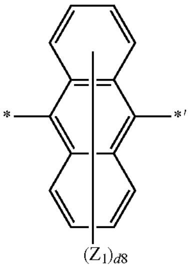

Formula 3-9

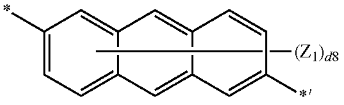

Formula 3-10

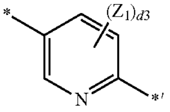

Formula 3-11

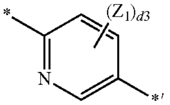

Formula 3-12

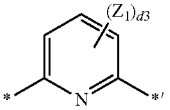

Formula 3-13

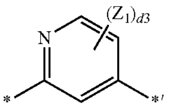

Formula 3-14

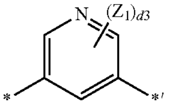

Formula 3-15

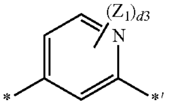

Formula 3-16

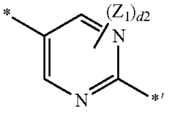

Formula 3-17

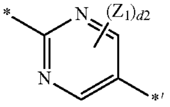

Formula 3-18

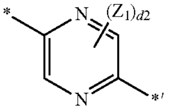

Formula 3-19

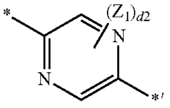

-continued
Formula 3-20
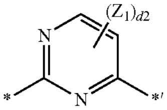
Formula 3-21
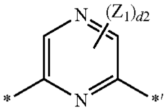
lp;1p
Formula 3-22
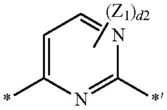
Formula 3-23
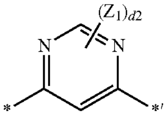
Formula 3-24
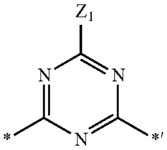
Formula 3-25
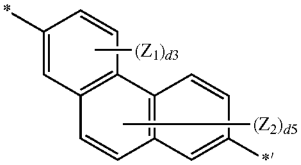
Formula 3-26
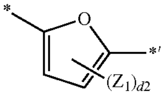
Formula 3-27
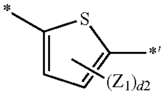
Formula 3-28
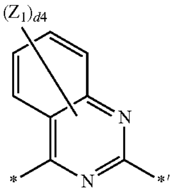
Formula 3-29
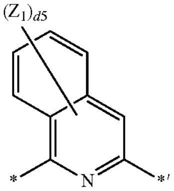
-continued
Formula 3-30
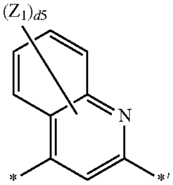
Formula 3-31
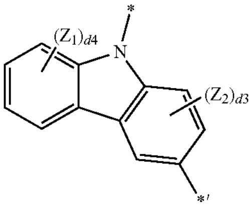
Formula 3-32
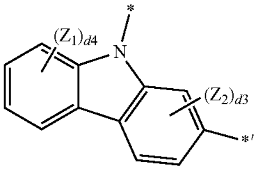
Formula 3-33
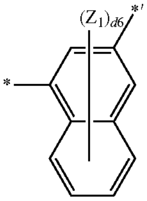
Formula 3-34
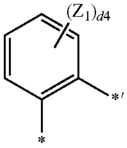
Formula 3-35
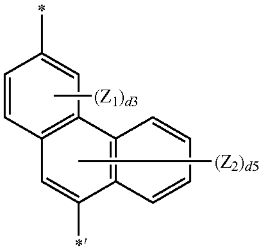
Formula 3-36
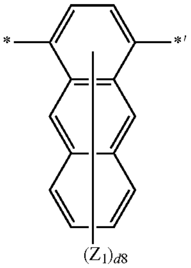

-continued

Formula 3-37

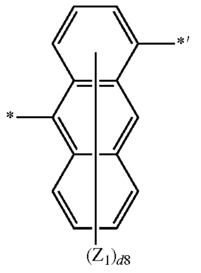

Formula 3-38

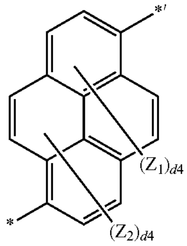

Formula 3-39

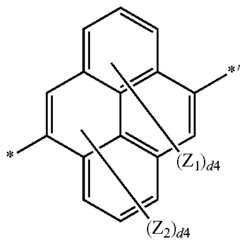

Formula 3-40

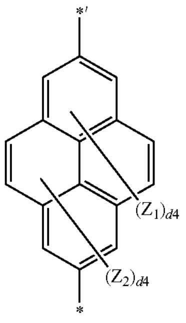

Formula 3-41

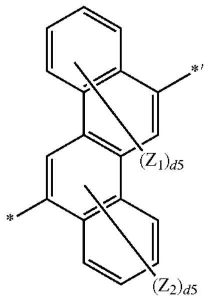

-continued

Formula 3-42

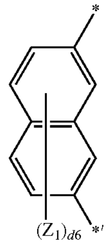

Formula 3-43

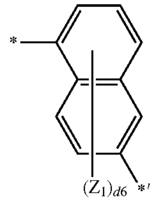

Formula 3-44

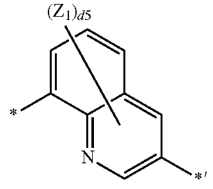

Formula 3-45

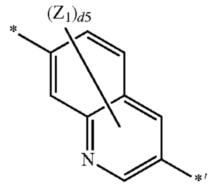

Formula 3-46

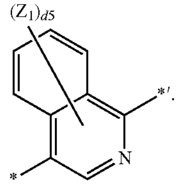

In Formulae 3-1 to 3-46, $Y_1$ may be selected from O, S, $C(Z_3)(Z_4)$, $N(Z_5)$, and $Si(Z_6)(Z_7)$, $Z_1$ to $Z_7$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a benzoimidazolyl group, a phenanthrolinyl group, and $—Si(Q_{33})(Q_{34})(Q_{35})$, where $Q_{33}$ to $Q_{35}$ may be each independently selected from a $C_1$-$C_{10}$ alkyl group, a $C_1$-$C_{10}$ alkoxy group, a phenyl group, a biphenyl group, a terphenyl group, and a naphthyl group, d2 may be 1 or 2, d3 may be an integer selected from 1 to 3, d4 may be an integer selected from 1 to 4, d5 may be an integer selected from 1 to 5, d6 may be an integer selected from 1 to 6, d8 may be an integer selected from 1 to 8, and

* and *' may each indicate a binding site to a neighboring atom.

In another example embodiment, $L_1$ in Formula 1 may be selected from groups represented by Formulae 4-1 to 4-45:

Formula 4-1

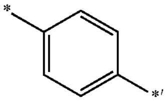

Formula 4-2

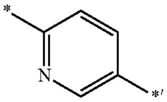

Formula 4-3

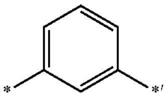

Formula 4-4

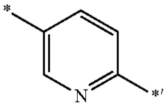

Formula 4-5

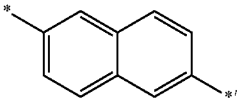

Formula 4-6

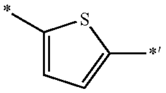

Formula 4-7

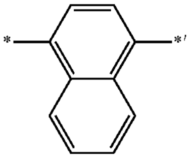

Formula 4-8

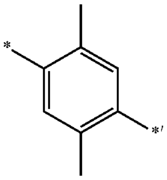

Formula 4-9

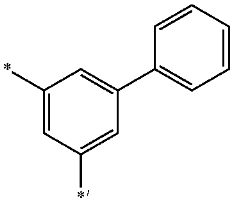

-continued

Formula 4-10

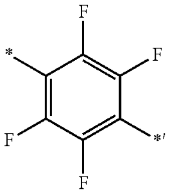

Formula 4-11

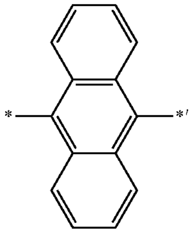

Formula 4-12

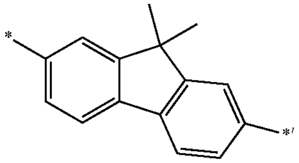

Formula 4-13

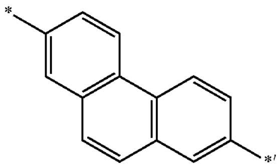

Formula 4-14

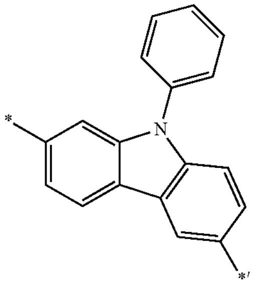

Formula 4-15

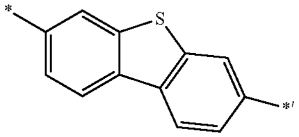

Formula 4-16

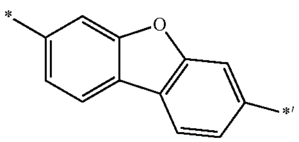

Formula 4-17

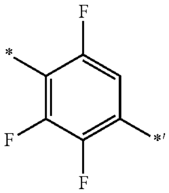

-continued
Formula 4-18
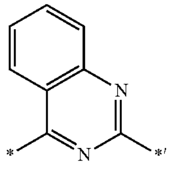
Formula 4-19
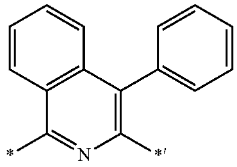
Formula 4-20
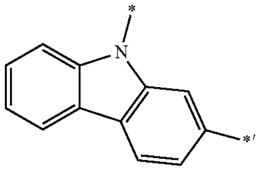
Formula 4-21
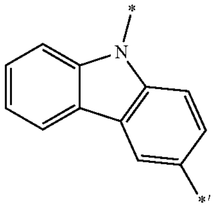
Formula 4-22
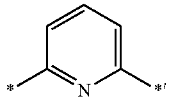
Formula 4-23
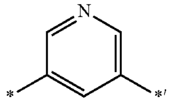
Formula 4-24
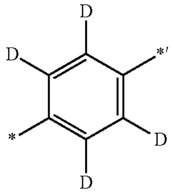
Formula 4-25
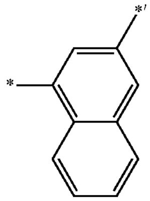
Formula 4-26
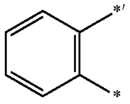
-continued
Formula 4-27
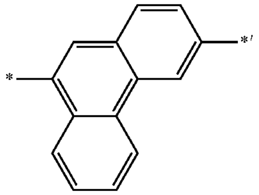
Formula 4-28
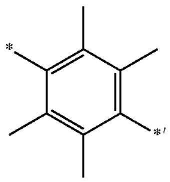
Formula 4-29
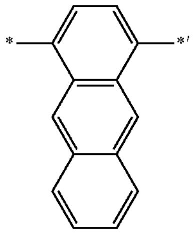
Formula 4-30
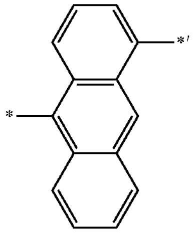
Formula 4-31
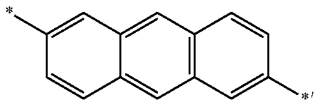
Formula 4-32
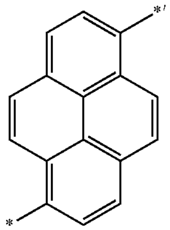
Formula 4-33
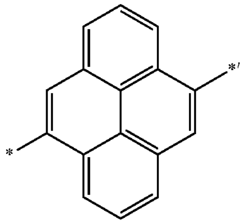

-continued

Formula 4-34

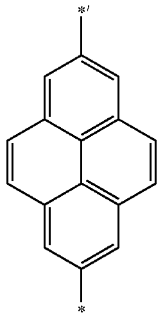

Formula 4-35

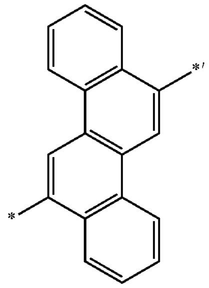

Formula 4-36

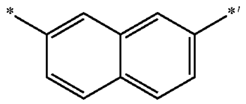

Formula 4-37

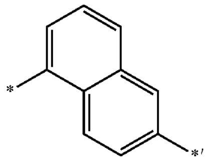

Formula 4-38

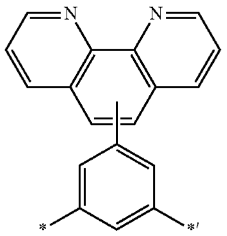

Formula 4-39

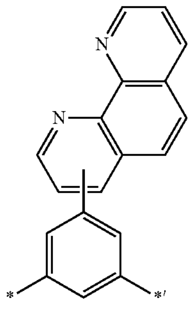

Formula 4-40

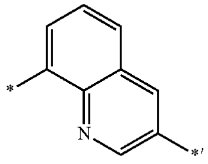

-continued

Formula 4-41

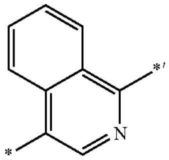

Formula 4-42

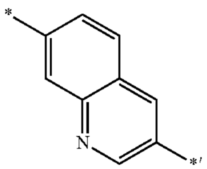

Formula 4-43

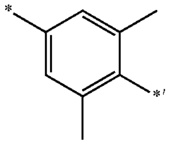

Formula 4-44

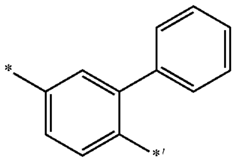

Formula 4-45

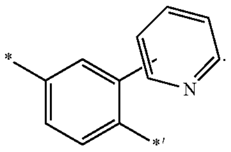

In Formulae 4-1 to 4-45, * and *' may each indicate a binding site to a neighboring atom, and "D" may refer to deuterium.

In Formula 1, a1 indicates the number of $L_1$, and may be 0, 1, 2, or 3. When a1 is 0, *-$(L_1)_{a1}$-*' in Formula 1 indicates a single bond. When a1 is 2 or more, 2 or more $L_1$s may be identical to or different from each other.

For example, in Formula 1, a1 may be 0, 1 or 2.

In an example embodiment, $A_1$ in Formula 1 may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In another example embodiment, $A_1$ in Formula 1 may be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group a dibenzocarbazolyl group, a thiadiazolyl group, an imidazopyridinyl group, an imidazopyrimidinyl group, and —$Si(Q_{33})(Q_{34})(Q_{35})$.

where $Q_{33}$ to $Q_{35}$ may be each independently selected from a $C_1$-$C_{10}$ alkyl group, a $C_1$-$C_{10}$ alkoxy group, a phenyl group, a biphenyl group, a terphenyl group and a naphthyl group.

In another example embodiment, $A_1$ in Formula 1 may be selected from:

an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an oxadiazolyl group, a triazinyl group, an imidazopyridinyl group, and an imidazopyrimidinyl group; and an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an oxadiazolyl group, a triazinyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an oxadiazolyl group, a triazinyl group, an imidazopyridinyl group, an imidazopyrimidinyl group, and —$Si(Q_{33})(Q_{34})(Q_{35})$, where $Q_{33}$ to $Q_{35}$ may be each independently selected from a $C_1$-$C_{10}$ alkyl group, a $C_1$-$C_{10}$ alkoxy group, a phenyl group, a biphenyl group, a terphenyl group, and a naphthyl group, but embodiments are not limited thereto.

In another example embodiment, $A_1$ in Formula 1 may be selected from:

a phenyl group, a biphenyl group, a terphenyl group, a naphthyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a phenanthrolinyl group, a triazinyl group, a benzoimidazolyl group, an imidazopyridinyl group, and an imidazopyrimidinyl group, and a phenyl group, a biphenyl group, a terphenyl group, a naphthyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a phenanthrolinyl group, a triazinyl group, a benzoimidazolyl group, an imidazopyridinyl group, and an imidazopyrimidinyl group, each substituted with at least one selected from deuterium. —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a phenanthrolinyl group, a triazinyl group, a benzoimidazolyl group, an imidazopyridinyl group, an imidazopyrimidinyl group, and —$Si(Q_{33})(Q_{34})(Q_{35})$, where $Q_{33}$ to $Q_{35}$ may be each independently selected from a $C_1$-$C_{10}$ alkyl group, a $C_1$-$C_{10}$ alkoxy group, a phenyl group, a biphenyl group, a terphenyl group, and a naphthyl group.

In another example embodiment, $A_1$ in Formula 1 may be selected from groups represented by Formulae 5-1 to 5-79:

Formula 5-1

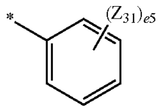

Formula 5-2

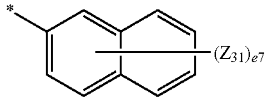

-continued

Formula 5-3

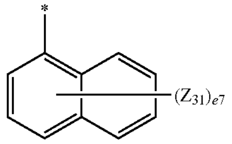

Formula 5-4

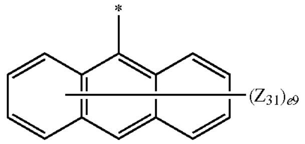

Formula 5-5

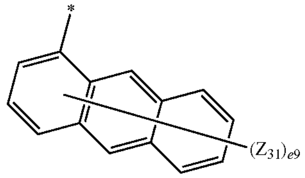

Formula 5-6

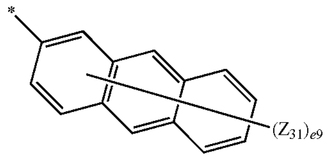

Formula 5-7

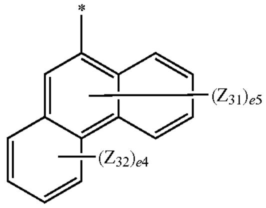

Formula 5-8

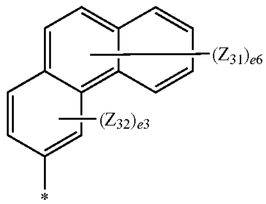

Formula 5-9

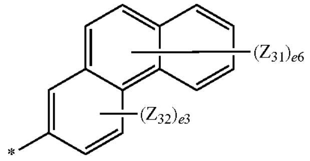

Formula 5-10

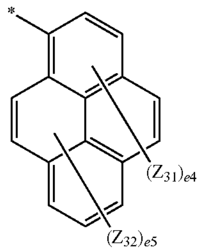

-continued
Formula 5-11
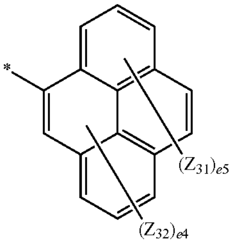
Formula 5-12
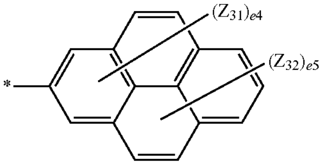
Formula 5-13
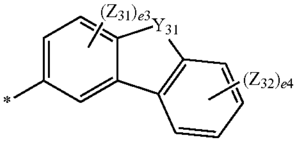
Formula 5-14
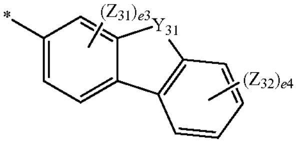
Formula 5-15
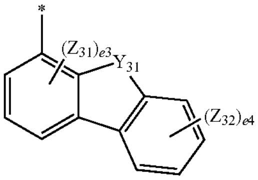
Formula 5-16
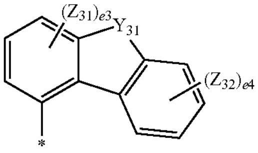
Formula 5-17
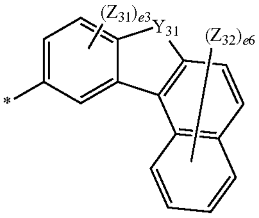
Formula 5-18
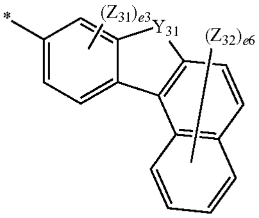
-continued
Formula 5-19
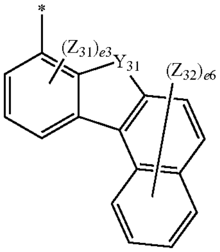
Formula 5-20
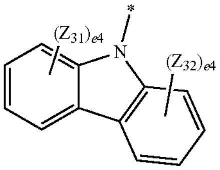
Formula 5-21
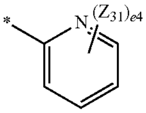
Formula 5-22
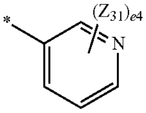
Formula 5-23
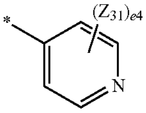
Formula 5-24
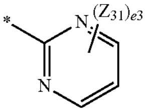
Formula 5-25
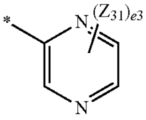
Formula 5-26
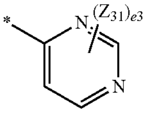
Formula 5-27
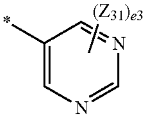
Formula 5-28
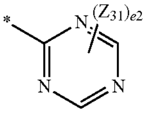
Formula 5-29
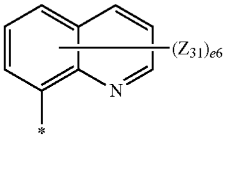

-continued
Formula 5-30
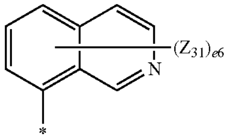
Formula 5-31
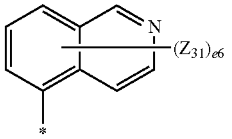
Formula 5-32
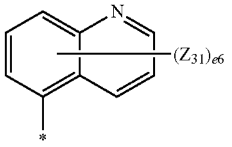
Formula 5-33
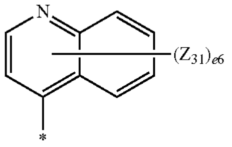
Formula 5-34
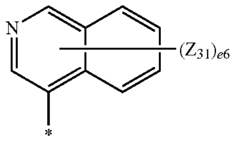
Formula 5-35
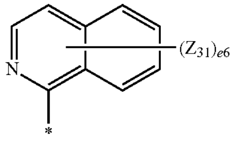
Formula 5-36
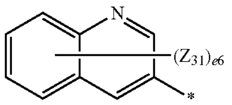
Formula 5-37
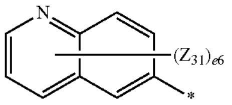
Formula 5-38
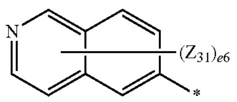
Formula 5-39
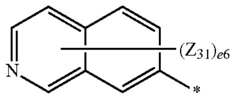
Formula 5-40
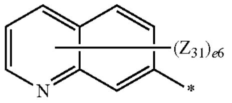
Formula 5-41
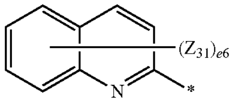
-continued
Formula 5-42
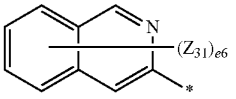
Formula 5-43
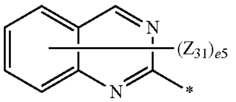
Formula 5-44
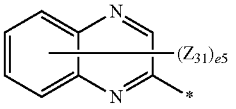
Formula 5-45
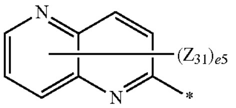
Formula 5-46
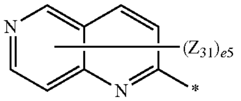
Formula 5-47
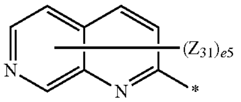
Formula 5-48
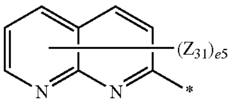
Formula 5-49
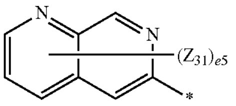
Formula 5-50
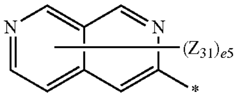
Formula 5-51
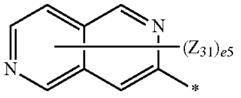
Formula 5-52
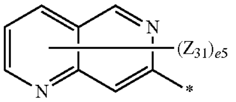
Formula 5-53
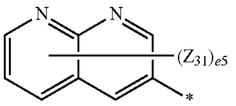
Formula 5-54
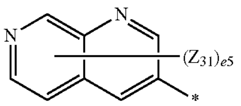
Formula 5-55
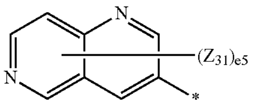

-continued
Formula 5-56
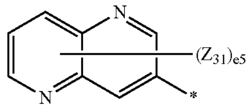
Formula 5-57
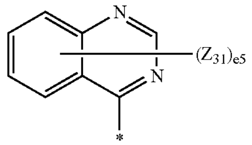
Formula 5-58
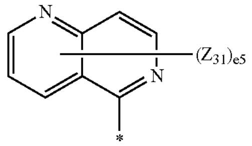
Formula 5-59
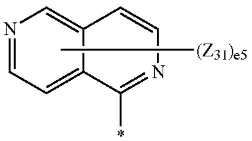
Formula 5-60
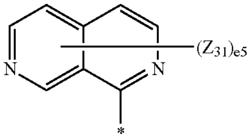
Formula 5-61
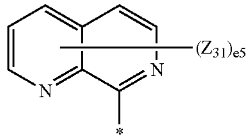
Formula 5-62
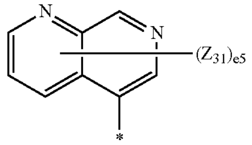
Formula 5-63
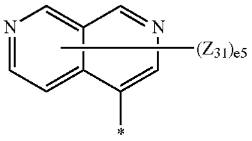
Formula 5-64
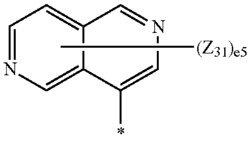
Formula 5-65
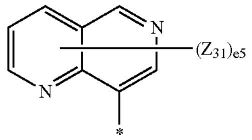
-continued
Formula 5-66
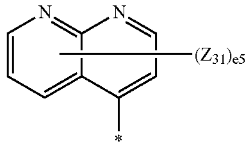
Formula 5-67
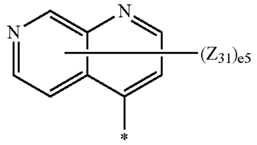
Formula 5-68
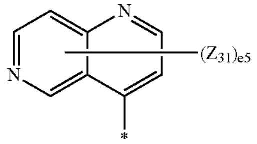
Formula 5-69
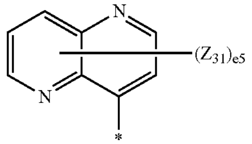
Formula 5-70
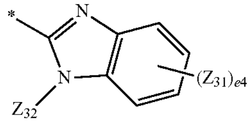
Formula 5-71
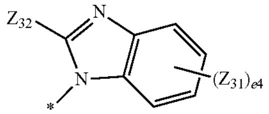
Formula 5-72
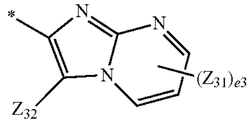
Formula 5-73
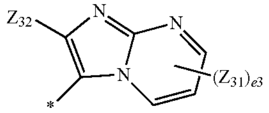
Formula 5-74
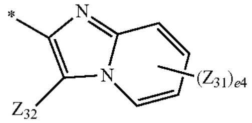
Formula 5-75
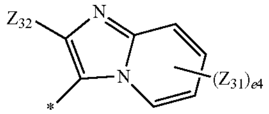
Formula 5-76
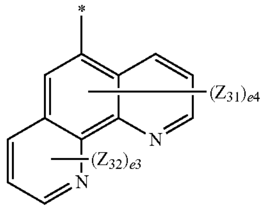

-continued

Formula 5-77

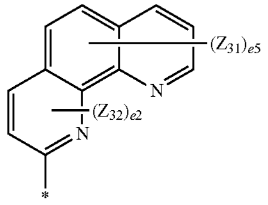

Formula 5-78

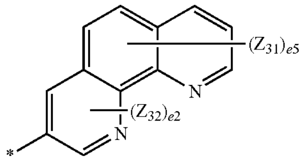

Formula 5-79

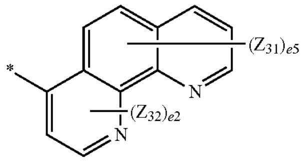

In Formulae 5-1 to 5-79, $Y_{31}$ may be selected from O, S, $C(Z_{33})(Z_{34})$, $N(Z_{35})$, and $Si(Z_{36})(Z_{37})$, $Z_{31}$ to $Z_{37}$ may be each independently selected from hydrogen, deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a benzoimidazolyl group, a phenanthrolinyl group, a triazinyl group, and $—Si(Q_{33})(Q_{34})(Q_{35})$, where $Q_{33}$ to $Q_{35}$ may be each independently selected from a $C_1$-$C_{10}$ alkyl group, a $C_1$-$C_{10}$ alkoxy group, a phenyl group, a biphenyl group, a terphenyl group, and a naphthyl group, e2 may by 1 or 2, e3 may be an integer selected from 1 to 3, e4 may be an integer selected from 1 to 4, e5 may be an integer selected from 1 to 5, e6 may be an integer selected from 1 to 6, e7 may be an integer selected from 1 to 7, e9 may be an integer selected from 1 to 9, and

* may indicate a binding site to a neighboring atom.

In another example embodiment, $A_1$ in Formula 1 may be selected from the groups represented by Formulae 5-21 to 5-79 above.

In another example embodiment, $A_1$ in Formula 1 may be selected from groups represented by Formulae 6-1 to 6-43 and groups represented by Formula 10-1 to 10-121, but embodiments are not limited thereto:

Formula 6-1

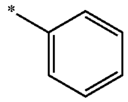

Formula 6-2

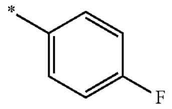

Formula 6-3

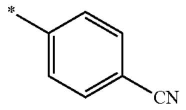

Formula 6-4

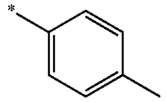

Formula 6-5

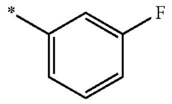

Formula 6-6

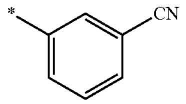

Formula 6-7

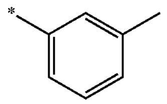

Formula 6-8

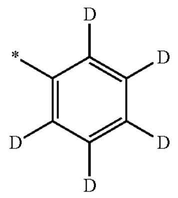

Formula 6-9

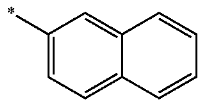

Formula 6-10

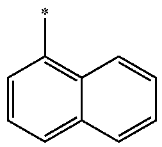

Formula 6-11

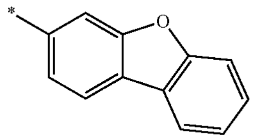

Formula 6-12

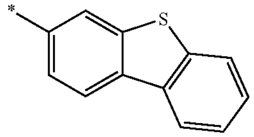

-continued
Formula 6-13
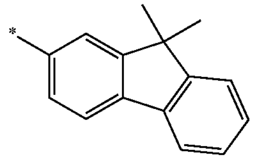
Formula 6-14
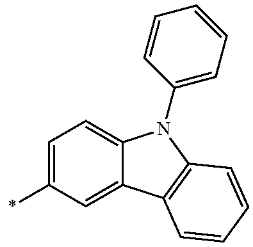
Formula 6-15
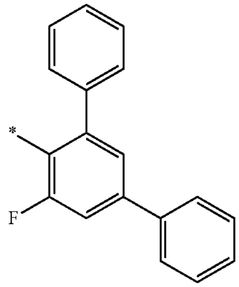
Formula 6-16
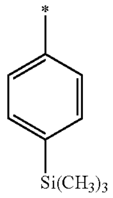
Formula 6-17
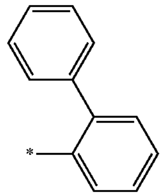
Formula 6-18
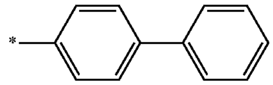
Formula 6-19
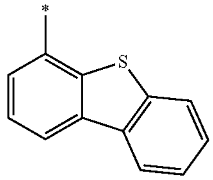
Formula 6-20
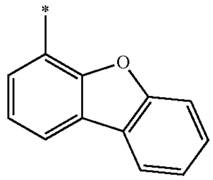
-continued
Formula 6-21
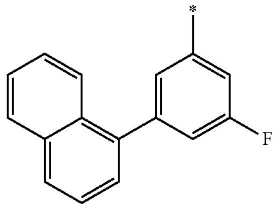
Formula 6-22
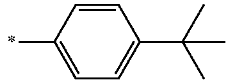
Formula 6-23
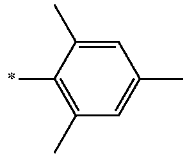
Formula 6-24
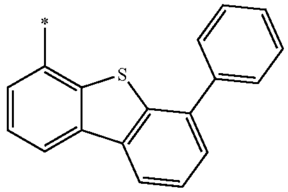
Formula 6-25
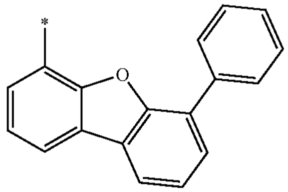
Formula 6-26
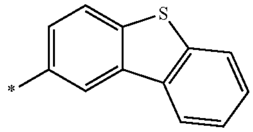
Formula 6-27
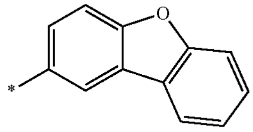
Formula 6-28
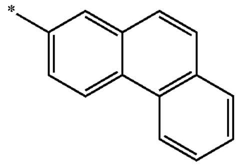
Formula 6-29
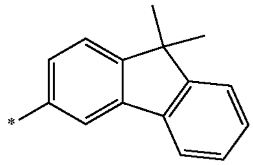

-continued
Formula 6-30
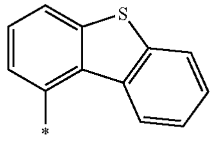
Formula 6-31
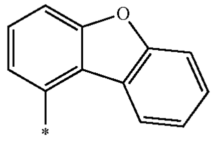
Formula 6-32
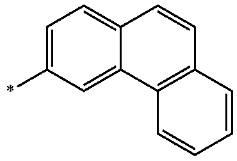
Formula 6-33
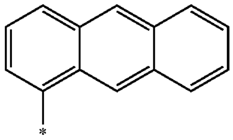
Formula 6-34
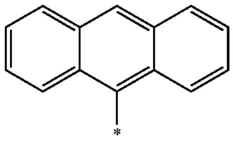
Formula 6-35
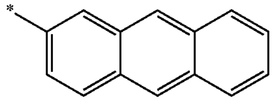
Formula 6-36
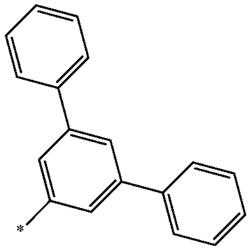
Formula 6-37
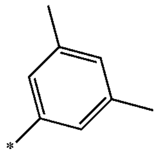
Formula 6-38
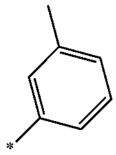
Formula 6-39
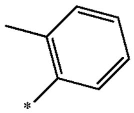
-continued
Formula 6-40
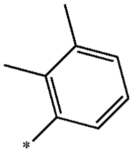
Formula 6-41
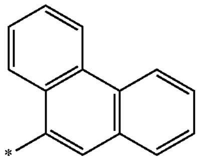
Formula 6-42
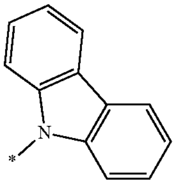
Formula 6-43
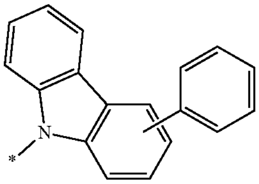
Formula 10-1
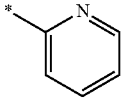
Formula 10-2
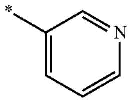
Formula 10-3
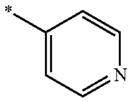
Formula 10-4
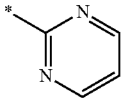
Formula 10-5
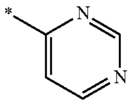
Formula 10-6
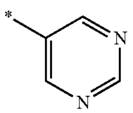
Formula 10-7
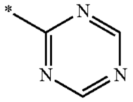

-continued
Formula 10-8
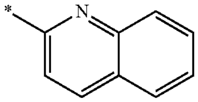
Formula 10-9
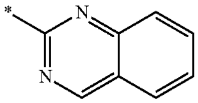
Formula 10-10
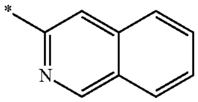
Formula 10-11
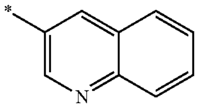
Formula 10-12
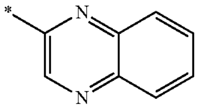
Formula 10-13
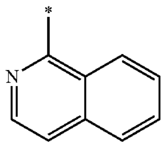
Formula 10-14
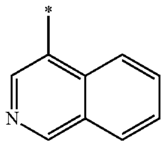
Formula 10-15
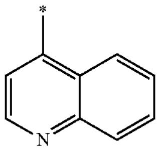
Formula 10-16
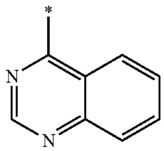
Formula 10-17
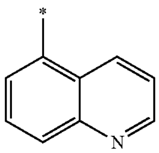
Formula 10-18
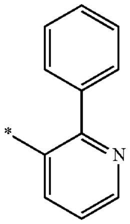
-continued
Formula 10-19
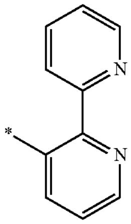
Formula 10-20
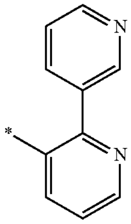
Formula 10-21
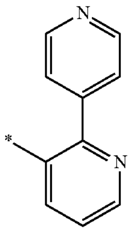
Formula 10-22
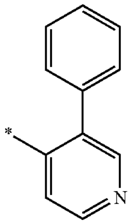
Formula 10-23
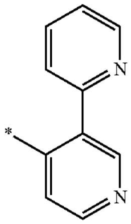
Formula 10-24
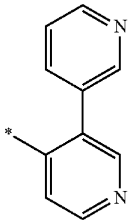
Formula 10-25
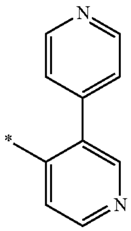

-continued
Formula 10-26
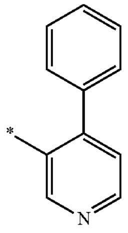
Formula 10-27
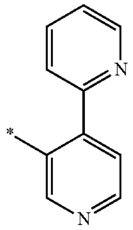
Formula 10-28
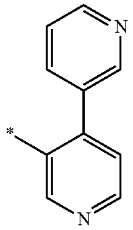
Formula 10-29
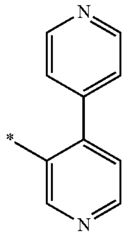
Formula 10-30
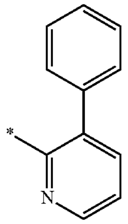
Formula 10-31
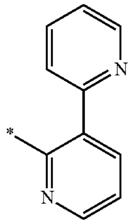
-continued
Formula 10-32
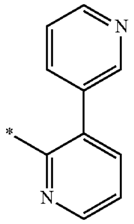
Formula 10-33
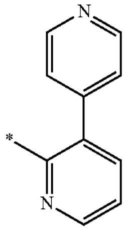
Formula 10-34
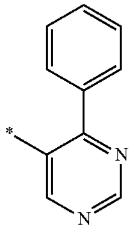
Formula 10-35
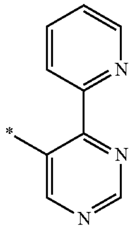
Formula 10-36
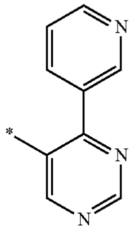
Formula 10-37
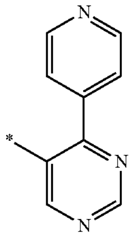

-continued
Formula 10-38
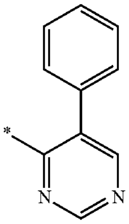
Formula 10-39
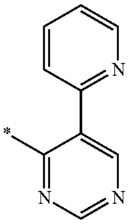
Formula 10-40
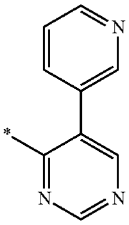
Formula 10-41
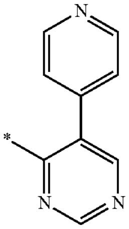
Formula 10-42
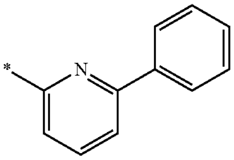
Formula 10-43
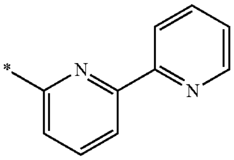
Formula 10-44
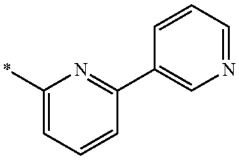
Formula 10-45
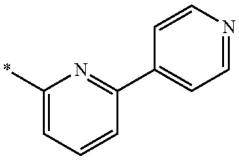
-continued
Formula 10-46
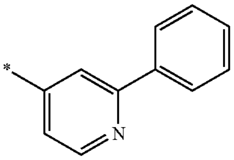
Formula 10-47
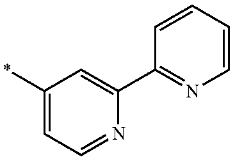
Formula 10-48
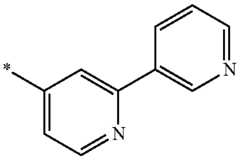
Formula 10-49
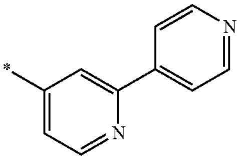
Formula 10-50
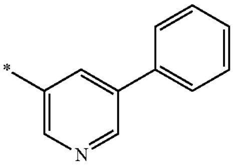
Formula 10-51
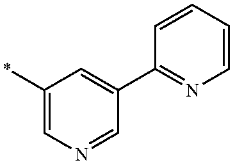
Formula 10-52
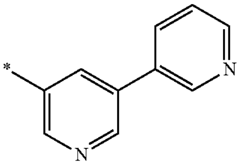
Formula 10-53
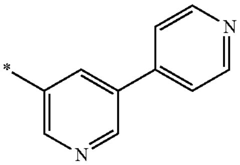
Formula 10-54
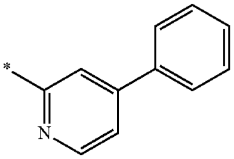

-continued
Formula 10-55
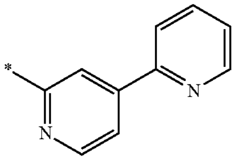
Formula 10-56
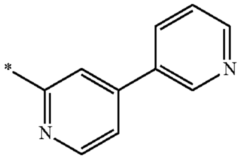
Formula 10-57
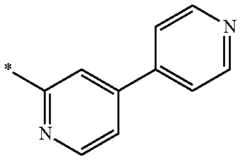
Formula 10-58
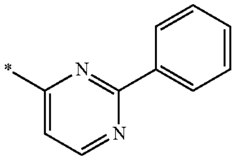
Formula 10-59
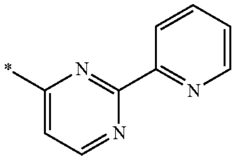
Formula 10-60
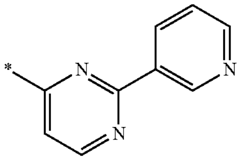
Formula 10-61
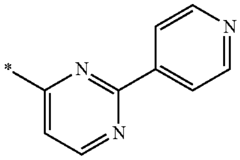
Formula 10-62
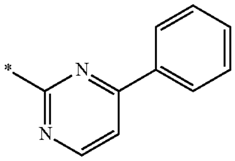
Formula 10-63
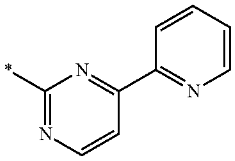
-continued
Formula 10-64
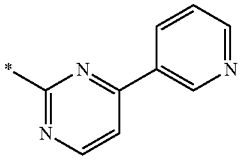
Formula 10-65
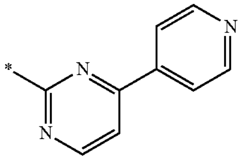
Formula 10-66
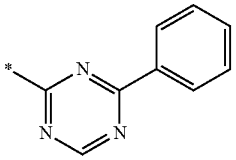
Formula 10-67
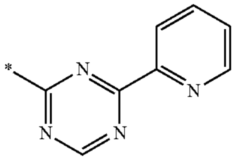
Formula 10-68
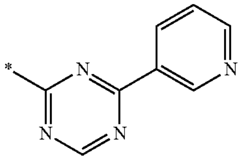
Formula 10-69
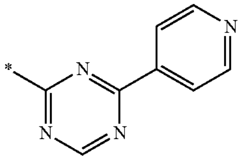
Formula 10-70
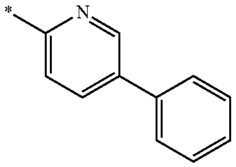
Formula 10-71
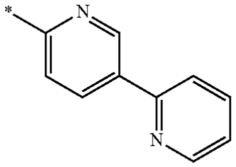
Formula 10-72
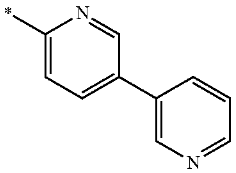

-continued
Formula 10-73
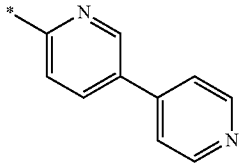
Formula 10-74
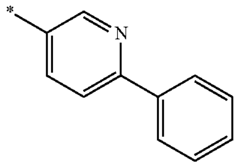
Formula 10-75
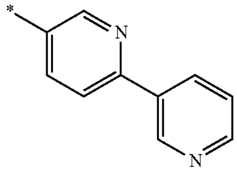
Formula 10-76
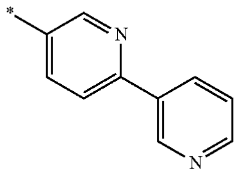
Formula 10-77
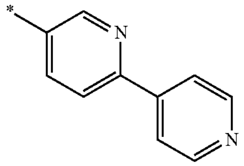
Formula 10-78
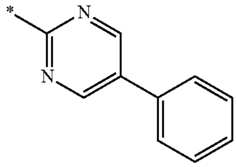
Formula 10-79
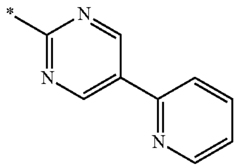
Formula 10-80
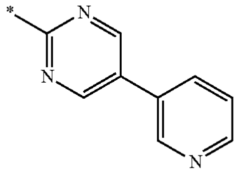
-continued
Formula 10-81
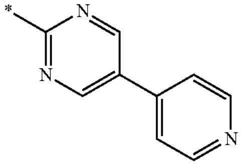
Formula 10-82
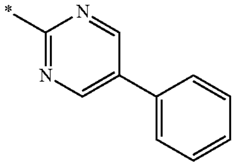
Formula 10-83
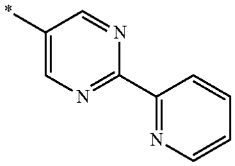
Formula 10-84
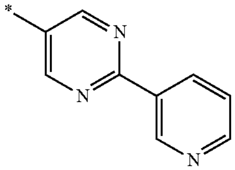
Formula 10-85
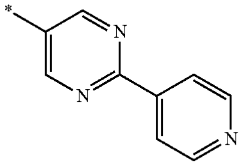
Formula 10-86
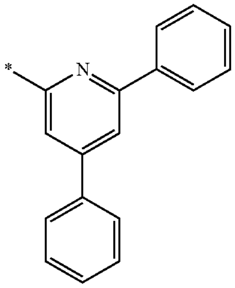
Formula 10-87
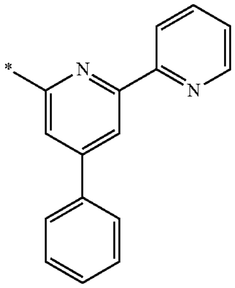

-continued
Formula 10-88
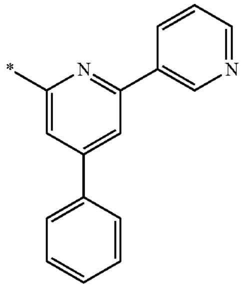
Formula 10-89
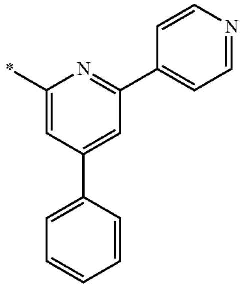
Formula 10-90
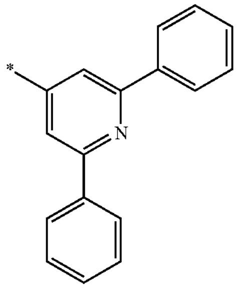
Formula 10-91
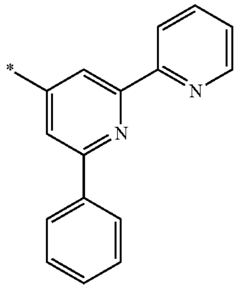
Formula 10-92
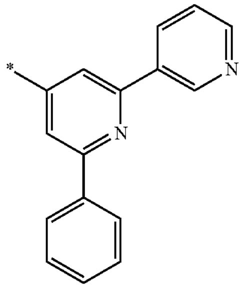
-continued
Formula 10-93
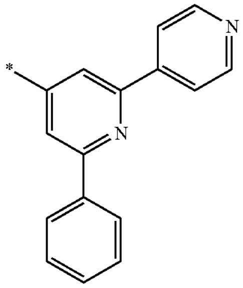
Formula 10-94
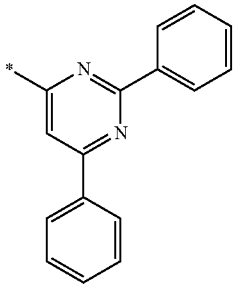
Formula 10-95
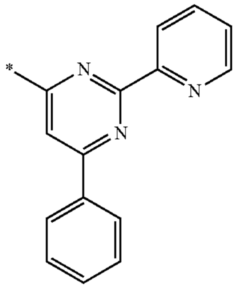
Formula 10-96
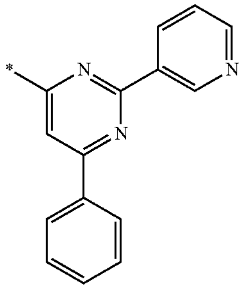
Formula 10-97
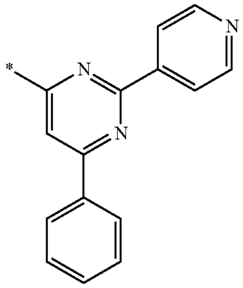

-continued
Formula 10-98
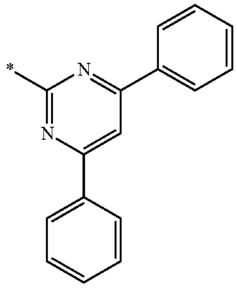
Formula 10-99
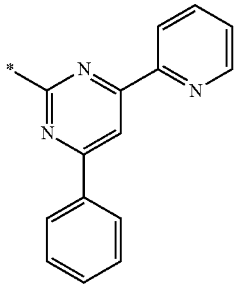
Formula 10-100
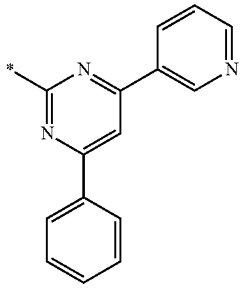
Formula 10-101
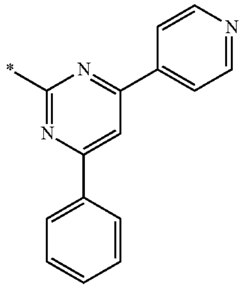
Formula 10-102
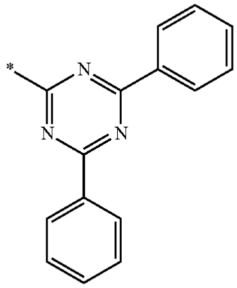
-continued
Formula 10-103
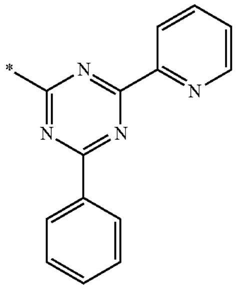
Formula 10-104
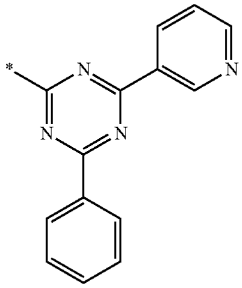
Formula 10-105
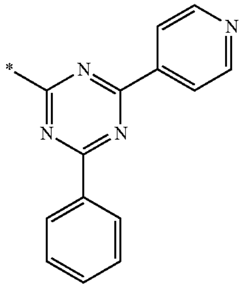
Formula 10-106
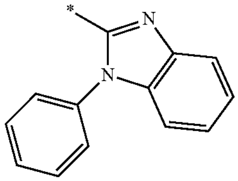
Formula 10-107
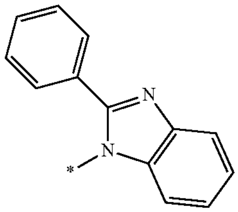
Formula 10-108
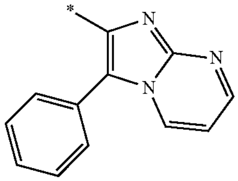

-continued

Formula 10-109

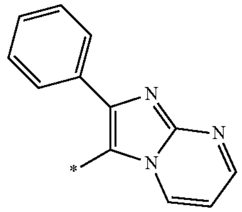

Formula 10-110

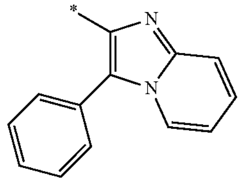

Formula 10-111

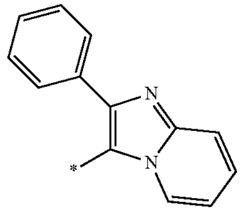

Formula 10-112

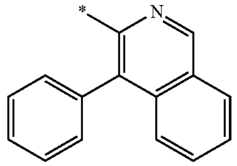

Formula 10-113

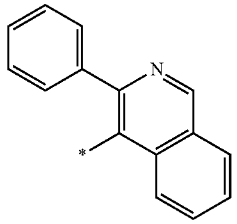

Formula 10-114

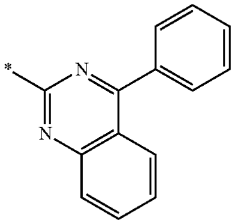

Formula 10-115

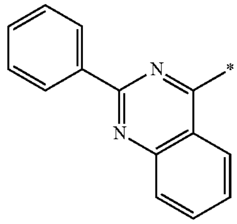

-continued

Formula 10-116

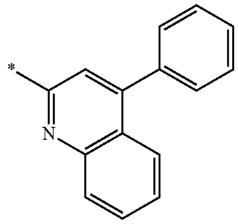

Formula 10-117

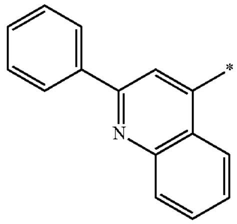

Formula 10-118

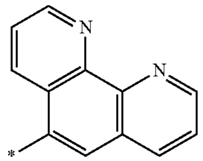

Formula 10-119

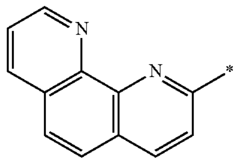

Formula 10-120

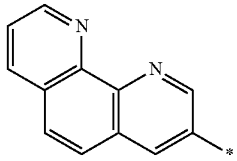

Formula 10-121

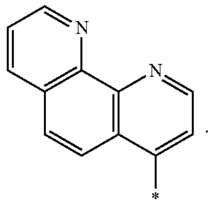

In Formulae 6-1 to 6-43 and 10-1 to 10-121, * may indicate a binding site to a neighboring atom, and "D" may refer to deuterium.

In Formula 1, b1 indicates the number of $A_1$, and may be 1, 2, or 3. When b1 is 2 or more, 2 or more $A_1$s may be identical to or different from each other.

For example, b1 in Formula 1 may be 1 or 2.

In an example embodiment, $R_1$ to $R_{12}$ in Formula 1 may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$), wherein $Q_1$ to $Q_7$ are as defined herein.

In another example embodiment, $R_1$ to $R_{12}$ in Formula 1 may be each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a di benzothiophenyl group, an imidazopyridinyl group, an imidazopyrimidinyl group, and —Si($Q_{33}$)($Q_{34}$)($Q_{35}$); and —Si($Q_3$)($Q_4$)($Q_5$), where $Q_3$ to $Q_5$ and $Q_{33}$ to $Q_{35}$ may be each independently selected from a $C_1$-$C_{10}$ alkyl group, a $C_1$-$C_{10}$ alkoxy group, a phenyl group, a biphenyl group, a terphenyl group, and a naphthyl group.

In another example embodiment, $R_1$ to $R_{12}$ in Formula 1 may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, and —Si($Q_3$)($Q_4$)($Q_5$), where $Q_3$ to $Q_5$ may be each independently selected from a $C_1$-$C_{10}$ alkyl group, a $C_1$-$C_{10}$ alkoxy group, a phenyl group, a biphenyl group, a terphenyl group, and a naphthyl group.

In an example embodiment, $R_1$ to $R_{12}$ in Formula 1 may each be hydrogen.

In another example embodiment, the above-described condensed cyclic compound may be one of Compounds 1 to 56, but embodiments are not limited thereto:

1

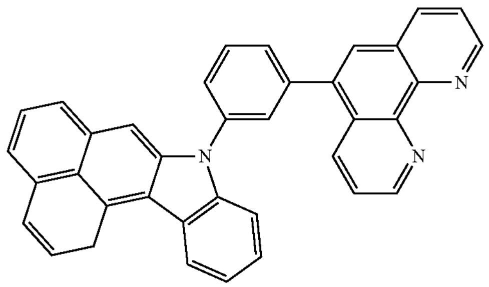 [SMILES: C1=Cc2cccc3cc4c(c(c23)C1)c1ccccc1n4-c1cccc(-c2cc3cccnc3c3ncccc23)c1]

2

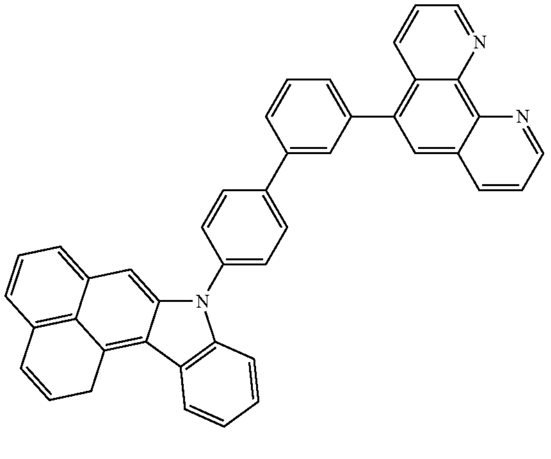

3
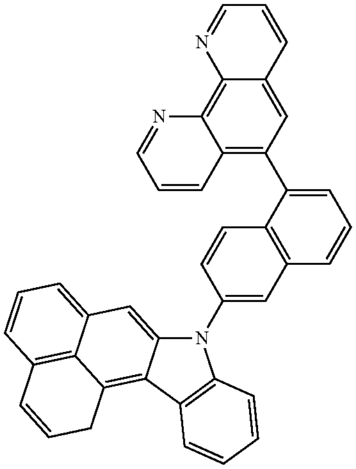 [SMILES: C1=Cc2cccc3cc4c(c(c23)C1)c1ccccc1n4-c1ccc2c(-c3cc4cccnc4c4ncccc34)cccc2c1]
4
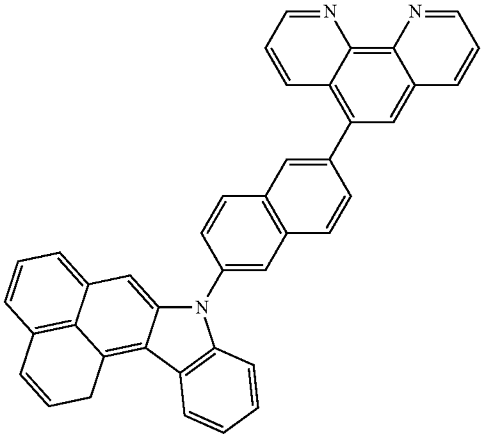
5
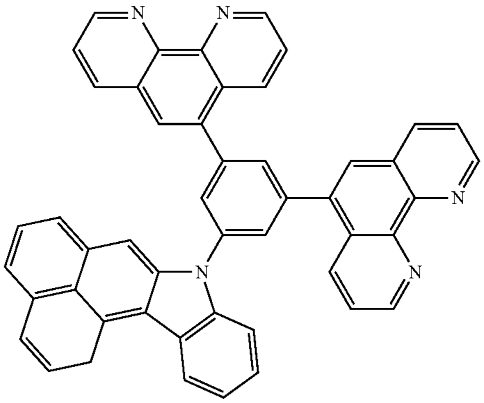 [SMILES: C1=Cc2cccc3cc4c(c(c23)C1)c1ccccc1n4-c1cc(-c2cc3cccnc3c3ncccc23)cc(-c2cc3cccnc3c3ncccc23)c1]
6
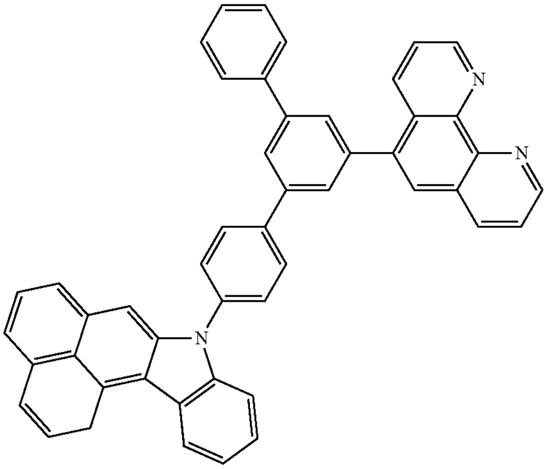
7
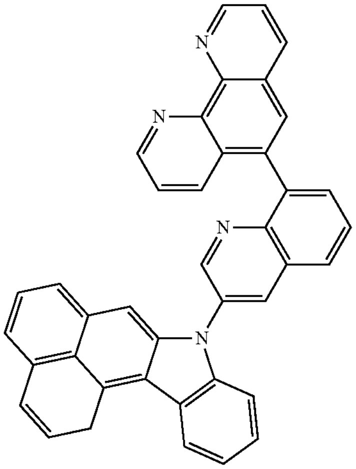
8
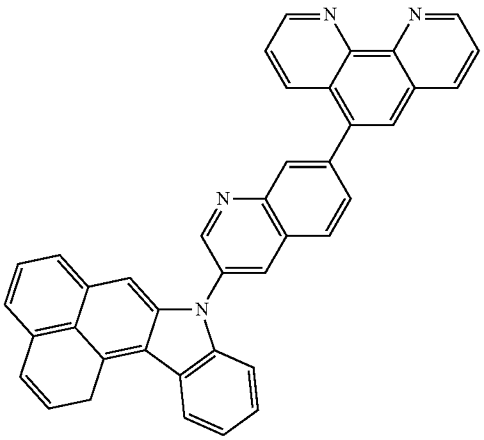

-continued
9
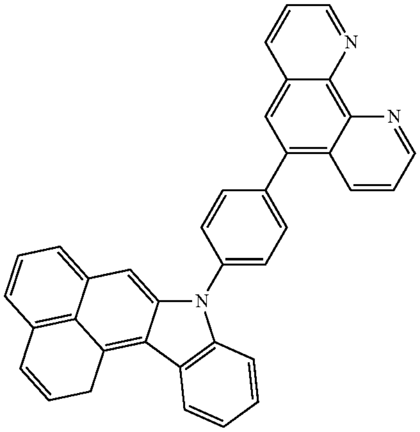 [SMILES: C1=Cc2cccc3cc4c(c(c23)C1)c1ccccc1n4-c1ccc(-c2cc3cccnc3c3ncccc23)cc1]
10
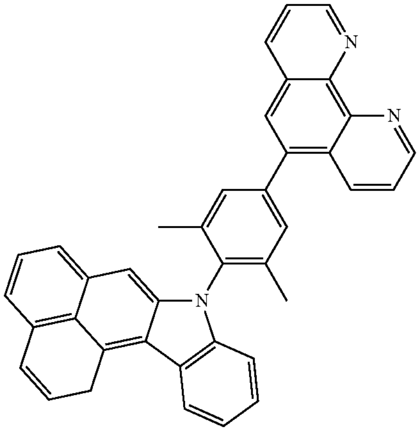
11
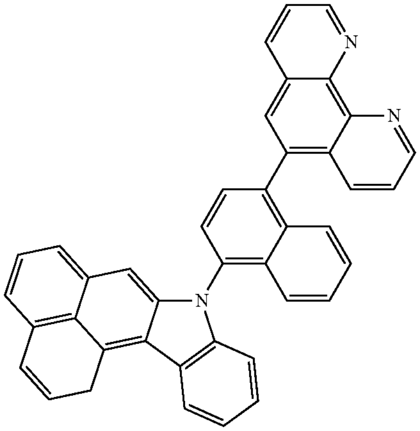
-continued
12
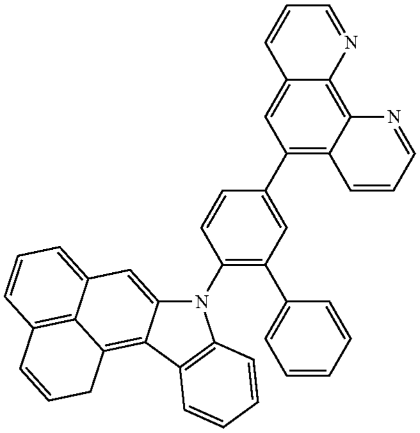
13
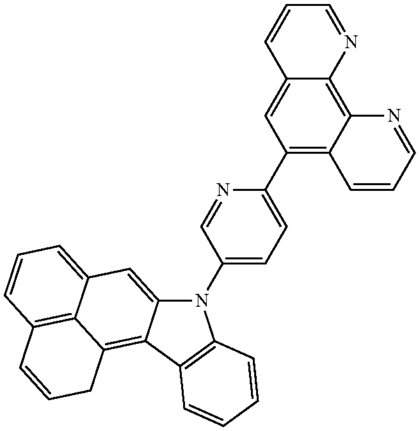
14
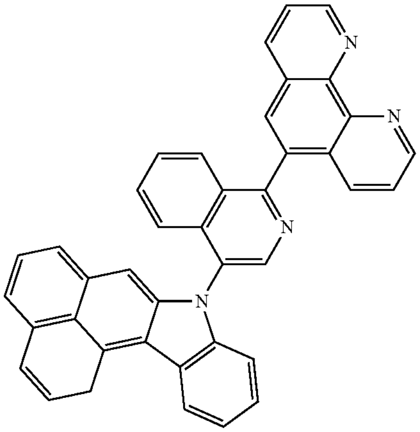

-continued
15
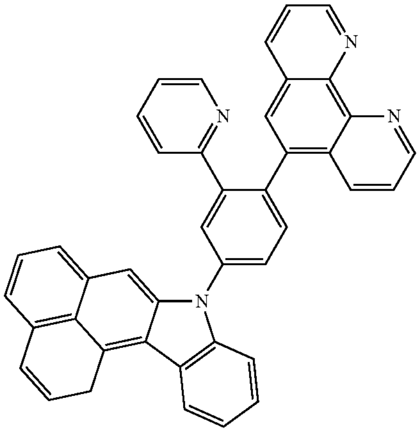
16
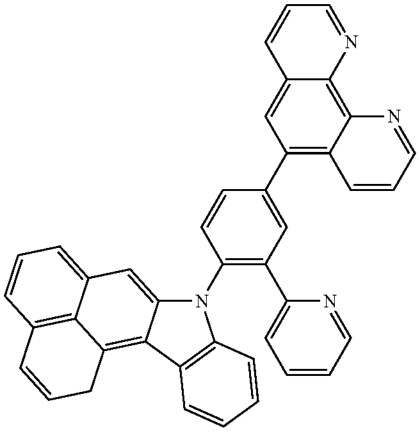
17
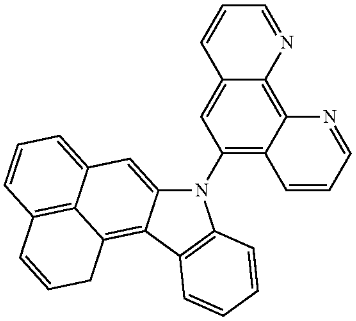
18
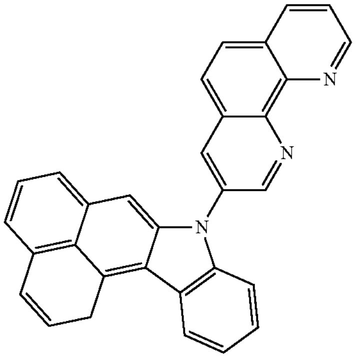
-continued
19
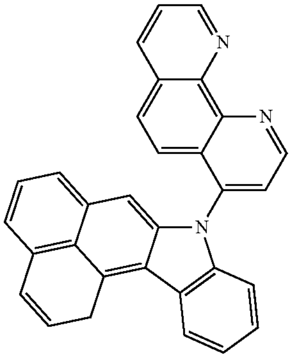
20
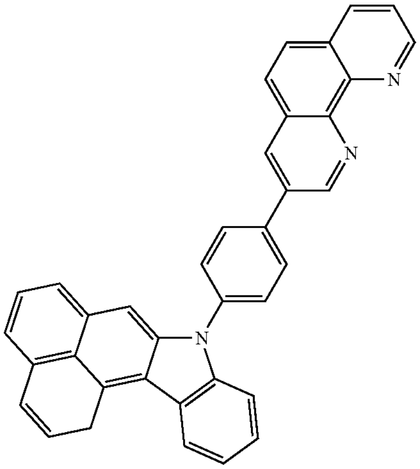
21
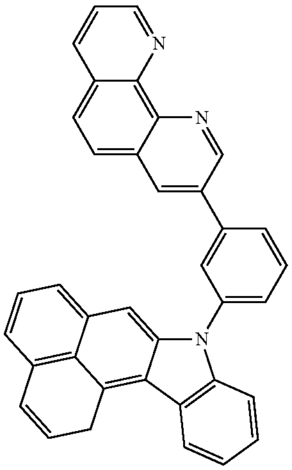

-continued
22
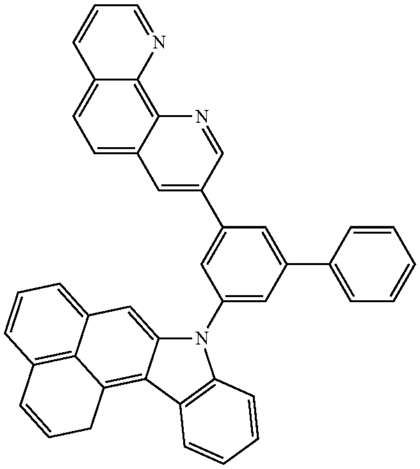
23
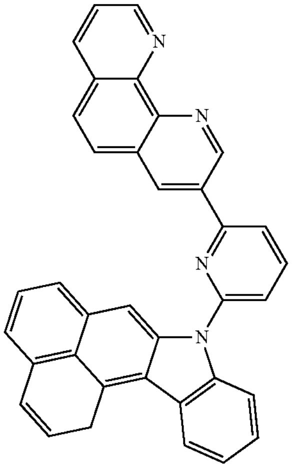
24
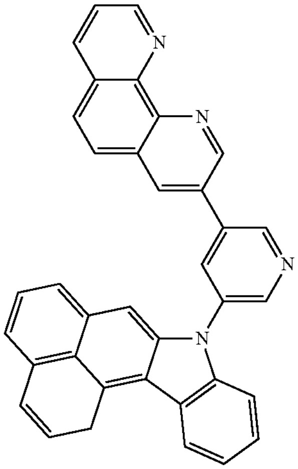
-continued
25
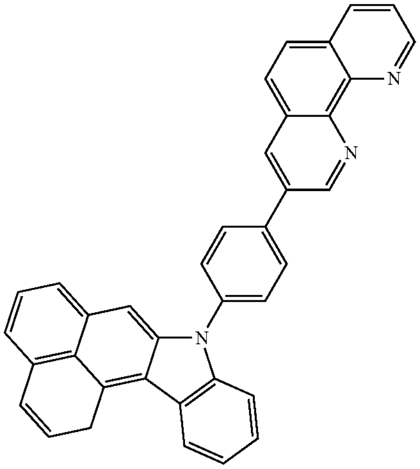
26
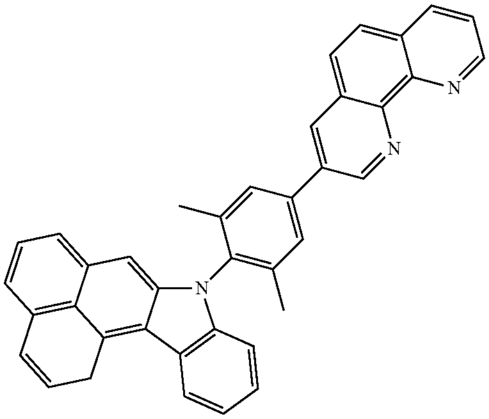
27
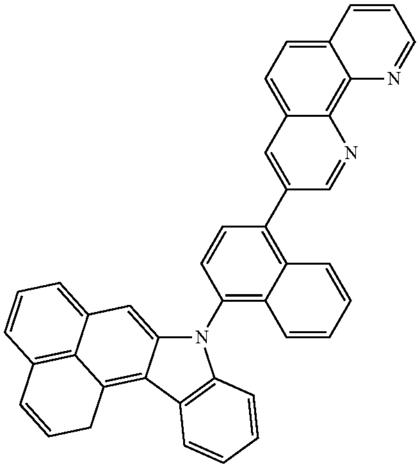

-continued
28
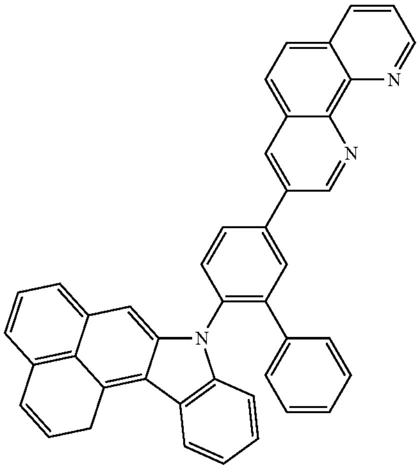
29
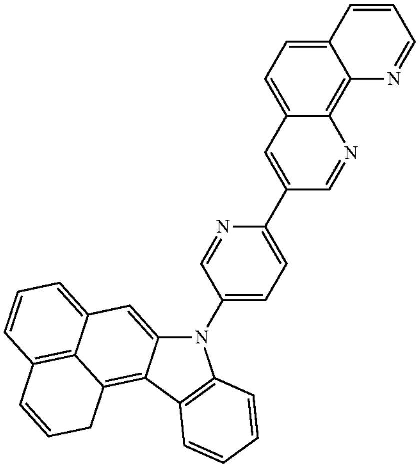
30
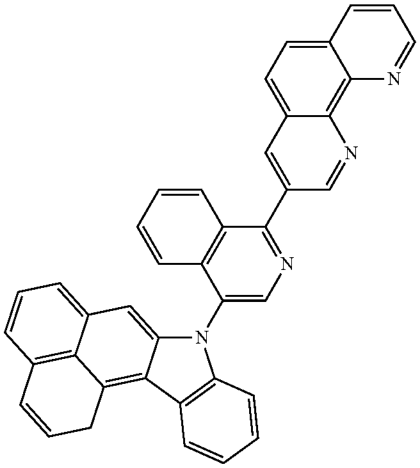
-continued
31
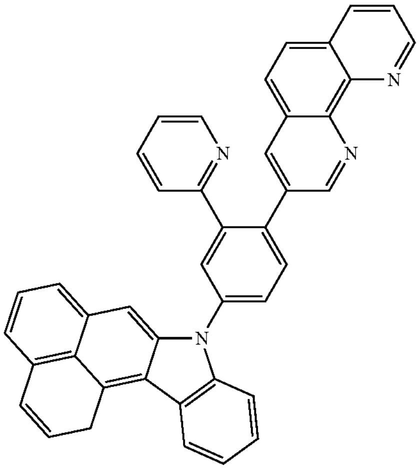
32
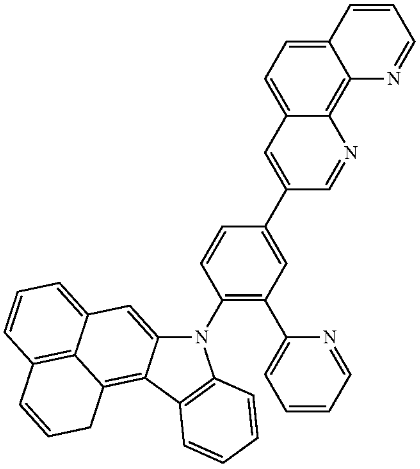
33
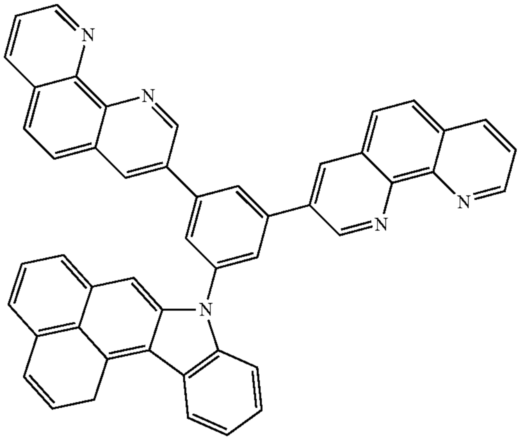

-continued
34
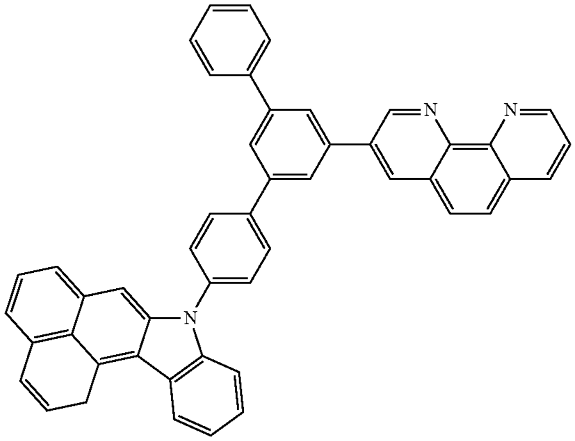
35
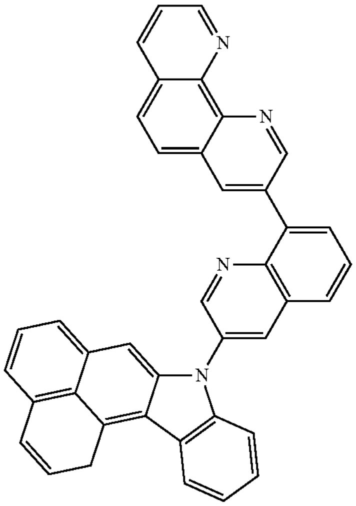
36
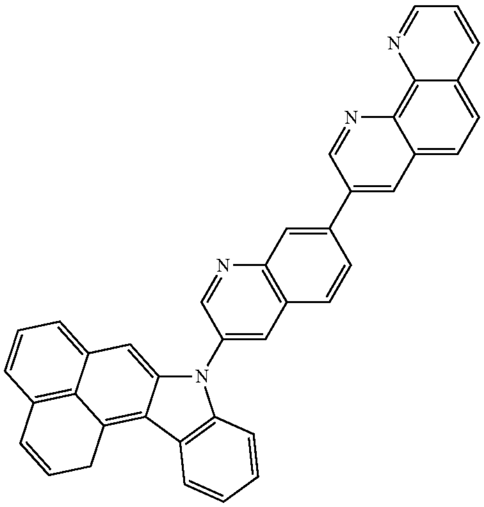
-continued
37
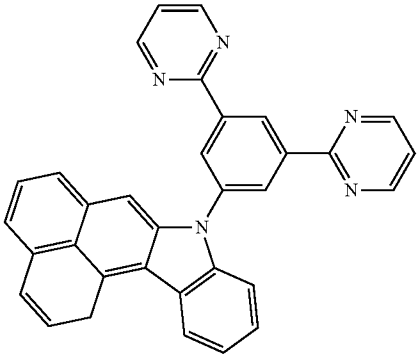
38
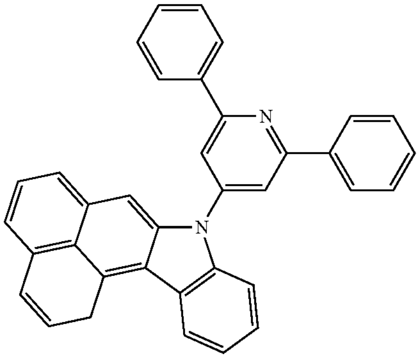
39
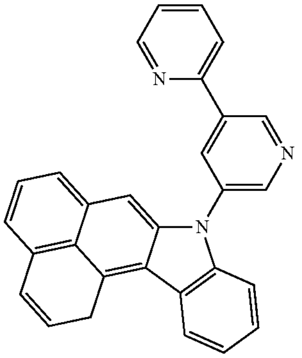
40
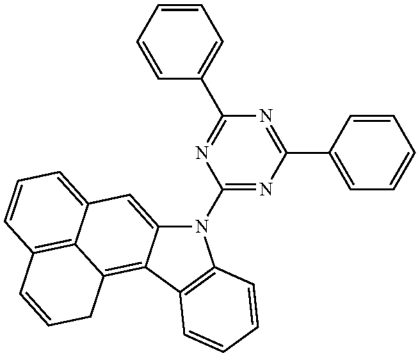

-continued
41
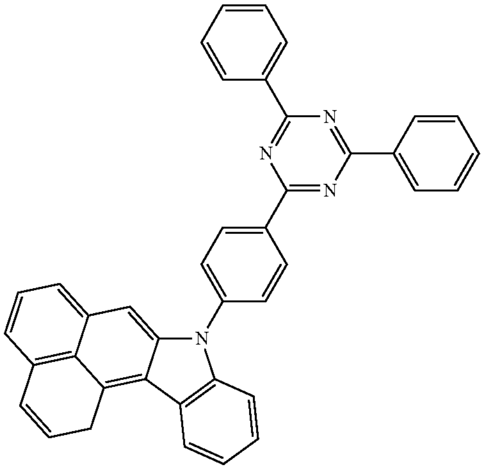
42
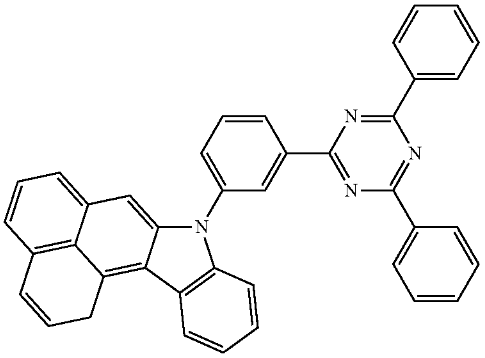
43
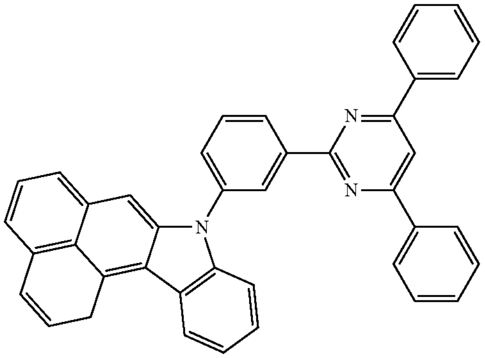
44
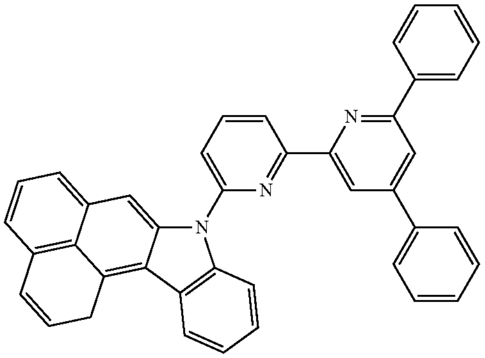
-continued
45
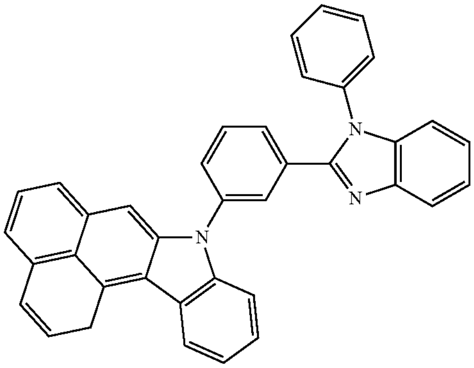
46
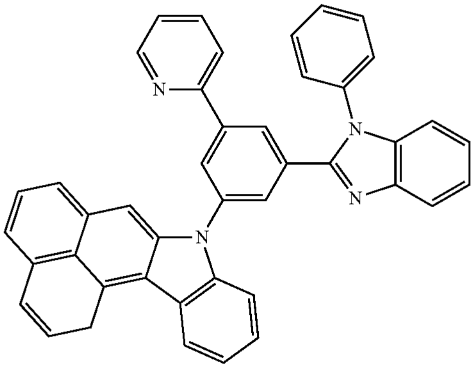
47
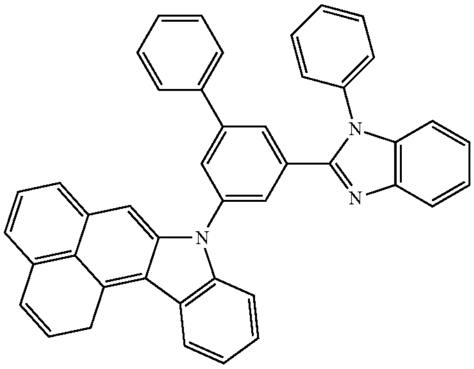
48
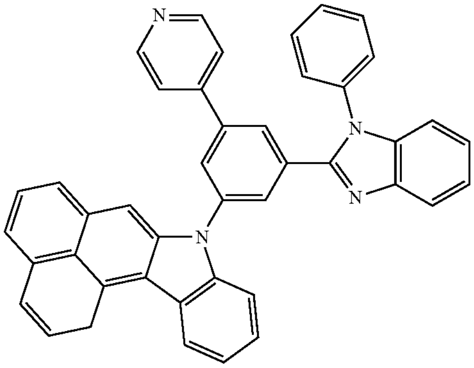

-continued
49
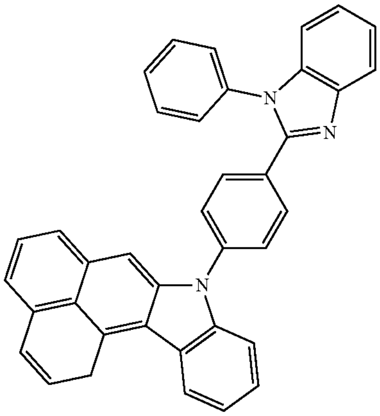
50
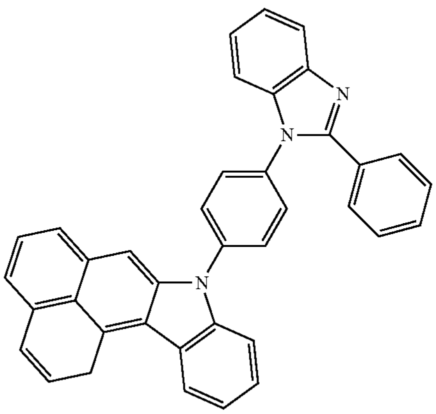
51
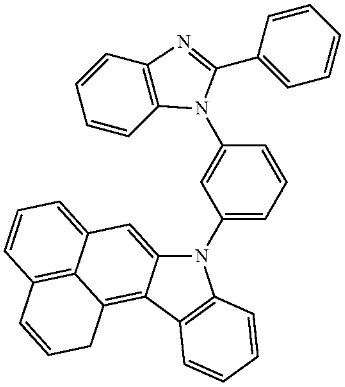
52
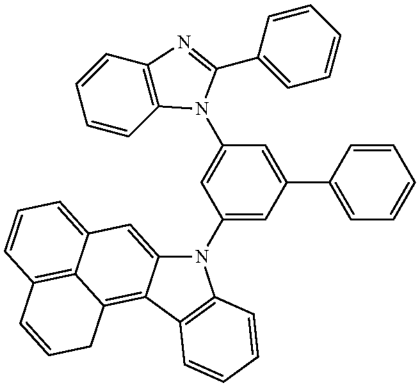
-continued
53
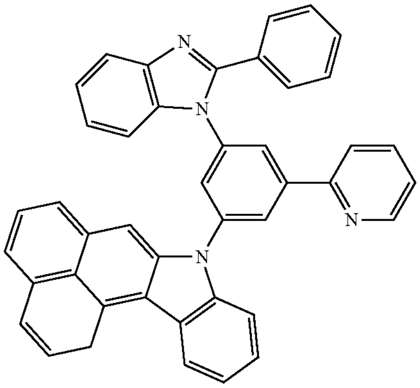
54
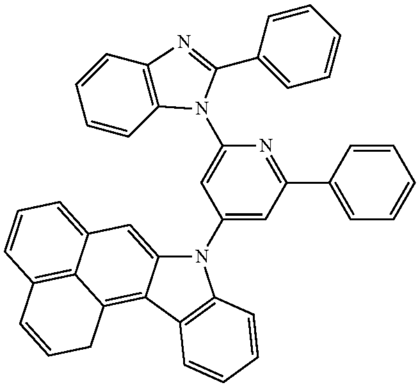
55
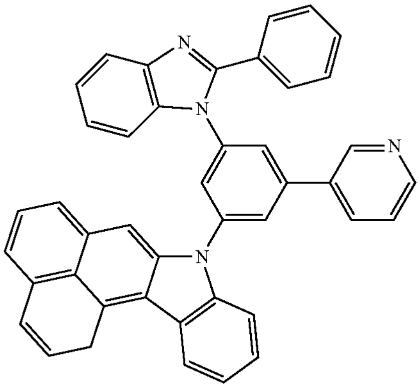
56
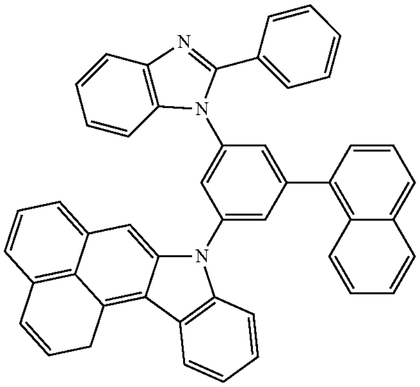
.
The condensed cyclic compound of Formula 1 may include a core represented by Formula 1', and accordingly, may have excellent heat resistance, stability against charges, and/or charge transporting capability, and/or the like. Thus, an organic light-emitting device including the condensed cyclic compound of Formula 1 may have high efficiency and long lifespan.

Formula 1'

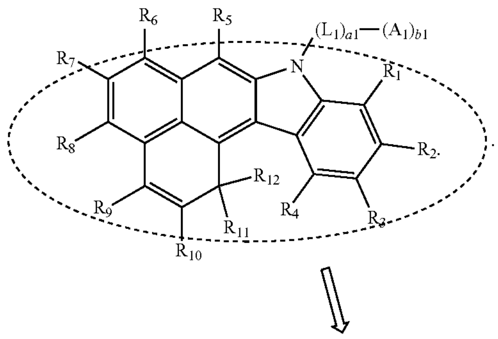

A core

A method of synthesizing the condensed cyclic compound of Formula 1 may be understood by those of ordinary skill in the art based on Examples described below.

At least one of the condensed cyclic compounds of Formula 1 may be used between a pair of electrodes included in an organic light-emitting device. For example, the condensed cyclic compound of Formula 1 may be included in at least one selected from the electron transport region and emission layer. In some embodiments, the condensed cyclic compound of Formula 1 may be used as a material for forming a capping layer, which is positioned outside a pair of electrodes included in an organic light-emitting device.

According to an example embodiment, there is provided an organic light-emitting device including: a first electrode; a second electrode facing the first electrode; and an organic layer between the first electrode and the second electrode and including an emission layer, wherein the organic layer may include at least one of the condensed cyclic compounds of Formula 1.

As used herein, the expression "(an organic layer) may include at least one of the condensed cyclic compounds" may refer to "(an organic layer) may include one condensed cyclic compound represented by Formula 1 or at least two different condensed cyclic compounds represented by Formula 1".

For example, the organic layer may include, as the condensed cyclic compound of Formula 1, only Compound 1. Here, Compound 1 may be included in an electron transport layer of the organic light-emitting device. Alternatively, the organic layer may include, as the condensed cyclic compound of Formula 1, Compound 1 and Compound 2. Here, Compound 1 and Compound 2 may both be in the same layer (e.g., both Compound 1 and Compound 2 may be in an electron transport layer), or Compound 1 and Compound 2 may be in different layers from each other (e.g., Compound 1 may be in an electron transport layer and Compound 2 may be in an emission layer).

The organic layer may further include: i) a hole transport region disposed (e.g., positioned) between the first electrode (e.g., an anode) and the emission layer and including a hole injection layer (HIL), a hole transport layer (HTL), a buffer layer, an electron blocking layer (EBL), or any combination thereof; and ii) an electron transport region disposed between the emission layer and the second electrode (e.g., a cathode) and including a hole blocking layer (HBL), an electron transport layer (ETL), an electron injection layer (EIL), or any combination thereof. At least one of the electron transport region and the emission layer may include at least one of the condensed cyclic compounds of Formula 1. For example, the electron transport region included in the organic light-emitting device may include an ETL, and the ETL may include at least one of the condensed cyclic compounds of Formula 1. In some embodiments, the emission layer included in the organic light-emitting device may include at least one of the condensed cyclic compounds of Formula 1. The condensed cyclic compound of Formula 1 included in the emission layer may serve as a host, and the emission layer may further include a dopant. Here, the dopant may be a phosphorescent dopant and/or a fluorescent dopant.

The organic light-emitting device may further include at least one selected from a first capping layer and a second capping layer, wherein the first capping layer is disposed on a path where light generated from the emission layer is extracted (e.g., directed) to the outside via the first electrode and the second capping layer is disposed on a path where light generated from the emission layer is extracted to the outside via the second electrode. Here, at least one of the first capping layer and the second capping layer may include at least one of the condensed cyclic compounds of Formula 1.

For example, the organic light-emitting device may have i) a structure in which the first electrode, the organic layer, the second electrode, and the second capping layer are sequentially stacked in the stated order, ii) a structure in which the first capping layer, the first electrode, the organic layer, and the second electrode are sequentially stacked in the stated order, or iii) a structure in which the first capping layer, the first electrode, the organic layer, the second electrode, and the second capping layer are sequentially stacked in the stated order, wherein at least one of the first capping layer and the second capping layer may include at least one of the condensed cyclic compounds of Formula 1.

As used herein, the term "organic layer" may refer to a single layer and/or a plurality of layers disposed between the first electrode and the second electrode of the organic light-emitting device. A material included in the "organic layer" is not limited to just organic material.

FIG. 1 is a schematic cross-sectional view of a structure of an organic light-emitting device 10 according to an example embodiment. The organic light-emitting device 10 includes a first electrode 110, an organic layer 150, and a second electrode 190.

Hereinafter, a structure of an organic light-emitting device according to an example embodiment and a method of manufacturing an organic light-emitting device according to an example embodiment will be described in connection with FIG. 1.

In FIG. 1, a substrate may be additionally disposed (e.g., positioned) under the first electrode 110 or above the second electrode 190. The substrate may be a glass substrate or a transparent plastic substrate, each with excellent mechanical strength, thermal stability, transparency, surface smoothness, ease of handling, and/or water-resistance.

The first electrode 110 may be formed by, for example, depositing and/or sputtering a material for forming the first electrode 110 on the substrate. When the first electrode 110 is an anode, the material for forming the first electrode 110 may be selected from materials having a high work function so as to facilitate hole injection. The first electrode may be a reflective electrode, a semi-transparent electrode, or a transparent electrode. The material for forming the first electrode 110 may be a transparent and highly conductive material, and non-limiting examples of such material include indium tin oxide (ITO), indium zinc oxide (IZO), tin oxide, ($SnO_2$), and zinc oxide (ZnO). Alternatively, to form the first electrode 110 as a semi-transparent electrode or a reflective electrode, the material for forming the first electrode 110 may be at least one selected from magnesium (Mg), aluminum (Al), aluminum-lithium (Al—Li), calcium (Ca), magnesium-indium (Mg—In), and magnesium-silver (Mg—Ag).

The first electrode 110 may have a single-layer structure or a multi-layer structure including a plurality of layers. For example, the first electrode 110 may have a triple-layered structure of ITO/Ag/ITO, but the structure of the first electrode 110 is not limited thereto.

The organic layer 150 may be disposed on the first electrode 110 (e.g., on top of the first electrode 110). The organic layer 150 may include the emission layer.

The organic layer 150 may further include a hole transport region disposed between the first electrode 110 and the emission layer and an electron transport region disposed between the emission layer and the second electrode 190.

The hole transport region may include an HIL, an HTL, a buffer layer, an electron blocking layer EBL, or any combination thereof; and the electron transport region may include an HBL, an ETL, an EIL, or any combination thereof, but the hole transport region and the electron transport region are not limited thereto.

The hole transport region may have a single-layer structure formed of a single material, a single-layer structure formed of a plurality of different materials, or a multi-layer structure having a plurality of layers formed of a plurality of different materials.

For example, the hole transport region may have a single-layer structure formed of a plurality of different materials, or a multi-layer structure such as a structure of HIL/HTL, a structure of HIL/HTL/buffer layer, a structure of HIL/buffer layer, a structure of HTL/buffer layer, or a structure of HIL/HTL/EBL. The layers of each structure may be sequentially stacked from the first electrode 100 in this stated order, but the hole transport region is not limited thereto.

When the hole transport region includes an HIL, the HIL may be formed on the first electrode 110 by utilizing various suitable methods, such as vacuum deposition, spin coating, casting, a Langmuir-Blodgett (LB) method, ink-jet printing, laser-printing, and/or a laser induced thermal imaging (LITI) method.

When an HIL is formed by vacuum deposition, the vacuum deposition may be performed, for example, at a deposition temperature of about 100° C. to about 500° C., at a vacuum degree of about $10^{-8}$ torr to about $10^{-3}$ torr, and a deposition rate of about 0.01 Å/sec to about 100 Å/sec, depending upon a composition of a compound for forming the HIL to be deposited and a structure of the HIL to be formed.

When the HIL is formed by spin coating, the spin coating may be performed, for example, at a coating rate of about 2,000 rpm to about 5,000 rpm and at a temperature of about 80° C. to about 200° C., depending upon a composition of a compound for forming the HIL to be deposited and a structure of the HIL to be formed.

When the hole transport region includes an HTL, the HTL may be formed on the first electrode 110 or the HIL by utilizing various suitable methods, such as vacuum deposition, spin coating, casting, an LB method, an ink-jet printing, a laser-printing, and/or an LITI method. When the HTL is formed by vacuum deposition and/or spin coating, the deposition and coating conditions for the HTL may be determined by referring to the deposition and coating conditions for the HIL.

The hole transport region may include the condensed cyclic compound of Formula 1. For example, the hole transport region may include the HTL, and the HTL may include the condensed cyclic compound of Formula 1.

In some embodiments, the hole transport region may include at least one selected from m-MTDATA, TDATA, 2-TNATA, NPB, β-NPB, TPD, Spiro-TPD, Spiro-NPB, methylated NPB, TAPC, HMTPD, 4,4',4"-tris(N-carbazolyl) triphenylamine) (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrene sulfonate) (PANI/PSS), a compound represented by Formula 201, and a compound represented by Formula 202:

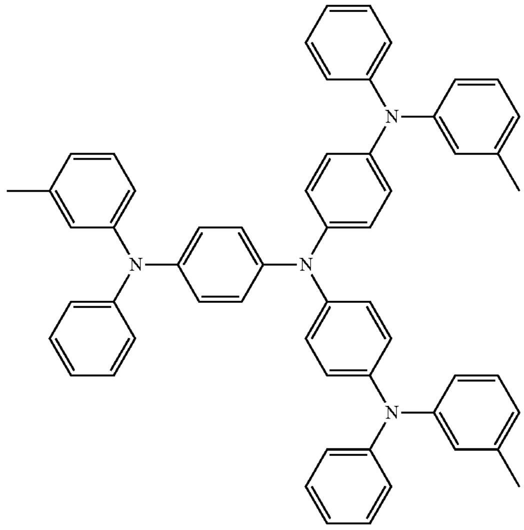

m-MTDATA

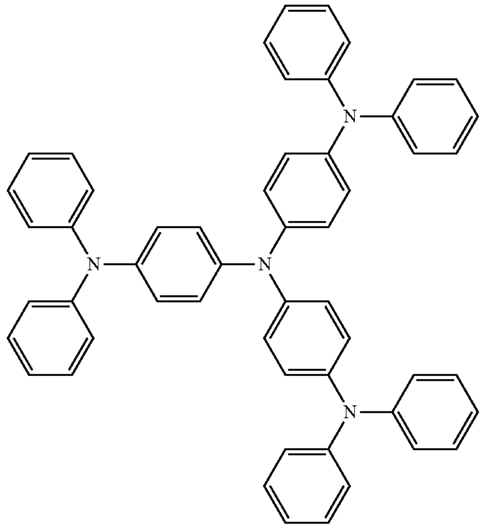

TDATA

-continued
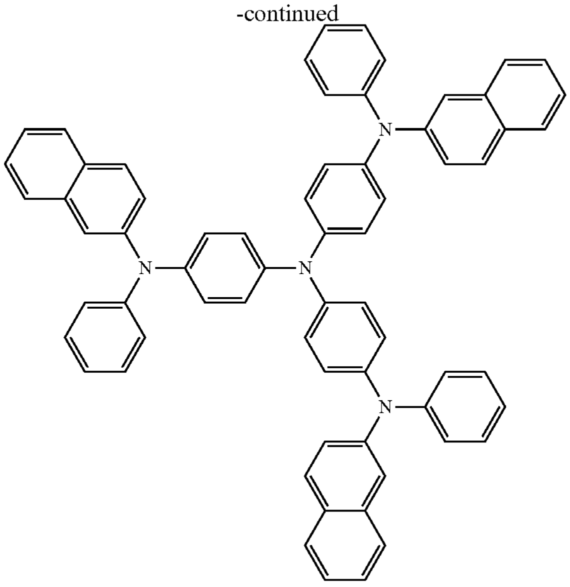
2-TNATA
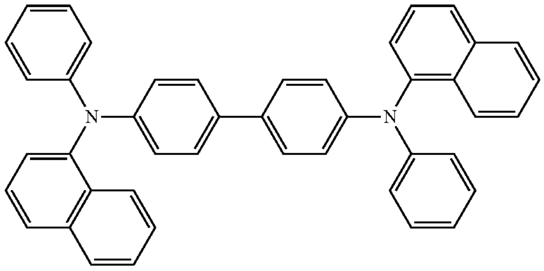
NPB
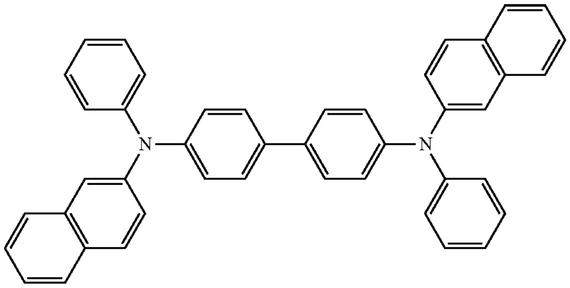
β-NPB
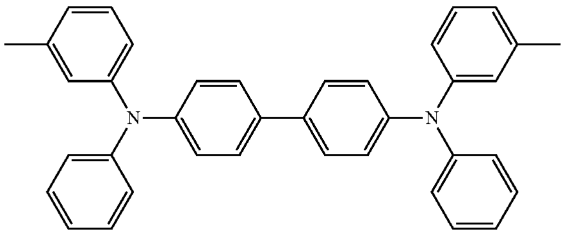
TPD
-continued
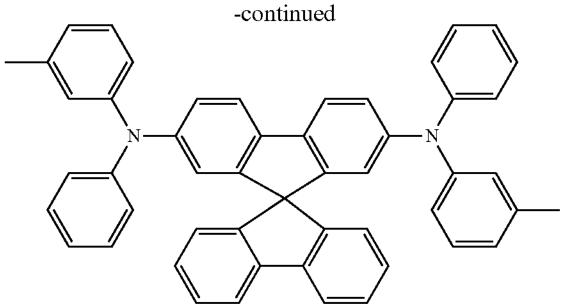
Spiro-TPD
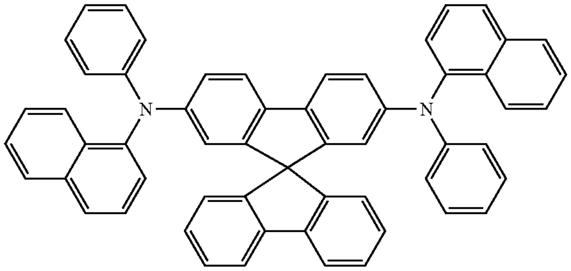
Spiro-NPB
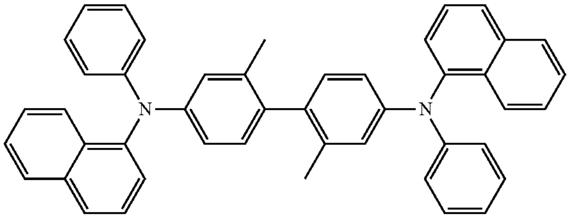
methylated NPB
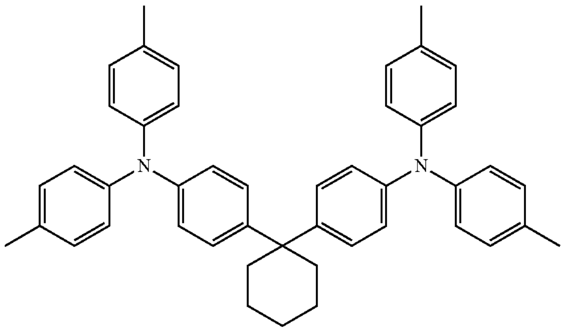
TAPC
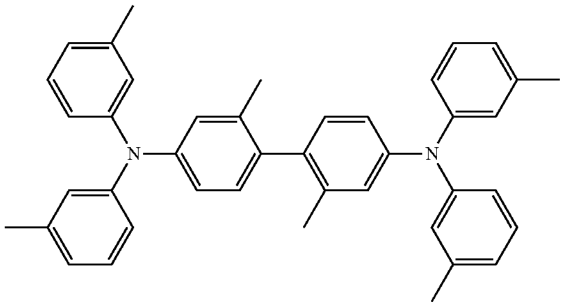
HMTPD
Formula 201
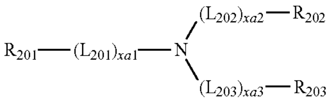

-continued

Formula 202

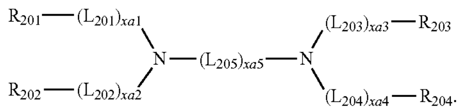

In Formulae 201 and 202, descriptions of $L_{201}$ to $L_{205}$ may be each independently understood by referring to the description of $L_1$ in the present specification, xa1 to xa4 may be each independently selected from 0, 1, 2, and 3, xa5 may be selected from 1, 2, 3, 4, and 5, and $R_{201}$ to $R_{204}$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formulae 201 and 202, $L_{201}$ to $L_{205}$ may be each independently selected from:

a phenylene group, a naphthylene group, a fluorenylene group, a spiro-bifluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-bifluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group, xa1 to xa4 may be each independently 0, 1 or 2, xa5 may be 1, 2, or 3, and $R_{201}$ to $R_{204}$ may be each independently selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, an azulenyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments are not limited thereto.

The compound of Formula 201 may be represented by Formula 201A, but is not limited thereto:

Formula 201A

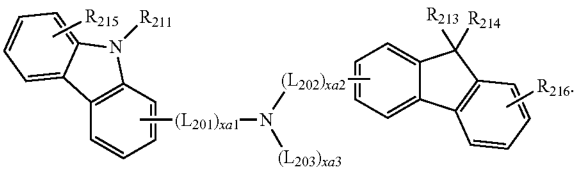

For example, the compound of Formula 201 may be represented by Formula 201A-1, but is not limited thereto:

Formula 201A-1

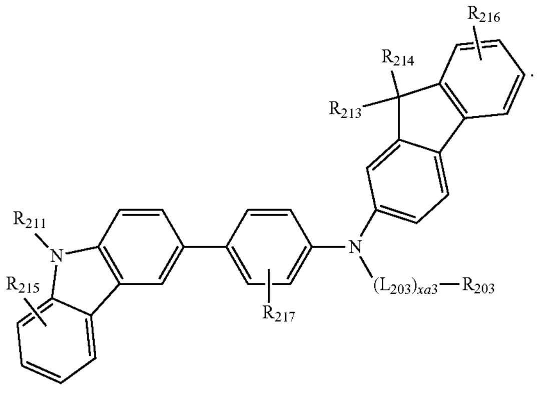

The compound of Formula 202 may be represented by Formula 202A, but is not limited thereto:

Formula 202A

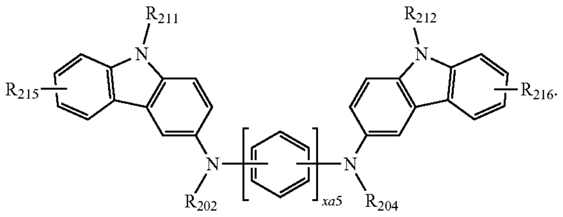

In Formulae 201A, 201A-1, and 202A, descriptions of $L_{201}$ to $L_{203}$, xa1 to xa3, xa5, and $R_{202}$ to $R_{204}$ may be each independently understood by referring to the descriptions thereof in the present disclosure, and descriptions of $R_{211}$ and $R_{212}$ may be each independently understood by referring to the description of $R_{203}$ in the present disclosure.

In Formulae 201A, 201A-1, and 202A, $R_{213}$ to $R_{217}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

The compound of Formula 201 and the compound of Formula 202 may each independently include any of Compounds HT1 to HT20, but embodiments are not limited thereto.

HT1

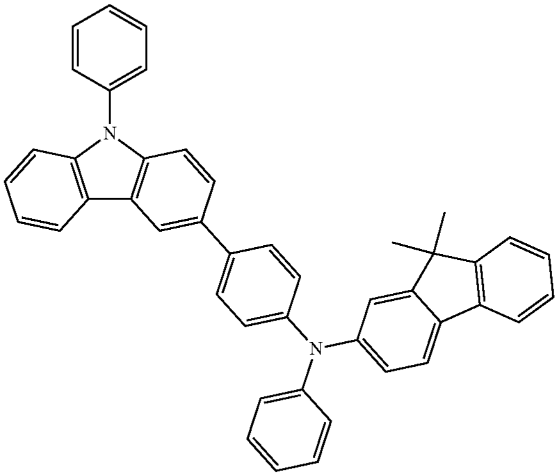

-continued

HT2

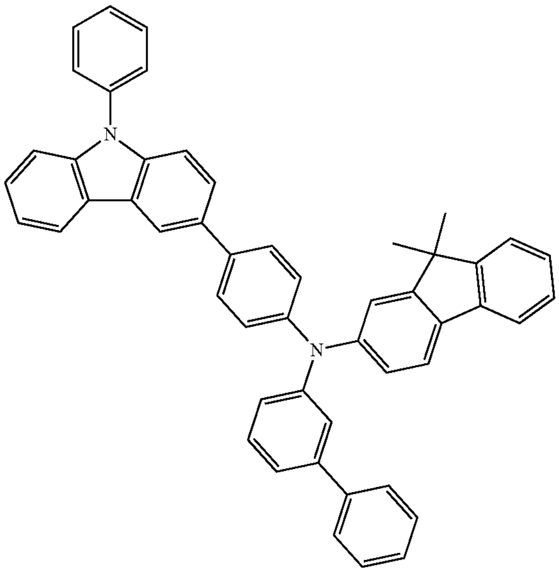

HT3

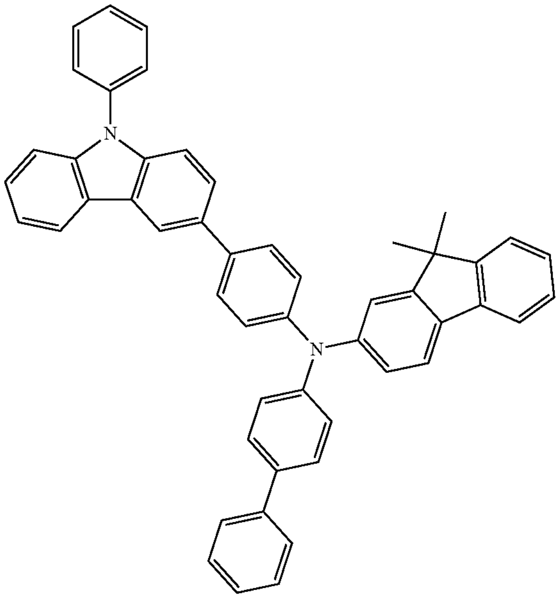

HT4
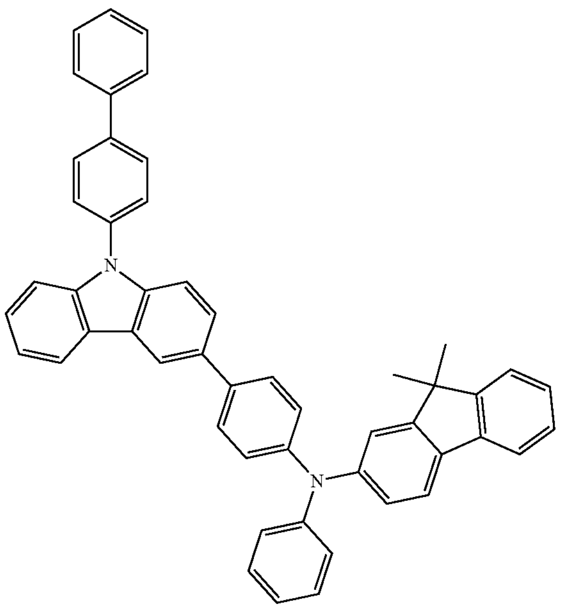
HT6
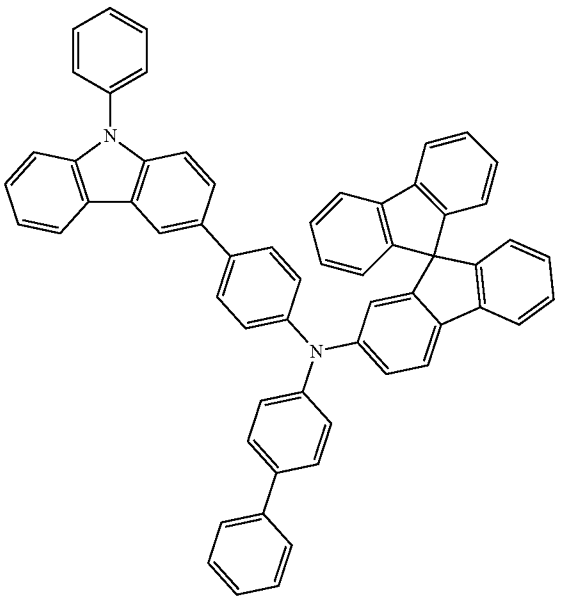
HT5
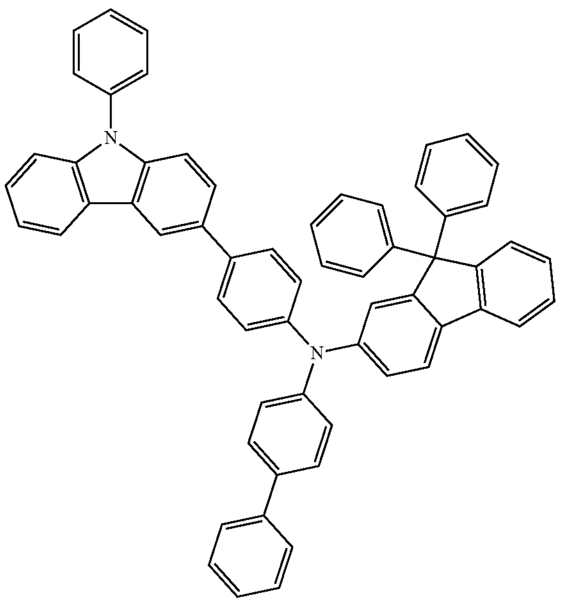
HT7
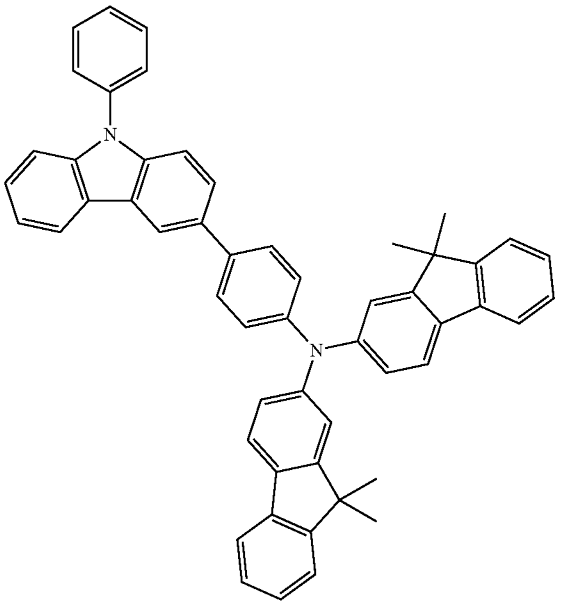

-continued
HT8
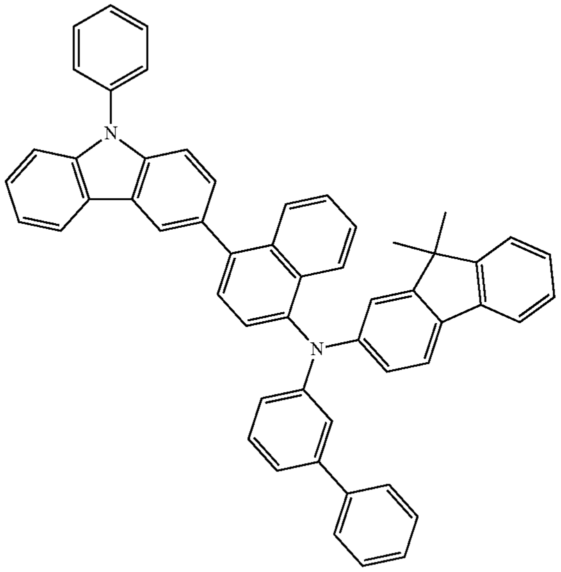
HT9
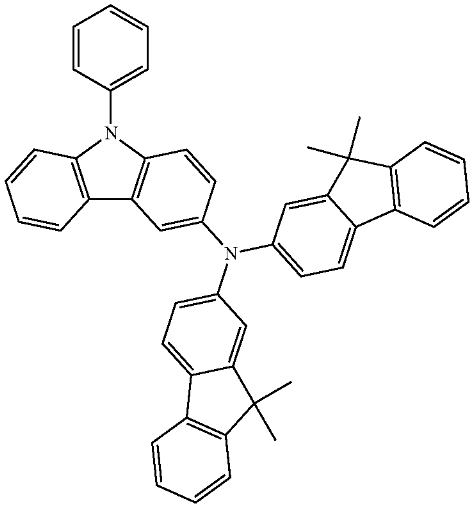
-continued
HT10
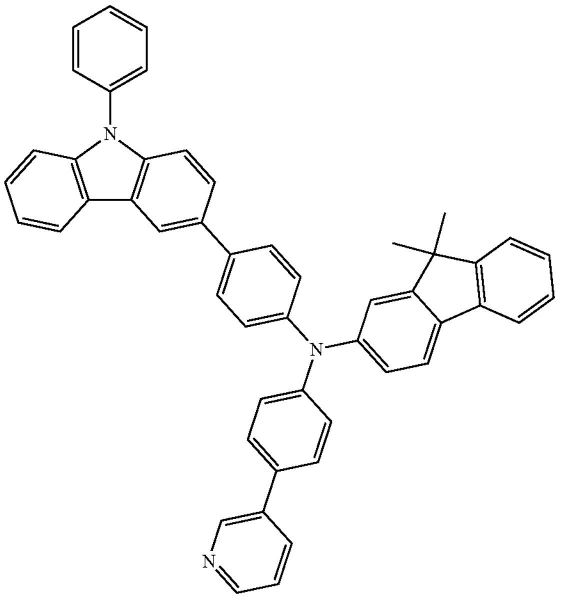
HT11
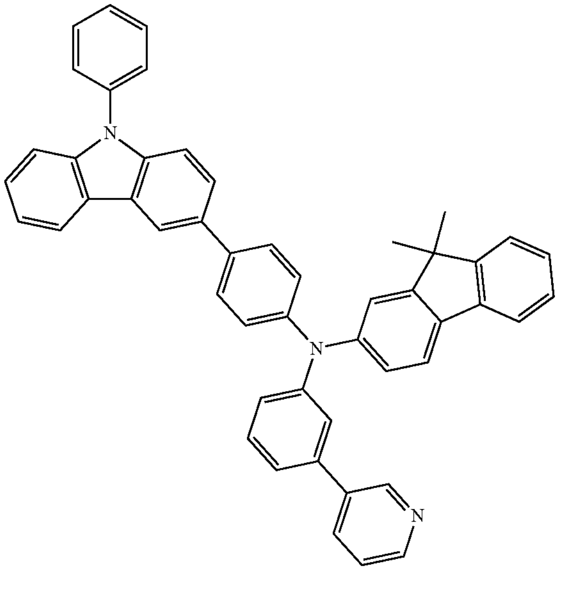

-continued
HT12
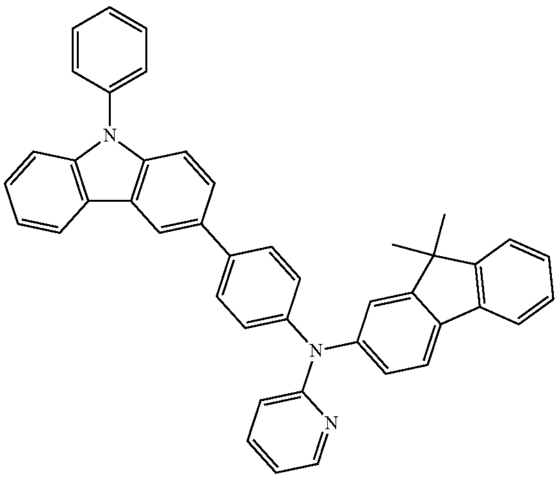
HT13
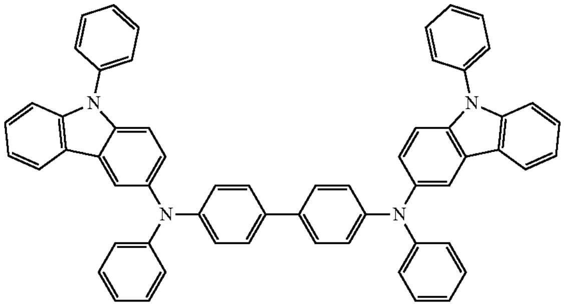
HT14
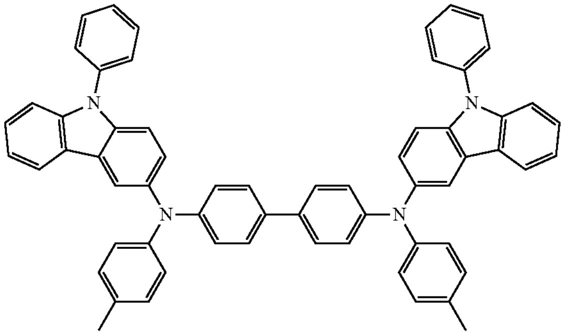
HT15
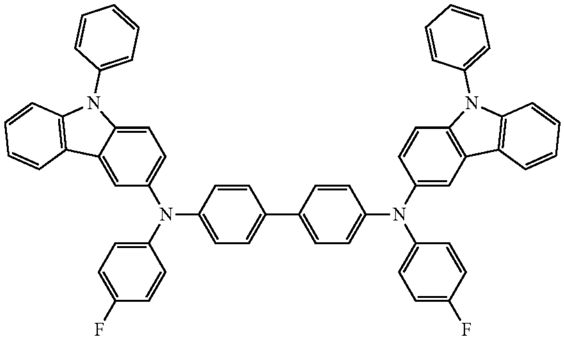
-continued
HT16
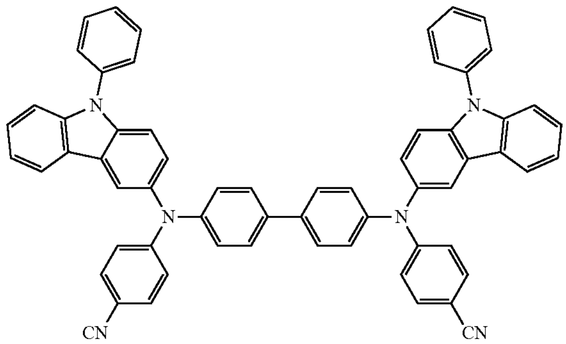
HT17
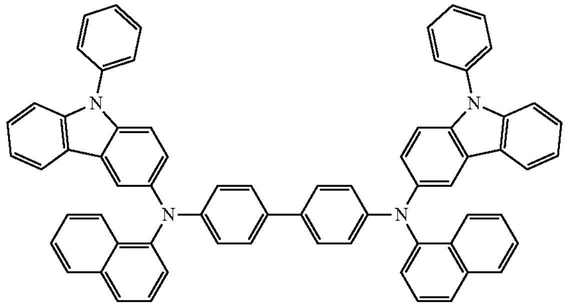
HT18
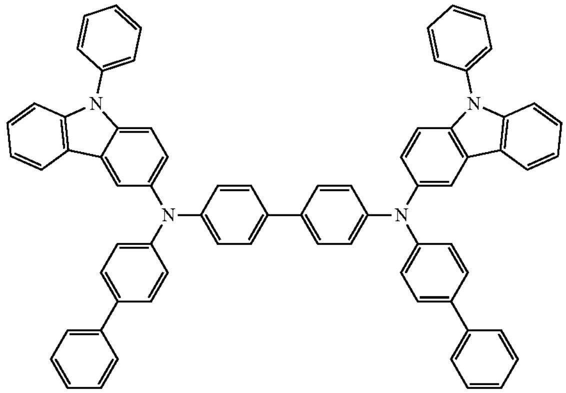
HT19
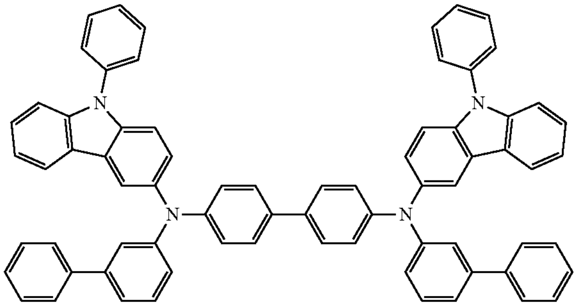

-continued

HT20

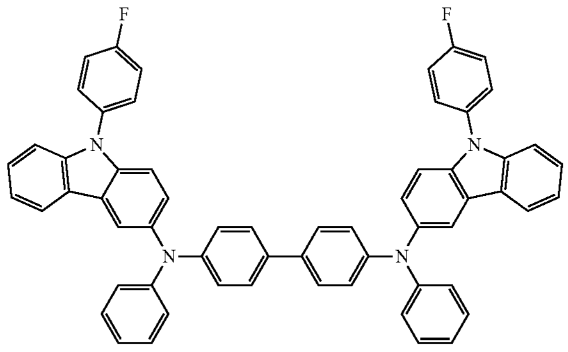

A thickness of the hole transport region may be in a range of about 100 Å to about 10,000 Å, for example, about 100 Å to about 1,000 Å. When the hole transport region includes at least one selected from an HIL and an HTL, a thickness of the HIL may be in a range of about 100 Å to about 10,000 Å, for example, about 100 Å to about 1,000 Å, and a thickness of the HTL may be in a range of about 50 Å to about 2,000 Å, for example, about 100 Å to about 1,500 Å. When the thicknesses of the hole transport region, HIL, and the HTL are within any of these ranges, satisfactory (or suitable) hole transporting properties may be obtained without a substantial increase in driving voltage.

The hole transport region may further include, in addition to the materials described above, a charge-generating material to improve conductive property. The charge-generating material may be homogeneously or non-homogeneously dispersed throughout the hole transport region.

The charge-generating material may be, for example, a p-dopant. The p-dopant may be selected from a quinone derivative, a metal oxide, and a cyano group-containing compound, but embodiments are not limited thereto. Examples of the p-dopant include quinone derivatives (such as tetracyanoquinonedimethane (TCNQ) and/or 2,3,5,6-tetrafluoro-tetracyano-1,4-benzoquinonedimethane (F4-TCNQ)); metal oxides (such as tungsten oxide and/or molybdenum oxide); and Compound HT-D1, but embodiments are not limited thereto:

Compound HT-D1

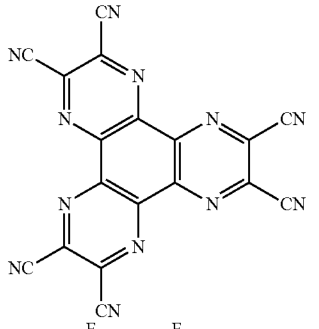

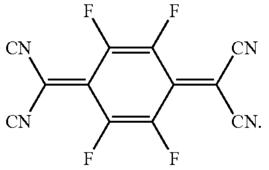

F4-TCNQ

The hole transport region may further include, in addition to the HIL and the HTL described above, at least one selected from a buffer layer and an EBL. The buffer layer may compensate for an optical resonance distance according to a wavelength of light emitted from the emission layer, and thus, a light-emission efficiency of the formed organic light-emitting device may be improved. The buffer layer may include any suitable material utilized in the hole transport region. The EBL may serve as a functional layer that prevents or reduces the diffusion of electrons into the electron transport region.

The emission layer may be disposed on the first electrode 110 or on the hole transport region by utilizing various suitable methods, such as vacuum deposition, spin coating, casting, an LB method, an ink-jet printing, a laser-printing, and/or an LITI method. When the emission layer is formed by vacuum deposition and/or spin coating, the deposition and coating conditions for the emission layer may be determined by referring to the deposition and coating conditions for the HIL.

When the organic light-emitting device 10 is a full-color organic light-emitting device, the emission layer may be patterned into a red emission layer, a green emission layer, and a blue emission layer according to each individual sub-pixel. Alternatively, the emission layer may have a multi-layer structure in which a red emission layer, a green emission layer, and a blue emission layer are stacked on each other, or a single-layer structure including a red-light emitting material, a green-light emitting material, and a blue-light emitting material, to thereby emit white light.

The emission layer may include a host and a dopant. The host may include the condensed cyclic compound of Formula 1. When the emission layer includes the condensed cyclic compound, which acts as the host, and the dopant, an amount of the condensed cyclic compound in the emission layer may be greater than an amount of the dopant in the emission layer.

In some embodiments, the host may include a compound represented by Formula 301:

$$Ar_{301}-[(L_{301})_{xb1}-R_{301}]_{xb2}. \quad \text{Formula 301}$$

In Formula 301, $Ar_{301}$ may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (where $Q_{301}$ to $Q_{303}$ may be each independently selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group), a description of $L_{301}$ may be understood by referring to the description of $L_1$ in the present specification, $R_{301}$ may be selected from:

a $C_1$-$C_{20}$ alkyl group and a $C_1$-$C_{20}$ alkoxy group, a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xb1 may be selected from 0, 1, 2, and 3, and xb2 may be selected from 1, 2, 3, and 4.

For example, in Formula 301, $L_{301}$ may be selected from:

a phenylene group, a naphthylene group, a fluorenylene group, a spiro-bifluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-bifluorenylene group, a benzofluorenylene group, a dibenzofluorenylene group, a phenanthrenylene group, an anthracenylene group, a pyrenylene group, and a chrysenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, and a chrysenyl group, and $R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, and a chrysenyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, and a chrysenyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, and a chrysenyl group, each substituted with at least one selected from deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, and a chrysenyl group, but embodiments are not limited thereto.

For example, the host may include a compound represented by Formula 301A:

Formula 301A

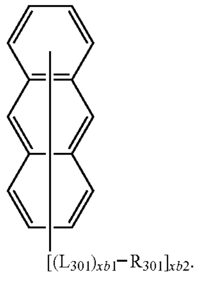

Descriptions of substituents in Formula 301A may be each independently understood by referring to the descriptions thereof in the present specification.
The compound of Formula 301 may include at least one of Compounds H1 to H42, but is not limited thereto:
H1
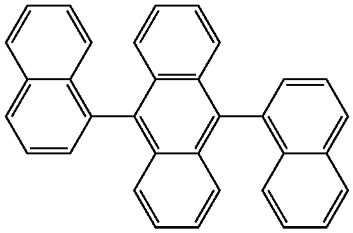
H2
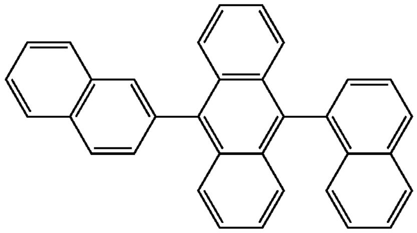
H3
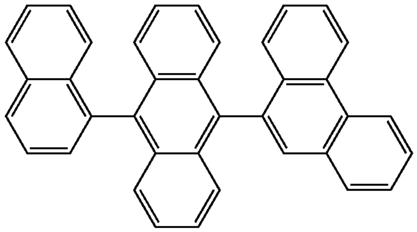
H4
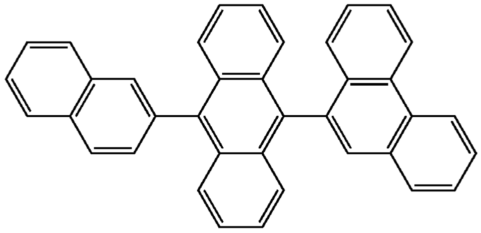
H5
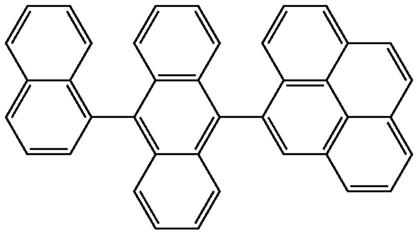
H6
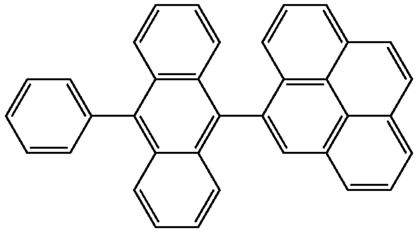
-continued
H7
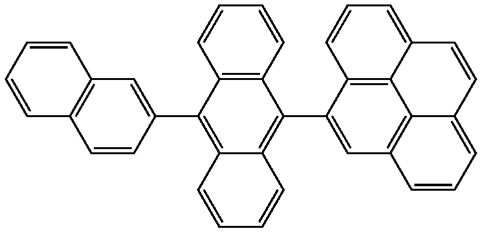
H8
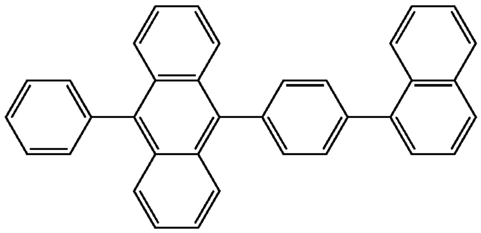
H9
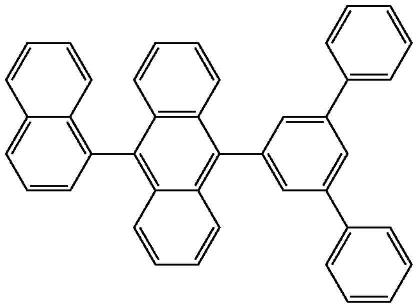
H10
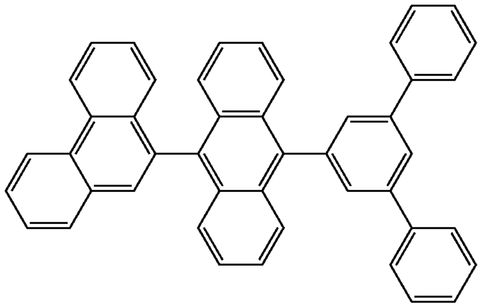
H11
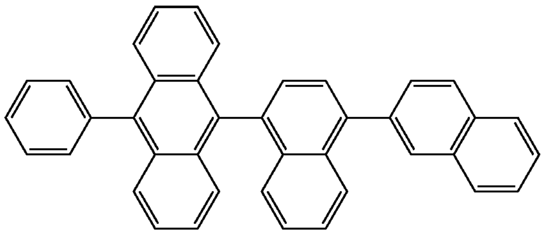
H12
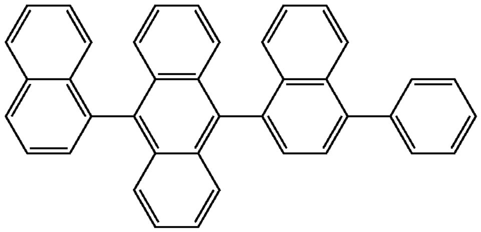

-continued
H13
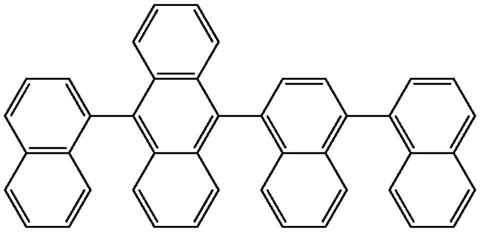
H14
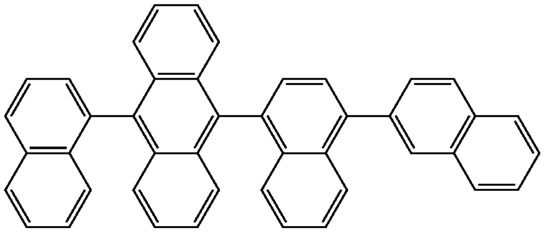
H15
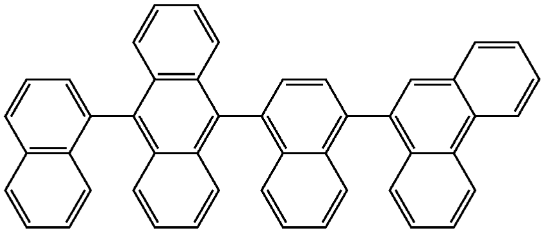
H16
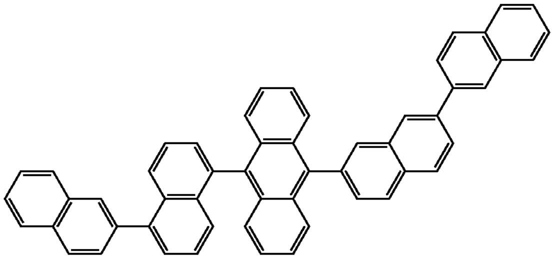
H17
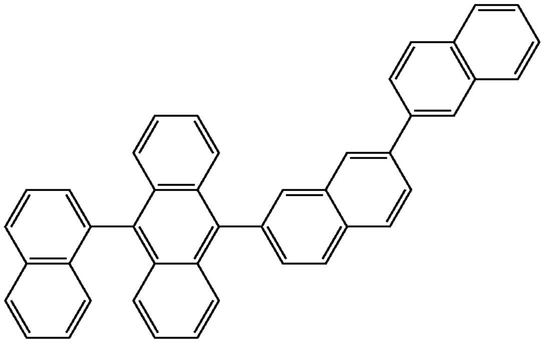
-continued
H18
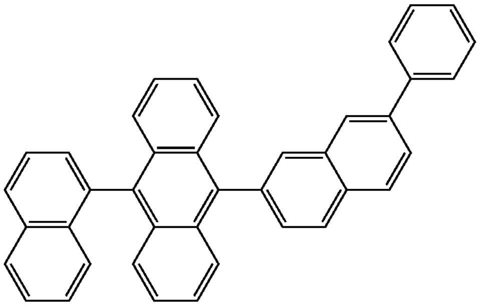
H19
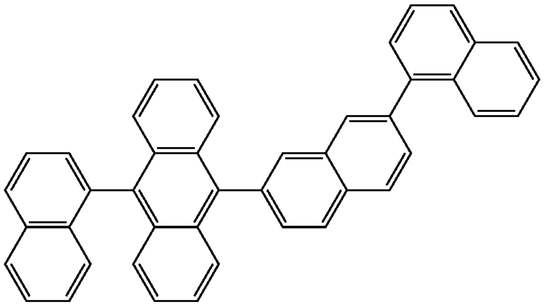
H20
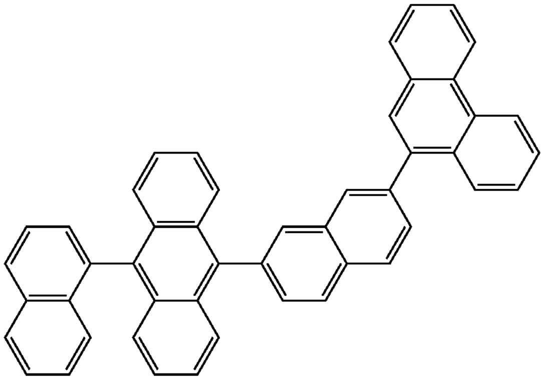
H21
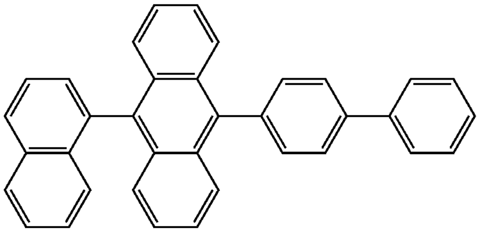
H22
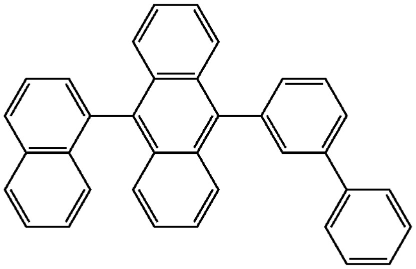

-continued
H23
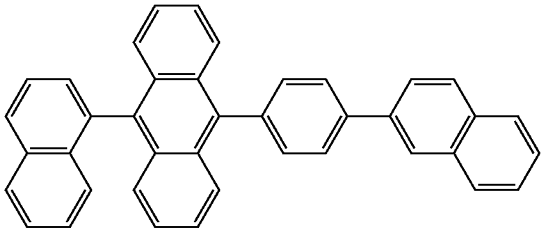
H24
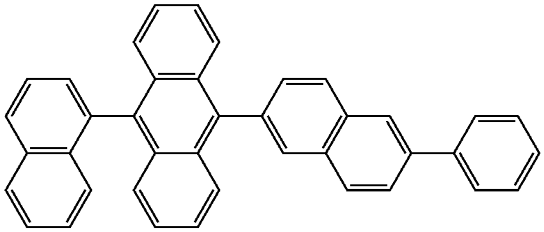
H25
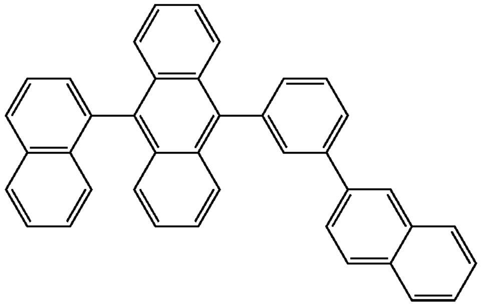
H26
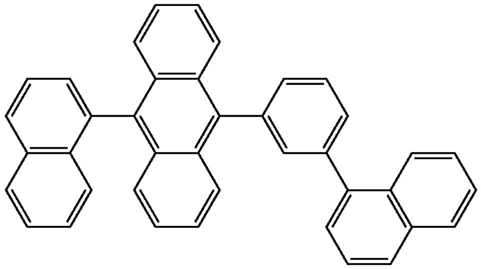
H27
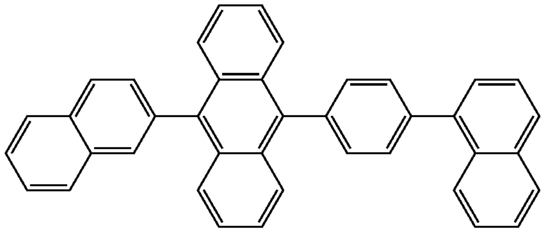
H28
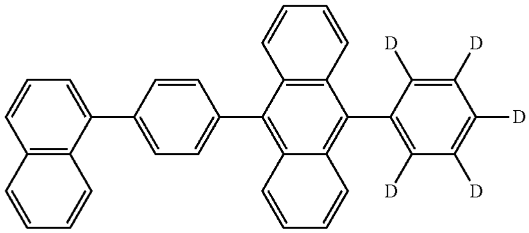
-continued
H29
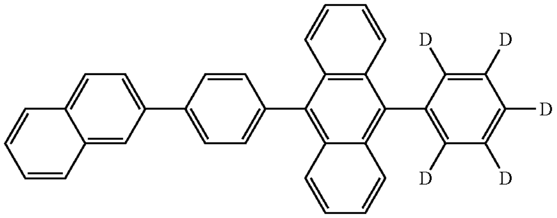
H30
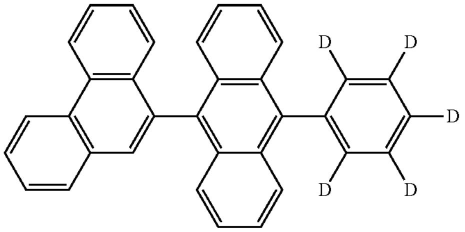
H31
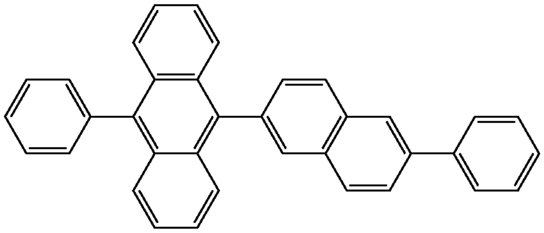
H32
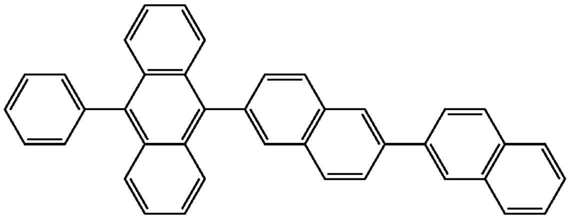
H33
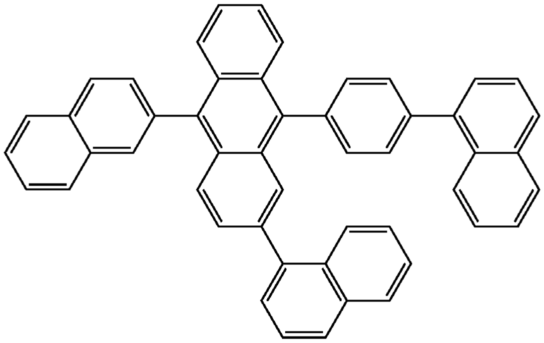

-continued
H34
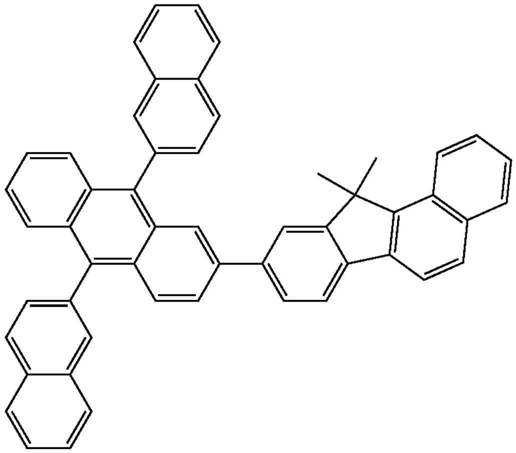
H35
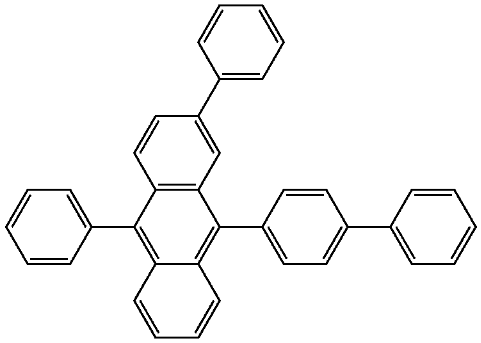
H36
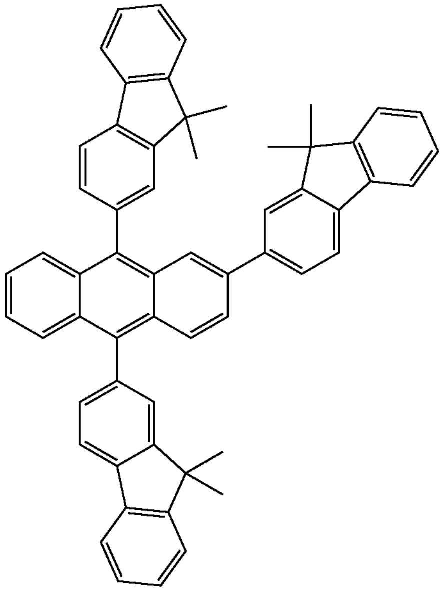
-continued
H37
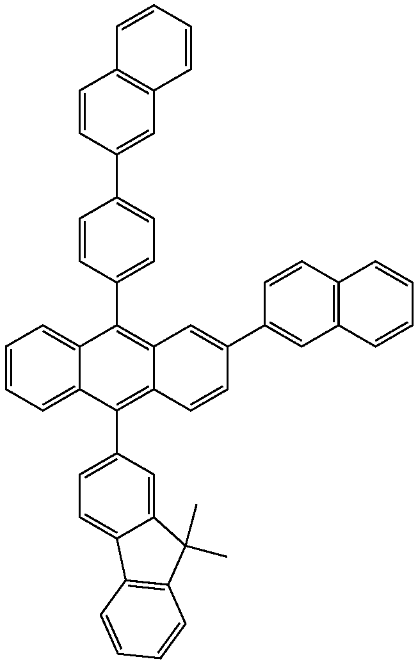
H38
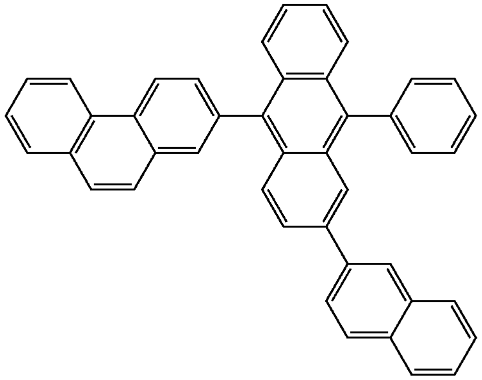
H39
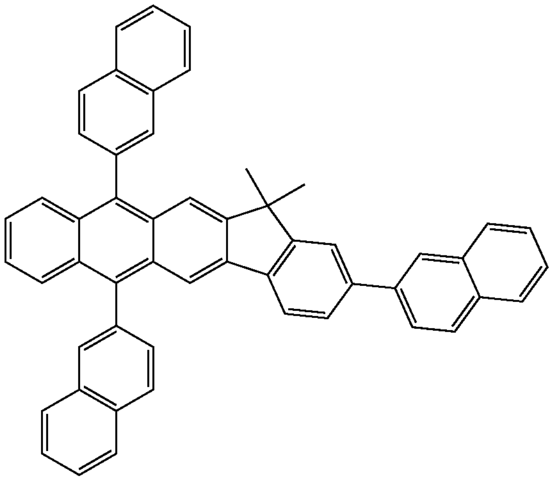

-continued
H40
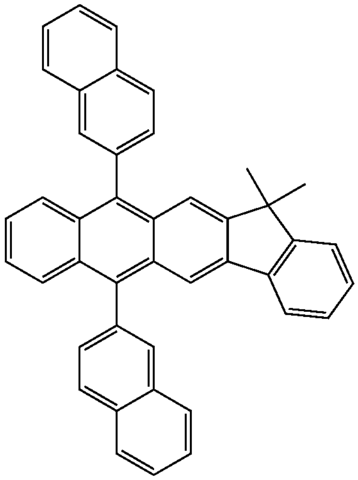
H41
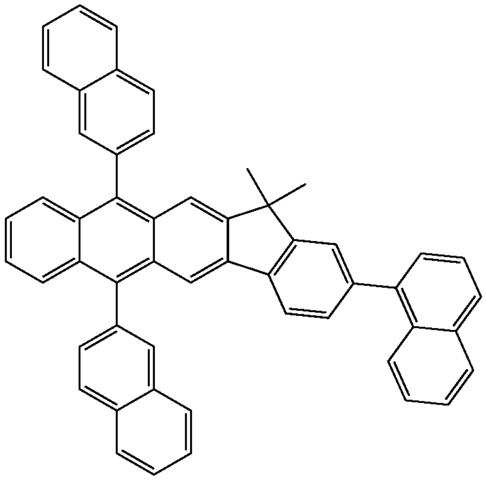
H42
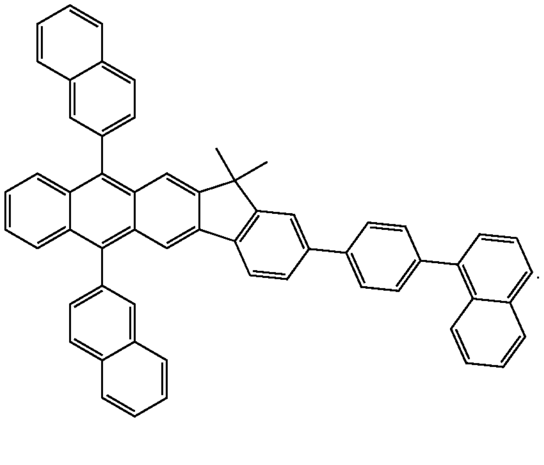
In some embodiments, the host may include at least one of Compounds H43 to H49, but is not limited thereto:
In some embodiments, the host may include one of compounds below, but is not limited thereto:
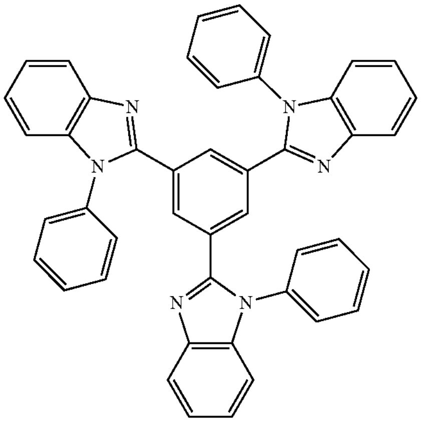
TPBi
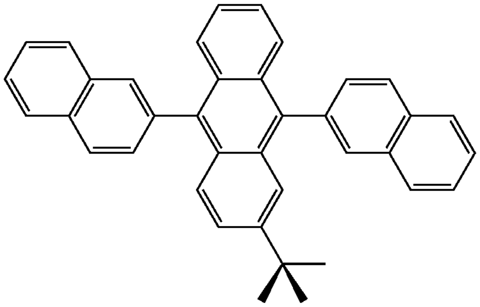
TBADN
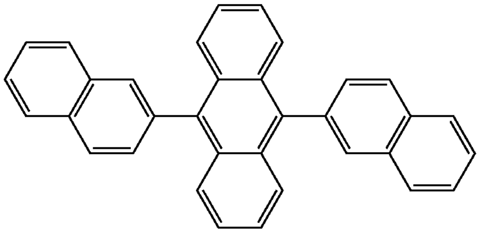
ADN
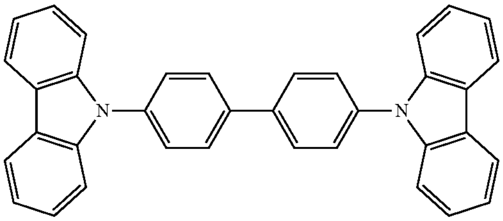
CBP
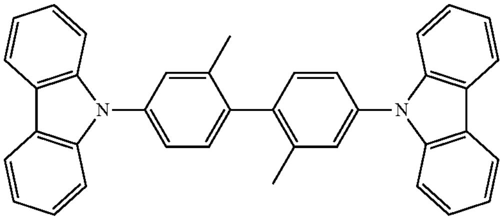
CDBP -continued

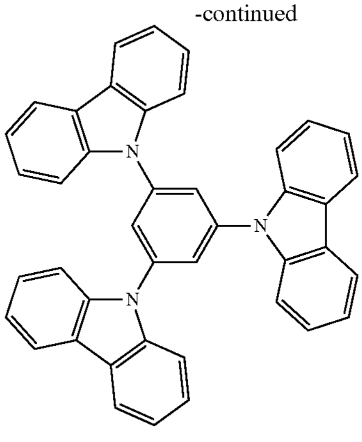

TCP

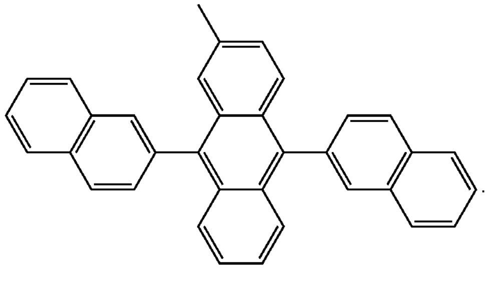

MADN

The dopant included in the emission layer may include a phosphorescent dopant and/or a fluorescent dopant.

The phosphorescent dopant may include an organometallic complex represented by Formula 401:

Formula 401

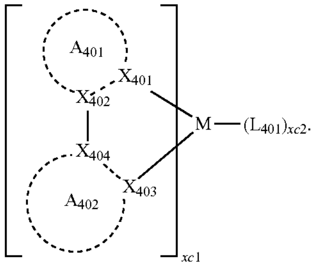

In Formula 401,

M may be selected from iridium (Ir), platinum (Pt), osmium (Os), titanium (Ti), zirconium (Zr), hafnium (Hf), europium (Eu), terbium (Tb), and thulium (Tm), $X_{401}$ to $X_{404}$ may be each independently nitrogen or carbon, rings $A_{401}$ and $A_{402}$ may be each independently selected from a substituted or unsubstituted benzene group, a substituted or unsubstituted naphthalene group, a substituted or unsubstituted fluorene group, a substituted or unsubstituted spiro-bifluorene group, a substituted or unsubstituted indene group, a substituted or unsubstituted pyrrole group, a substituted or unsubstituted thiophene group, a substituted or unsubstituted furan group, a substituted or unsubstituted imidazole group, a substituted or unsubstituted pyrazole group, a substituted or unsubstituted thiazole group, a substituted or unsubstituted isothiazole group, a substituted or unsubstituted oxazole group, a substituted or unsubstituted isoxazole group, a substituted or unsubstituted pyridine group, a substituted or unsubstituted pyrazine group, a substituted or unsubstituted pyrimidine group, a substituted or unsubstituted pyridazine group, a substituted or unsubstituted quinoline group, a substituted or unsubstituted isoquinoline group, a substituted or unsubstituted benzoquinoline group, a substituted or unsubstituted quinoxaline group, a substituted or unsubstituted quinazoline group, a substituted or unsubstituted carbazole group, a substituted or unsubstituted benzoimidazole group, a substituted or unsubstituted benzofuran group, a substituted or unsubstituted benzothiophene group, a substituted or unsubstituted isobenzothiophene group, a substituted or unsubstituted benzoxazole group, a substituted or unsubstituted isobenzoxazole group, a substituted or unsubstituted triazole group, a substituted or unsubstituted oxadiazole group, a substituted or unsubstituted triazine group, a substituted or unsubstituted dibenzofuran group, and a substituted or unsubstituted dibenzothiophene group, at least one substituent of the substituted benzene group, the substituted naphthalene group, the substituted fluorene group, the substituted spiro-bifluorene group, the substituted indene group, the substituted pyrrole group, the substituted thiophene group, the substituted furan group, the substituted imidazole group, the substituted pyrazole group, the substituted thiazole group, the substituted isothiazole group, the substituted oxazole group, the substituted isoxazole group, the substituted pyridine group, the substituted pyrazine group, the substituted pyrimidine group, the substituted pyridazine group, the substituted quinoline group, the substituted isoquinoline group, the substituted benzoquinoline group, the substituted quinoxaline group, the substituted quinazoline group, the substituted carbazole group, the substituted benzoimidazole group, the substituted benzofuran group, the substituted benzothiophene group, the substituted isobenzothiophene group, the substituted benzoxazole group, the substituted isobenzoxazole group, the substituted triazole group, the substituted oxadiazole group, the substituted triazine group, the substituted dibenzofuran group, and the substituted dibenzothiophene group may be selected from:

deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, $—N(Q_{401})(Q_{402})$, $—Si(Q_{403})(Q_{404})(Q_{405})$, and $—B(Q_{406})(Q_{407})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, $—N(Q_{411})(Q_{412})$, $—Si(Q_{413})(Q_{414})(Q_{415})$, and $—B(Q_{416})(Q_{417})$; and $—N(Q_{421})(Q_{422})$, $—Si(Q_{423})(Q_{424})(Q_{425})$, and $—B(Q_{426})(Q_{427})$, wherein $Q_{401}$ to $Q_{407}$, $Q_{411}$ to $Q_{417}$, and $Q_{421}$ to $Q_{427}$ in Formula 401 may be each independently selected from hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group;

$L_{401}$ may be an organic ligand, xc1 may be 1, 2, or 3, and xc2 may be 0, 1, 2, or 3.

$L_{401}$ in Formula 401 may be a monovalent organic ligand, a divalent organic ligand, or a trivalent organic ligand. For example, $L_{401}$ in Formula 401 may be selected from a halogen ligand (e.g., Cl and/or F), a diketone ligand (e.g., acetylacetonate, 1,3-diphenyl-1,3-propane dionate, 2,2,6,6-tetramethyl-3,5-heptanedionate, and/or hexa fluoroacetonate), a carboxylic acid ligand (e.g., picolinate, dimethyl-3-pyrazolecarboxylate, and/or benzoate), a carbon monoxide ligand, an isonitrile ligand, a cyano group ligand, and a phosphorus ligand (e.g., phosphine and/or phosphite), but is not limited thereto.

When ring $A_{401}$ in Formula 401 has two or more substituents, the plurality of substituents of ring $A_{401}$ may bind to each other to form a saturated or unsaturated ring.

When ring $A_{402}$ in Formula 401 has two or more substituents, the plurality of substituents of ring $A_{402}$ may bind to each other to form a saturated or unsaturated ring.

When xc1 in Formula 401 is 2 or more, a plurality of ligands deonoted as

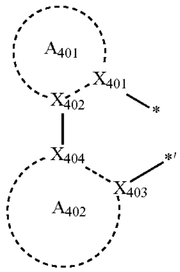

may be identical to or different from each other. When xc1 in Formula 401 is 2 or more, rings $A_{401}$ and $A_{40}$ may each independently be respectively connected (or coupled) to rings $A_{401}$ and $A_{402}$ of other neighboring ligands, either directly (e.g., via a bond such as a single bond) or via a linking group (e.g., a $C_{1-5}$ alkylene group, *—O—*' *—S—*', *—N(R')—*' (where R' is a $C_1$-$C_{10}$ alkyl group or a $C_6$-$C_{20}$ aryl group) and/or *—C(═O)—*').

The phosphorescent dopant may be, for example, selected from Compounds PD1 to PD75, but is not limited thereto:

PD1

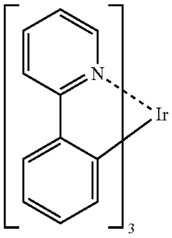

PD2

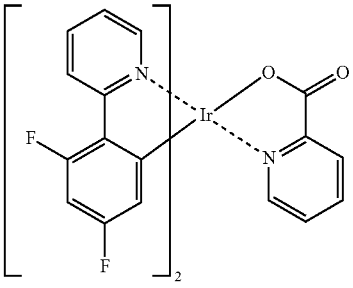

PD3

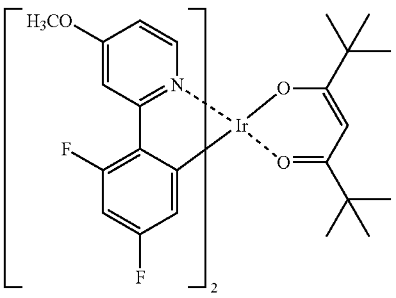

PD4

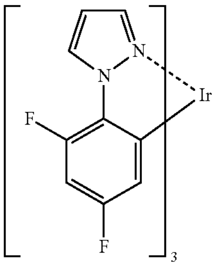

-continued
PD5
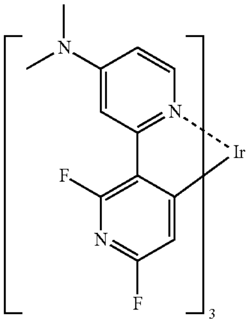
PD6
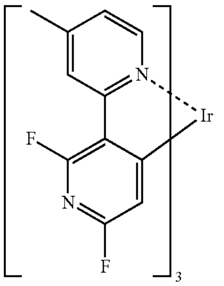
PD7
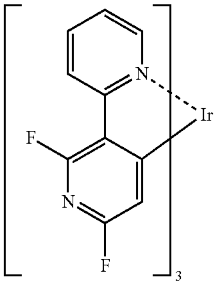
PD8
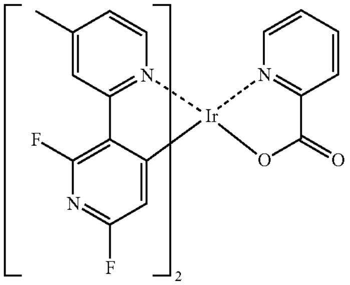
PD9
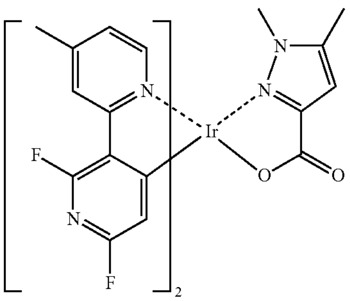
-continued
PD10
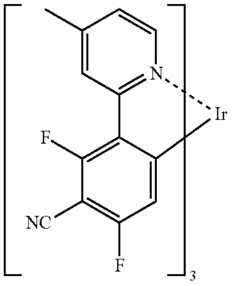
PD11
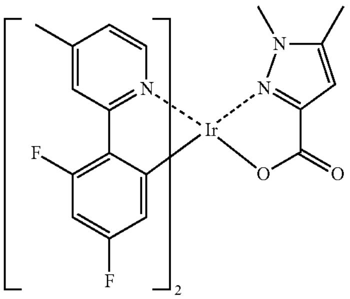
PD12
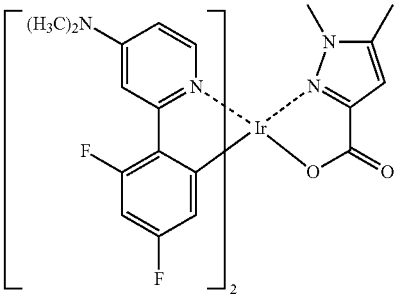
PD13
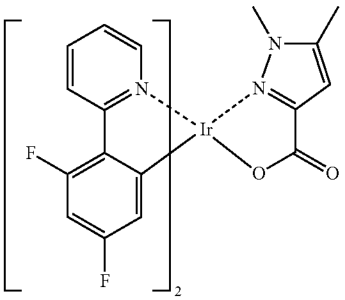
PD14
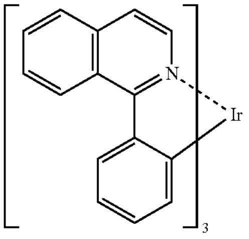

-continued
PD15
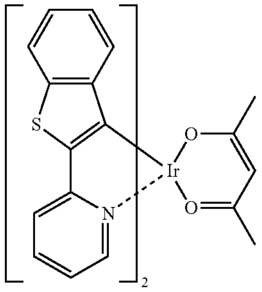
PD16
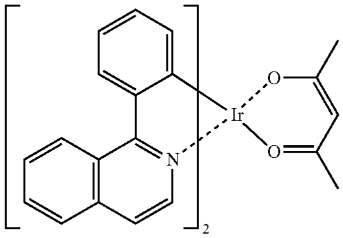
PD17
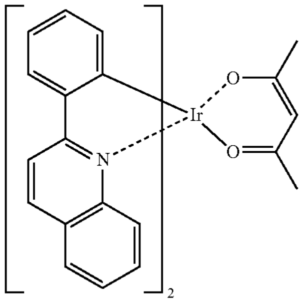
PD18
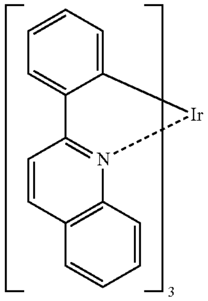
PD19
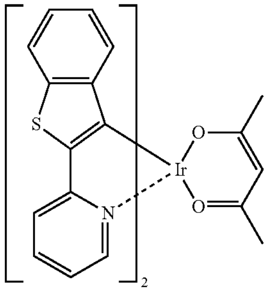
-continued
PD20
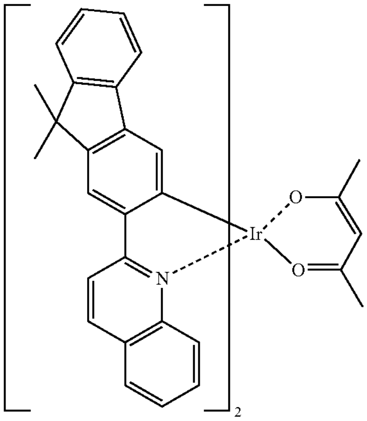
PD21
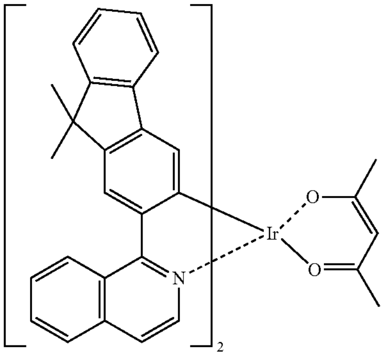
PD22
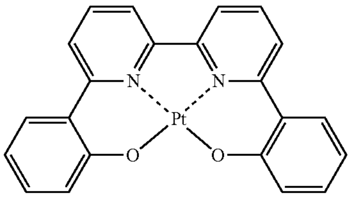
PD23
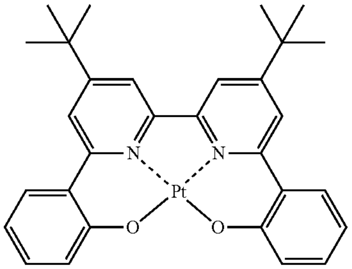
PD24
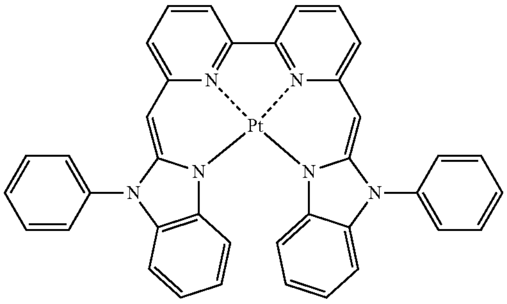

PD25
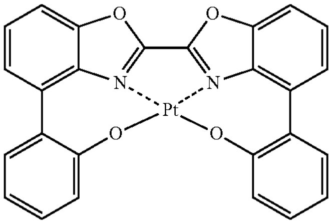
PD26
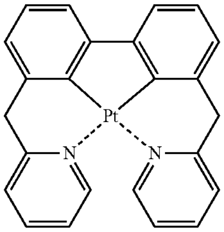
PD27
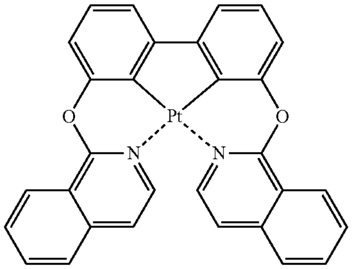
PD28
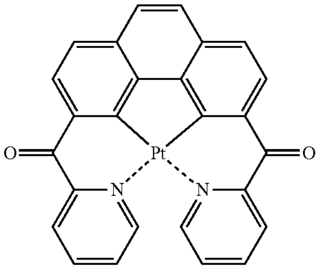
PD29
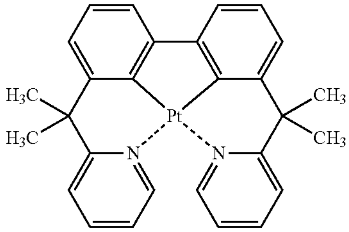
PD30
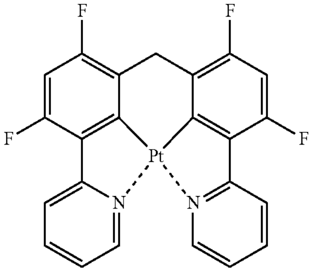
PD31
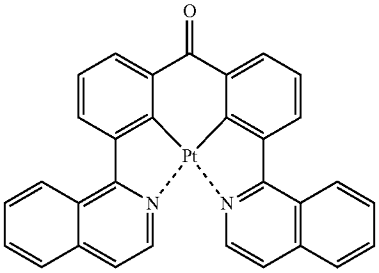
PD32
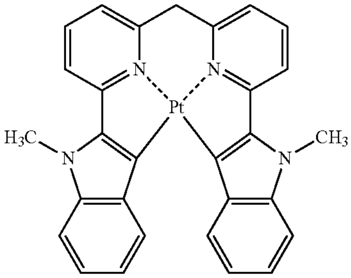
PD33
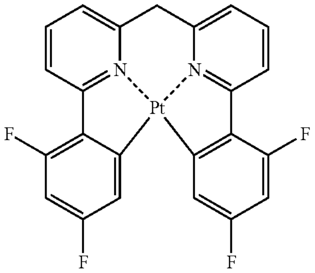
PD34
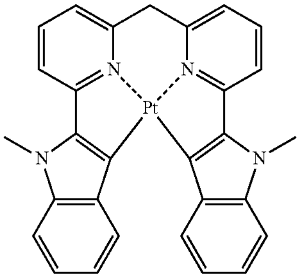
PD35
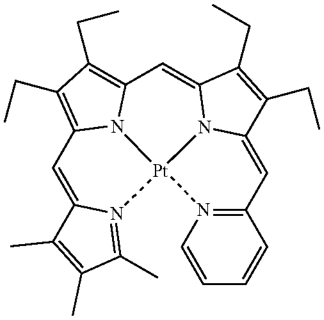

-continued
PD36
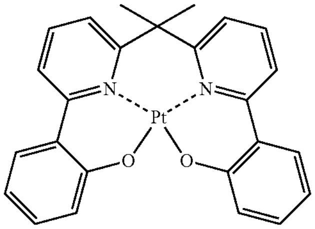
PD37
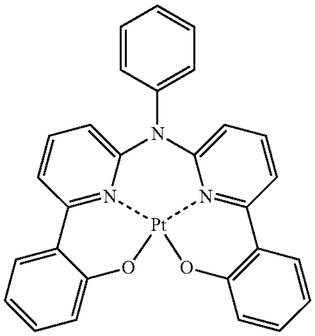
PD38
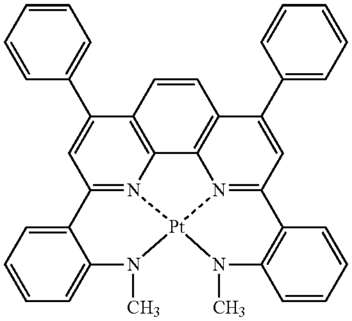
PD39
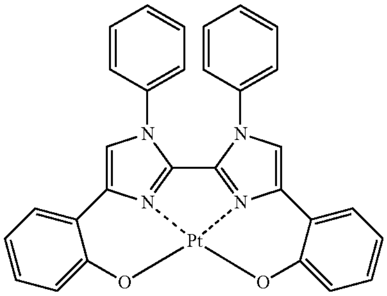
PD40
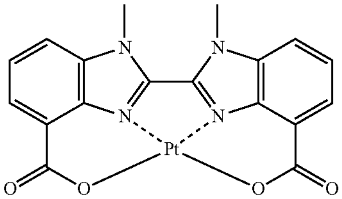
PD41
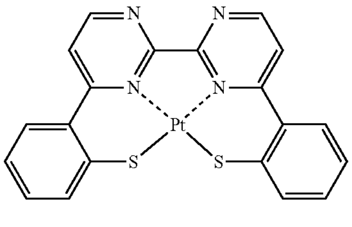
-continued
PD-42
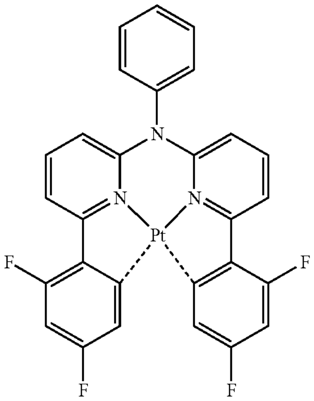
PD-43
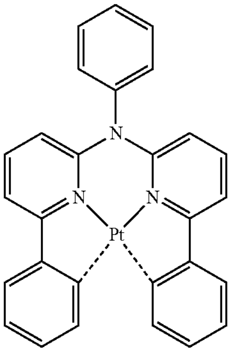
PD-44
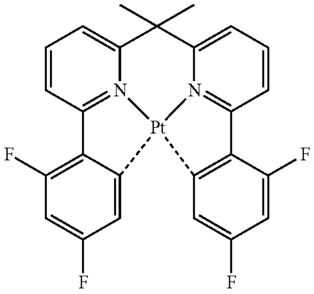
PD-45
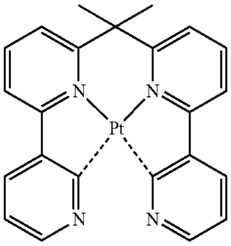
PD46
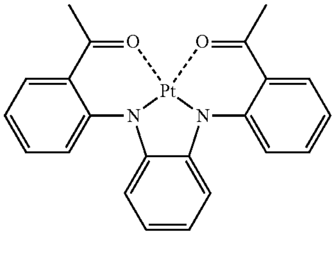

-continued
PD47
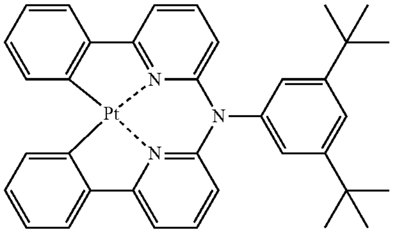
PD48
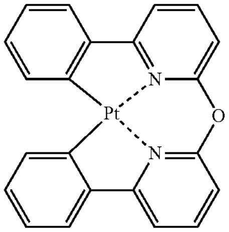
PD49
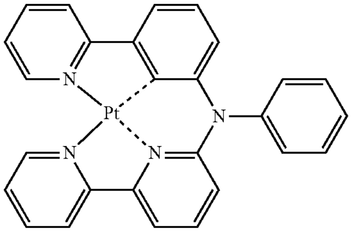
PD50
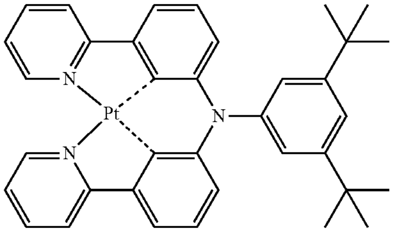
PD51
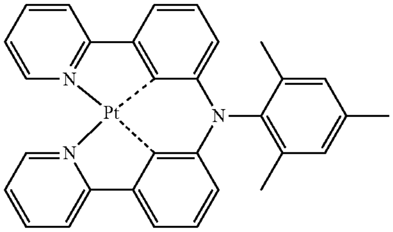
PD52
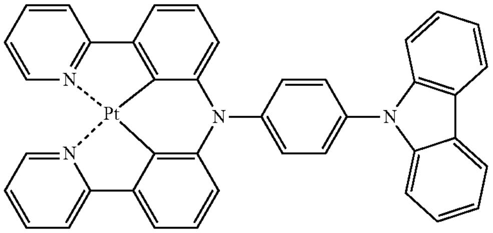
-continued
PD53
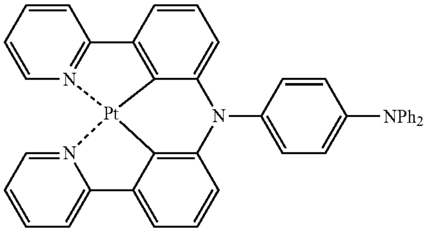
PD54
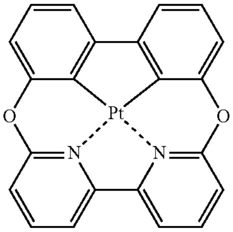
PD55
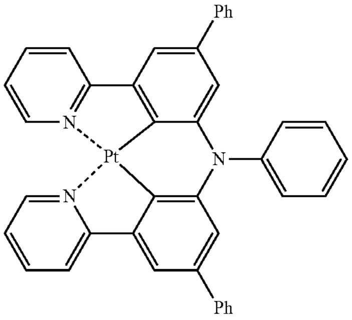
PD56
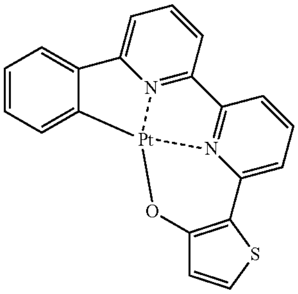
PD57
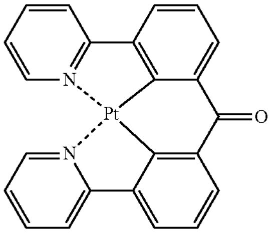

-continued
PD58
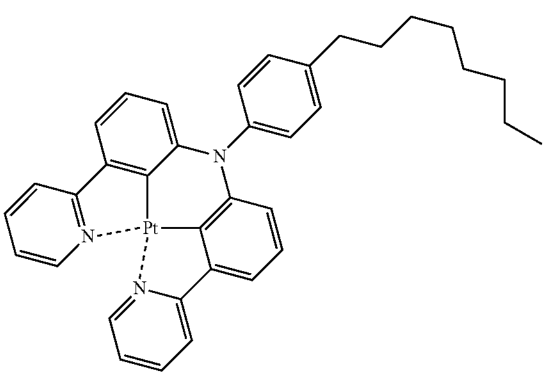
PD59
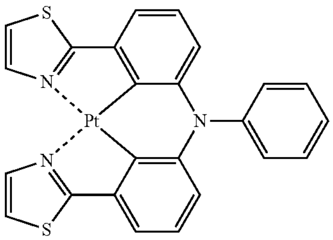
PD60
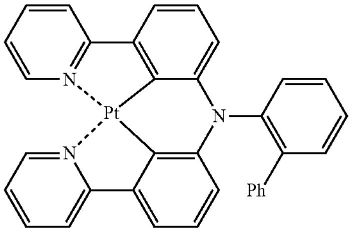
PD61
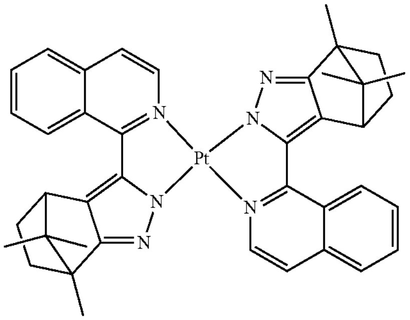
PD62
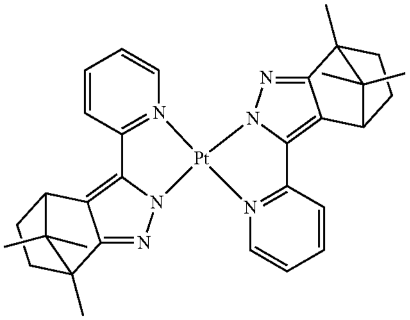
-continued
PD63
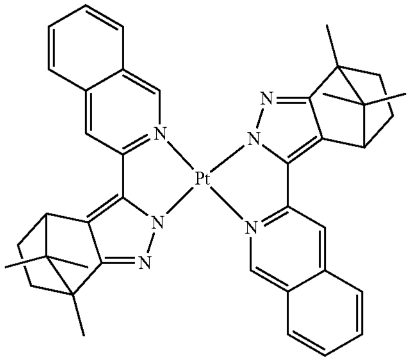
PD64
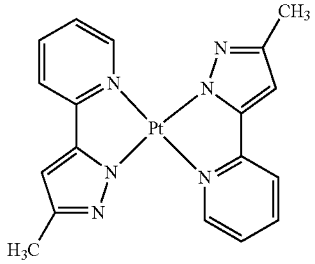
PD65
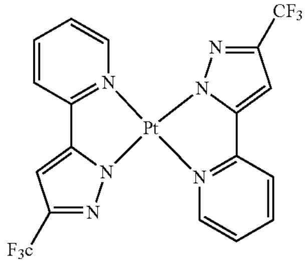
PD66
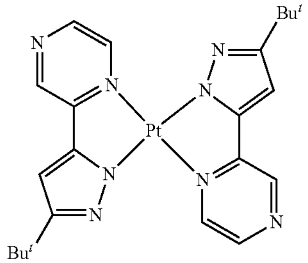
PD67
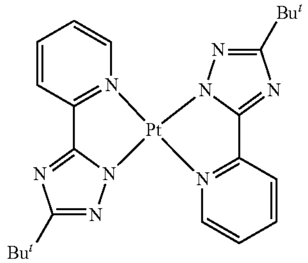

-continued

PD68

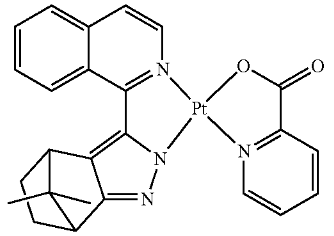

PD69

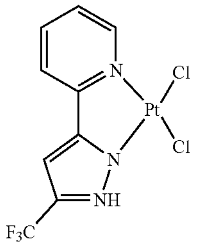

PD70

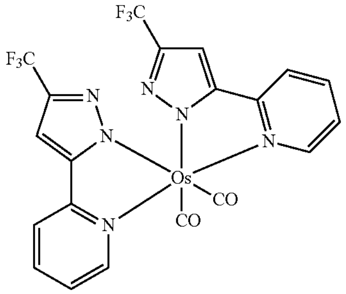

PD71

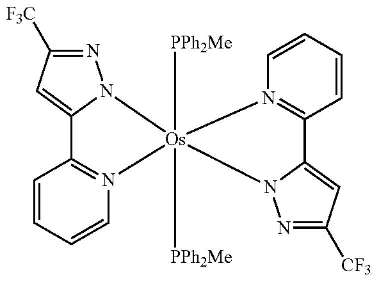

PD72

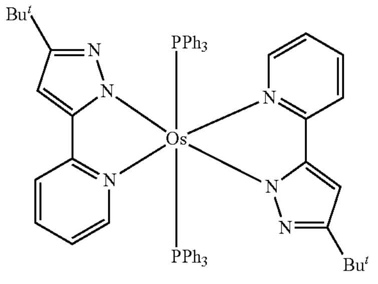

PD73

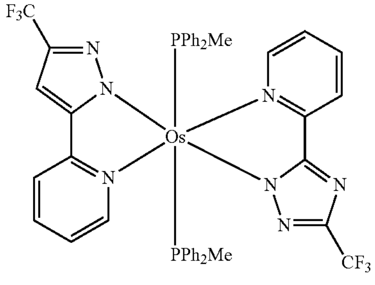

-continued

PD74

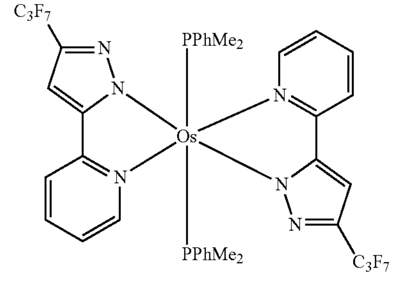

PD75

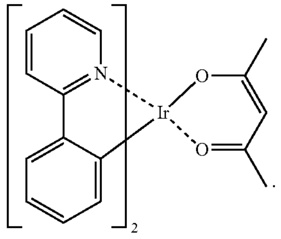

The fluorescent dopant may include a compound represented by Formula 501:

Formula 501

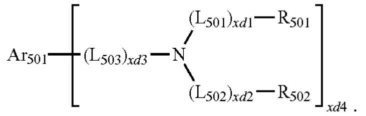

In Formula 501, $Ar_{501}$ may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group; and a naphthalene group, a heptalene group, a fluorene group, spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, each substituted with at least one selected from deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) (where $Q_{501}$ to $Q_{503}$ may be each independently selected from hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group), descriptions of $L_{501}$ to $L_{503}$ may be each understood by referring to the description of $L_1$ in the present specification, $R_{501}$ and $R_{502}$ may be each independently selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, xd1 to xd3 may be each independently selected from 0, 1, 2, and 3, and xd4 may be selected from 1, 2, 3, and 4.

The fluorescent dopant may include at least one of Compounds FD1 to FD9:

FD1

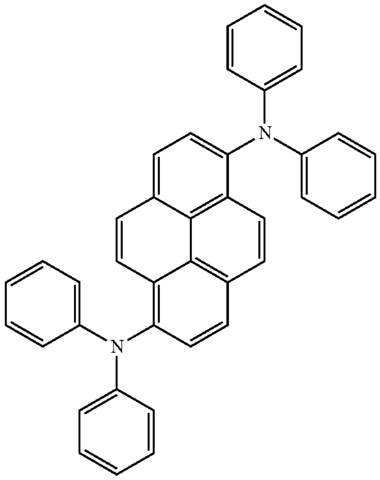

-continued

FD2

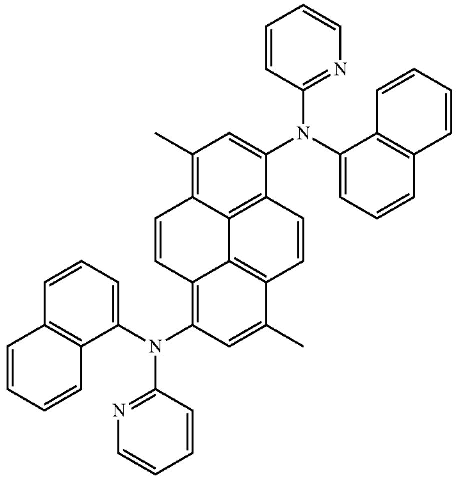

FD3

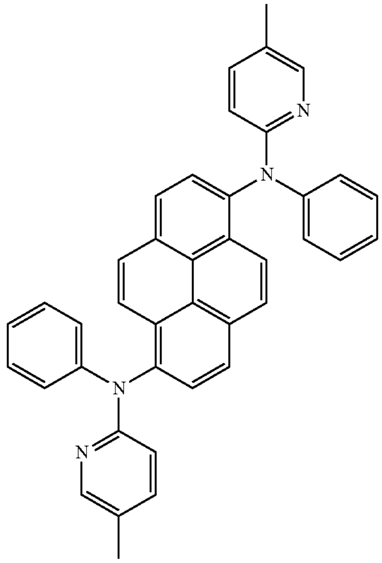

FD4

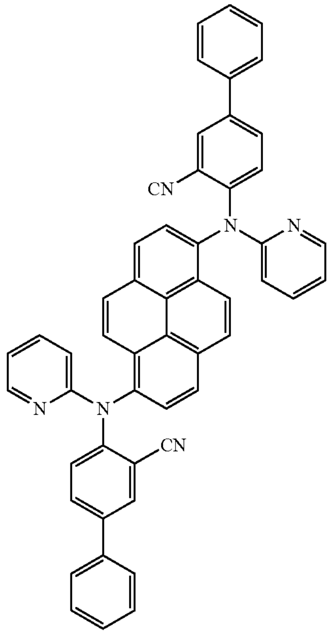

-continued

FD5

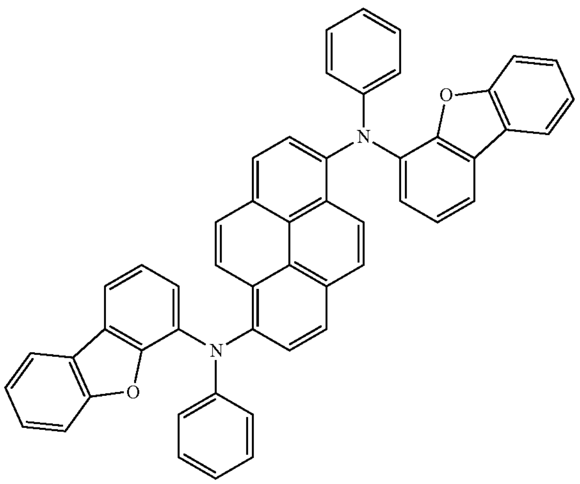

FD6

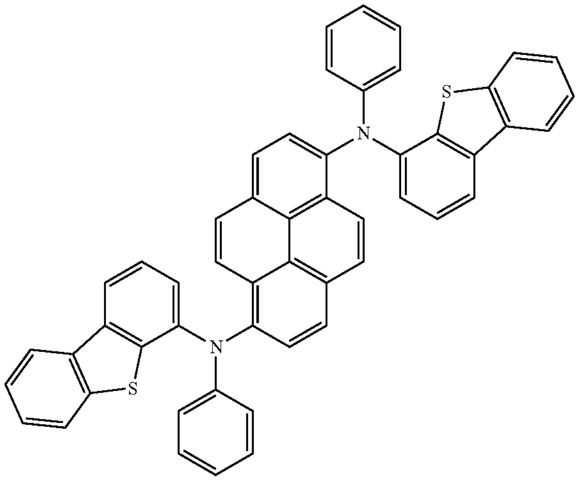

FD7

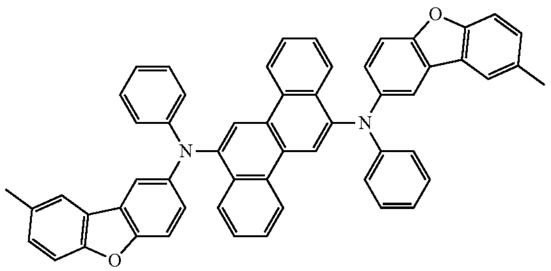

-continued

FD8

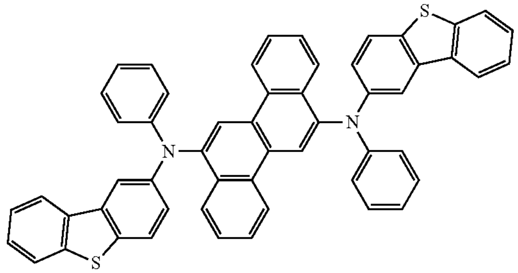

FD9

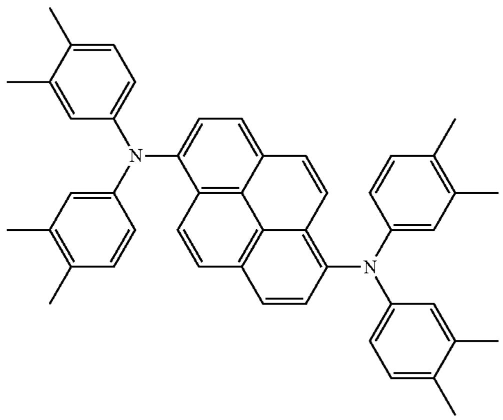

.

The amount of the dopant included in the emission layer may be in a range of about 0.01 parts by weight to about 15 parts by weight based on 100 parts by weight of the host, but the amount of the dopant is not limited thereto.

A thickness of the emission layer may be in a range of about 100 Å to about 1,000 Å, for example, about 200 Å to about 600 Å. When the thickness of the emission layer is within any of these ranges, the emission layer may have excellent (or suitable) light-emitting properties without a substantial increase in driving voltage.

In some embodiments, the fluorescent dopant may be selected from compounds below, but is not limited thereto:

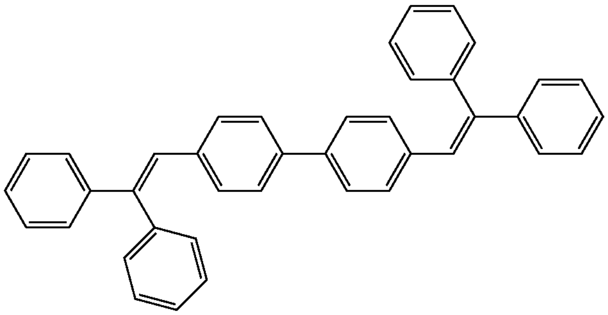
DPVBi
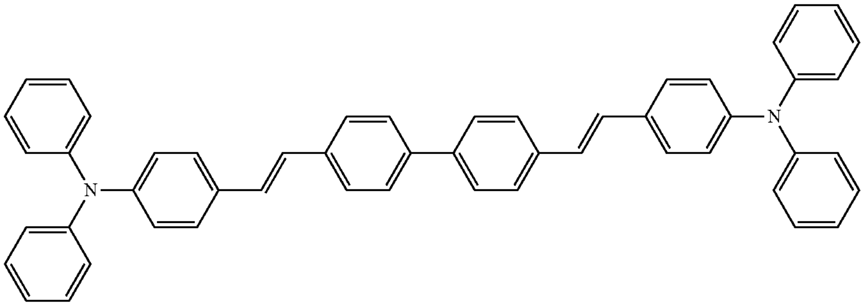
DPAVBi
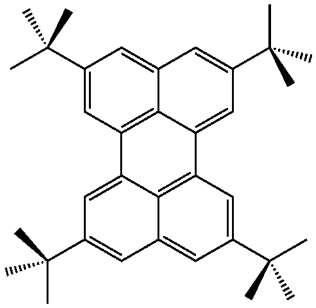
TBPe
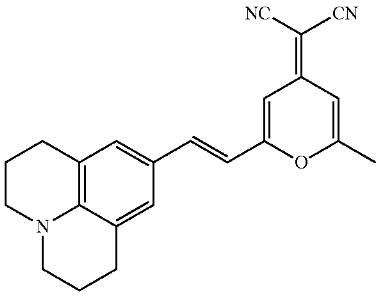
DCM
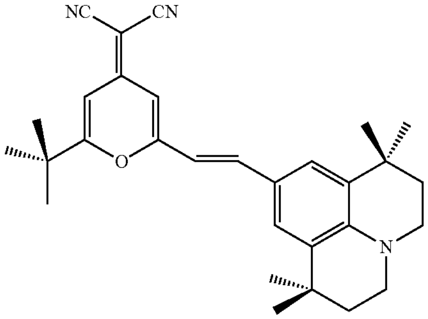
DCJTB -continued

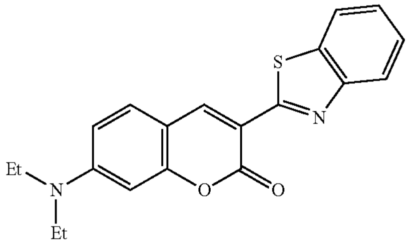

Coumarin 6

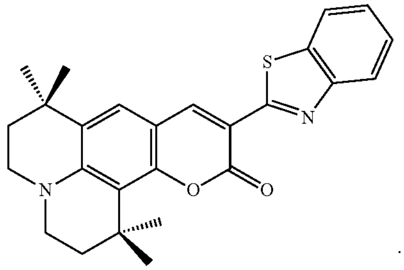

C545T

The electron transport region may be disposed on the emission layer.

The electron transport region may includean HBL, an ETL, an EIL, or any combination thereof, but embodiments are not limited thereto.

For example, the electron transport region may have a structure of ETL/EIL or a structure of HBL/ETL/EIL, wherein the layers of each structure are sequentially stacked in the stated order from the emission layer, but embodiments are not limited thereto.

According to an example embodiment, the organic layer 150 included in the organic light-emitting device 10 may include the electron transport region disposed between the emission layer and the second electrode 190.

The electron transport region may include the condensed cyclic compound of Formula 1.

When the electron transport region includes an HBL, the HBL may be formed on the emission layer by utilizing various suitable methods, such as vacuum deposition, spin coating, casting, an LB method, an ink-jet printing, a laser-printing, and/or an LITI method. When the HBL is formed by vacuum deposition and/or spin coating, the deposition and coating conditions for the HBL may be determined by referring to the deposition and coating conditions for the HIL.

The HBL may include, for example, at least one selected from BCP and Bphen below, but embodiments are not limited thereto:

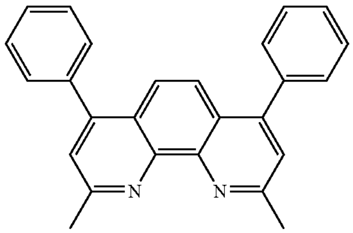

BCP

-continued

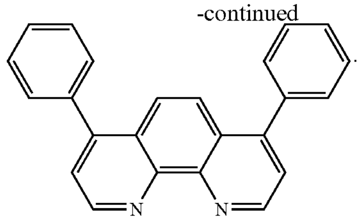

Bphen

A thickness of the HBL may be in a range of about 20 Å to about 1,000 Å, for example, about 30 Å to about 300 Å. When the thickness of the HBL is within any of these ranges, satisfactory (or suitable) hole blocking properties may be obtained without a substantial increase in driving voltage.

The electron transport region may include an ETL. The ETL may be formed on the emission layer or on the HBL by utilizing various suitable methods, such as vacuum deposition, spin coating, casting, an LB method, an ink-jet printing, a laser-printing, and/or an LITI method. When the ETL is formed by vacuum deposition and/or spin coating, the deposition and coating conditions for the ETL may be determined by referring to the deposition and coating conditions for the HIL.

The ETL may include the condensed cyclic compound of Formula 1.

A thickness of the ETL may be in a range of about 100 Å to about 1,000 Å, for example, about 150 Å to about 500 Å. When the thickness of the ETL is within any of these ranges, satisfactory (or suitable) electron transporting properties may be obtained without a substantial increase in driving voltage.

The ETL may further include, in addition to the materials described above, a metal-containing material.

The metal-containing material may include a Li complex. The Li complex may include, for example, Compound ET-D1 (8-hydroxyquinolinolato-lithium, LiQ) and/or Compound ET-D2:

ET-D1

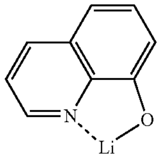

ET-D2

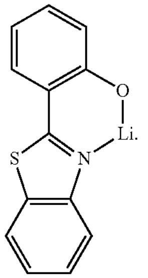

The electron transport region may include an EIL that facilitates electron injection from the second electrode 190.

The EIL may be formed on the ETL by utilizing various suitable methods, such as vacuum deposition, spin coating, casting, an LB method, an ink-jet printing, a laser-printing, and/or an LITI method. When the EIL is formed by vacuum deposition and/or spin coating, the deposition and coating conditions for the EIL may be determined by referring to the deposition and coating conditions for the HIL.

The EIL may include at least one selected from LiF, NaCl, CsF, $Li_2O$, BaO, and LiQ.

A thickness of the EIL may be in a range of about 1 Å to about 100 Å, for example, about 3 Å to about 90 Å. When the thickness of the EIL is within any of these ranges, satisfactory (or suitable) electron injecting properties may be obtained without a substantial increase in driving voltage.

The second electrode 190 may be disposed on the organic layer 150. The second electrode 190 may be a cathode that is an electron injection electrode. In this regard, a material for forming the second electrode 190 may be a material having a low work function, and non-limiting examples thereof include a metal, an alloy, an electrically conductive compound, and a mixture thereof, each with a low work function. For example, the material for forming the second electrode 190 may include lithium (Li), magnesium (Mg), aluminum (Al), aluminum-lithium (Al—Li), calcium (Ca), magnesium-indium (Mg—In), and/or magnesium-silver (Mg—Ag). In some embodiments, the material for forming the second electrode 190 may be ITO and/or IZO. The second electrode 190 may be a semi-transparent electrode or a transparent electrode.

Figure 2:
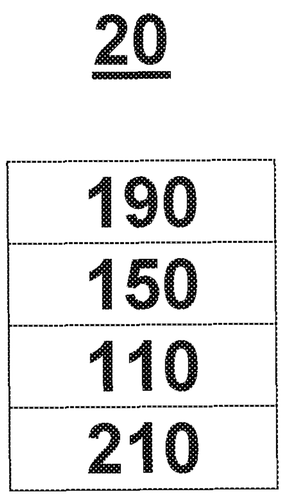
FIG. 2 is a diagram schematically illustrating an organic light-emitting device according to another example embodiment of the present disclosure.
Figure 3:
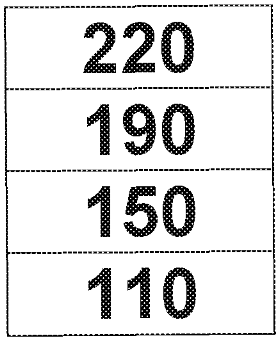
FIG. 3 is a diagram schematically illustrating an organic light-emitting device according to another example embodiment of the present disclosure.
Figure 4:
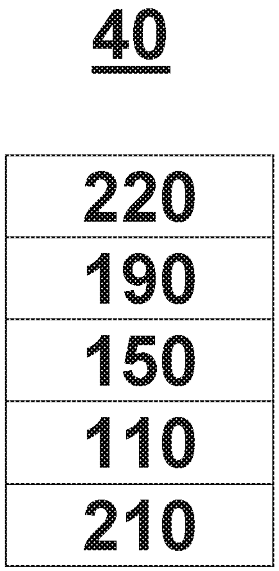
FIG. 4 is a diagram schematically illustrating an organic light-emitting device according to another example embodiment of the present disclosure.

FIG. 2 is a schematic diagram of a structure of an organic light-emitting device 20 in which a first capping layer 210, the first electrode 110, the organic layer 150, and the second electrode 190 are sequentially stacked, FIG. 3 is a schematic diagram of a structure of an organic light-emitting device 30 in which the first electrode 110, the organic layer 150, the second electrode 190, and a second capping layer 220 are sequentially stacked, and FIG. 4 is a schematic diagram of a structure of an organic light-emitting device 40 in which the first capping layer 210, the first electrode 110, the organic layer 150, the second electrode 190, and the second capping layer 220 are sequentially stacked.

In FIGS. 2 to 4, descriptions of the first electrode 110, the organic layer 150, and the second electrode 190 may be understood by referring to the descriptions thereof provided in connection with FIG. 1 of the present specification.

Light generated from the emission layer included in the organic layer 150 of the organic light-emitting device 20 or 40 may be extracted (e.g., directed) to the outside via the first electrode 110 (which may be a semi-transparent electrode or a transparent electrode) and the first capping layer 210. Meanwhile, light generated from the emission layer included in the organic layer 150 of the organic light-emitting device 30 or 40 may be extracted to the outside via the second electrode 190 (which may be a semi-transparent electrode or a transparent electrode) and the second capping layer 220.

The first capping layer 210 and the second capping layer 220 may each serve to improve the external light emission efficiency according to a constructive interference principle.

The first capping layer 210 shown in FIG. 2 and the second capping layer 220 shown in FIG. 3 may each include the condensed cyclic compound of Formula 1.

At least one of the first capping layer 210 and the second capping layer 220 shown in FIG. 4 may include the condensed cyclic compound of Formula 1.

In some embodiments, when the condensed cyclic compound of Formula 1 is included in the first capping layer 210 and/or the second capping layer 220, the organic layer 150 shown in FIGS. 2 to 4 may not include the condensed cyclic compound of Formula 1.

Hereinbefore, the organic light-emitting device 10 has been described with reference to FIGS. 1 to 4, but embodiments of the present disclosure are not limited thereto.

A $C_1$-$C_{60}$ alkyl group as used herein may refer to a linear or branched aliphatic hydrocarbon monovalent group having 1 to 60 carbon atoms, and non-limiting examples thereof include a methyl group, an ethyl group, a propyl group, an isobutyl group, a sec-butyl group, a ter-butyl group, a pentyl group, an iso-amyl group, and a hexyl group. A $C_1$-$C_{60}$ alkylene group as used herein may refer to a divalent group having the same structure as the $C_1$-$C_{60}$ alkyl group.

A $C_1$-$C_{60}$ alkoxy group as used herein may refer to a monovalent group represented by —$OA_{101}$ (where $A_{101}$ is the $C_1$-$C_{60}$ alkyl group), and non-limiting examples thereof include a methoxy group, an ethoxy group, and an isopropoxy group.

A $C_2$-$C_{60}$ alkenyl group as used herein may refer to a hydrocarbon group having at least one carbon-carbon double bond at one or more positions along a hydrocarbon chain of the $C_2$-$C_{60}$ alkyl group (e.g., in the middle or at either terminal end of the $C_2$-$C_{60}$ alkyl group), and non-limiting examples thereof include an ethenyl group, a propenyl group, and a butenyl group. A $C_2$-$C_{60}$ alkenylene group as used herein may refer to a divalent group having the same structure as the $C_2$-$C_{60}$ alkenyl group.

A $C_2$-$C_{60}$ alkynyl group as used herein may refer to a hydrocarbon group having at least one carbon-carbon triple bond at one or more positions along a hydrocarbon chain of the $C_2$-$C_{60}$ alkyl group (e.g., in the middle or at either terminal end of the $C_2$-$C_{60}$ alkyl group), and non-limiting examples thereof include an ethynyl group and a propynyl group. A $C_2$-$C_{60}$ alkynylene group as used herein may refer to a divalent group having the same structure as the $C_2$-$C_{60}$ alkynyl group.

A $C_3$-$C_{10}$ cycloalkyl group as used herein may refer to a monovalent hydrocarbon monocyclic saturated group having 3 to 10 carbon atoms, and non-limiting examples thereof include a cyclopropyl group, a cyclobutyl group, a cyclopentyl group, a cyclohexyl group, and a cycloheptyl group.

A $C_3$-$C_{10}$ cycloalkylene group as used herein may refer to a divalent group having the same structure as the $C_3$-$C_{10}$ cycloalkyl group.

A $C_1$-$C_{10}$ heterocycloalkyl group as used herein may refer to a monovalent monocyclic group having at least one heteroatom selected from N, O, P, Si and S as a ring-forming atom and 1 to 10 carbon atoms, and non-limiting examples thereof include a tetrahydrofuranyl group and a tetrahydrothiophenyl group. A $C_1$-$C_{10}$ heterocycloalkylene group as used herein may refer to a divalent group having the same structure as the $C_1$-$C_{10}$ heterocycloalkyl group.

A $C_3$-$C_{10}$ cycloalkenyl group as used herein may refer to a monovalent monocyclic group that has 3 to 10 carbon atoms and at least one double bond in the ring thereof and does not have aromaticity (e.g., the ring is not aromatic), and non-limiting examples thereof include a cyclopentenyl group, a cyclohexenyl group, and a cycloheptenyl group. A $C_3$-$C_{10}$ cycloalkenylene group as used herein may refer to a divalent group having the same structure as the $C_3$-$C_{10}$ cycloalkenyl group.

A $C_1$-$C_{10}$ heterocycloalkenyl group as used herein may refer to a monovalent monocyclic group that has at least one heteroatom selected from N, O, P, Si, and S as a ring-forming atom, 1 to 10 carbon atoms, and at least one double bond in the ring. Non-limiting examples of the $C_1$-$C_{10}$ heterocycloalkenyl group include a 2,3-dihydrofuranyl group and a 2,3-dihydrothiophenyl group. A $C_1$-$C_{10}$ heterocycloalkenylene group as used herein may refer to a divalent group having the same structure as the $C_1$-$C_{10}$ heterocycloalkenyl group.

A $C_6$-$C_{60}$ aryl group as used herein may refer to a monovalent group having a carbocyclic aromatic system having 6 to 60 carbon atoms, and a $C_6$-$C_{60}$ arylene group as used herein may refer to a divalent group having a carbocyclic aromatic system having 6 to 60 carbon atoms. Non-limiting examples of the substituted or unsubstituted $C_6$-$C_{60}$ aryl group include a phenyl group, a biphenyl group, a terphenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each independently include two or more rings, the respective rings may be fused to each other or may be linked with each other via a single bond.

A $C_1$-$C_{60}$ heteroaryl group as used herein may refer to a monovalent group having a cyclic aromatic system that has at least one heteroatom selected from N, 0, Si, P, and S as a ring-forming atom, and 1 to 60 carbon atoms. A $C_1$-$C_{60}$ heteroarylene group as used herein may refer to a divalent group having a carbocyclic aromatic system that has at least one heteroatom selected from N, O, P, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each independently include two or more rings, the respective rings may be fused to each other or may be linked with each other via a single bond.

A $C_6$-$C_{60}$ aryloxy group as used herein may refer to a monovalent group represented by —$OA_{102}$ (where $A_{102}$ is the $C_6$-$C_{60}$ aryl group), and a $C_6$-$C_{60}$ arylthio group as used herein may refer to a monovalent group represented by —$SA_{103}$ (where $A_{103}$ is the $C_6$-$C_{60}$ aryl group).

A monovalent non-aromatic condensed polycyclic group as used herein may refer to a monovalent group that has two or more rings condensed (e.g., fused) to each other, has only carbon atoms as ring-forming atoms (e.g., 8 to 60 carbon atoms), and has non-aromaticity in the entire molecular structure (e.g., does not have overall aromaticity). A non-limiting example of the monovalent non-aromatic condensed polycyclic group includes a fluorenyl group. A divalent non-aromatic condensed polycyclic group as used herein may refer to a divalent group having the same structure as the monovalent non-aromatic condensed polycyclic group.

A monovalent non-aromatic condensed heteropolycyclic group as used herein may refer to a monovalent group that has two or more rings condensed (e.g., fused) to each other, has at least one heteroatom selected from N, O, Si, P, and S as a ring-forming atom, in addition to carbon atoms (e.g., 1 to 60 carbon atoms), and has non-aromaticity in the entire molecular structure (e.g., does not have overall aromaticity). A non-limiting example of the monovalent non-aromatic condensed heteropolycyclic group includes a carbozolyl group. A divalent non-aromatic condensed heteropolycyclic group as used herein may refer to a divalent group having the same structure as the monovalent non-aromatic condensed heteropolycyclic group.

In the present specification, at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{26})$, and —$B(Q_{26})(Q_{27})$; and —$N(Q_{31})(Q_{32})$, —$Si(Q_{33})(Q_{34})(Q_{35})$, and —$B(Q_{36})(Q_{37})$, where $Q_{11}$ to $Q_{17}$, $Q_{21}$ to $Q_{27}$, and $Q_{31}$ to $Q_{37}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

The term "biphenyl group" as used herein may refer to a monovalent group in which two benzene rings are linked together via a single bond, and the term "terphenyl group" as used herein may refer to a monovalent group in which three benzene rings are linked together via a single bond.

The term "Ph" as used herein may refer to a phenyl group, the term "Me" as used herein may refer to a methyl group, the term "Et" as used herein may refer to an ethyl group, and the term "ter-Bu" or "Bu$^t$" as used herein may refer to a tert-butyl group.

Hereinafter, an organic light-emitting device according to one or more embodiments of the present inventive concept will be described in more detail with reference to Synthesis Examples and Examples. The expression "B was used instead of A" used in describing Synthesis Examples may refer to a molar equivalent of A being identical to a molar equivalent of B. The expression "eq" may refer to a molar equivalent.

EXAMPLES

Synthesis of Intermediate-1 (Int-1)

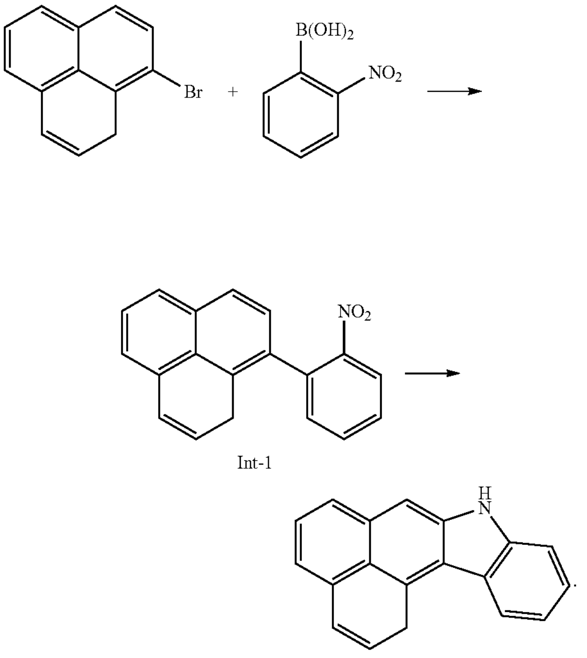

Int-1

Int-2

9-bromo-1H-phenalene (1 eq), (2-nitrophenyl)boronic acid (1.2 eq), $Pd(PPh_3)_4$ (0.02 eq), and $Na_2CO_3$ (1.2 eq) were mixed with a mixture of toluene, distilled water, and ethanol (0.1M) (mixed at a ratio of 5:3:2), and then, the mixed solution was stirred under reflux for 12 hours. The resulting solution was cooled to room temperature, subjected to an extraction process using methylene chloride (MC), and washed with distilled water. The resulting products obtained therefrom were dried by using magnesium sulfate ($MgSO_4$) and distilled under reduced pressure, and then, the resulting products were purified by column chromatography, thereby obtaining Intermediate-1 (Int-1, yield: 79.2%). Int-1 was identified by performing elemental analysis and High-resolution mass spectrometry (HRMS).

Elemental Analysis for $C_{19}H_{13}NO_2$ calcd: C, 79.43; H, 4.56; N, 4.88; 0, 11.14.

HRMS for $C_{19}H_{13}NO_2$ [M]+: calcd: 287.32. found: 286.

Synthesis of Intermediate-2 (Int-2)

5 g of Intermediate-1 (Int-1) was dissolved in 15 g of triethylphosphite, and then, the mixed solution was stirred under reflux for 12 hours in a nitrogen atmosphere. After the completion of the reaction, the resulting solution was subjected to vacuum distillation to remove remaining triethylphosphite, and the resulting products were purified by column chromatography (using hexane:MC=4:1 (v/v)), thereby obtaining Intermediate-2 (Int-2, yield: 46.5%). Int-2 was identified by performing elemental analysis and HRMS.

Elemental Analysis for $C_{19}H_{13}N$ calcd: C, 89.38; H, 5.13; N, 5.49.

HRMS for $C_{19}H_{13}N$ [M]+: calcd: 255.32. found: 254.

Synthesis Example 1: Synthesis of Compound 1

1

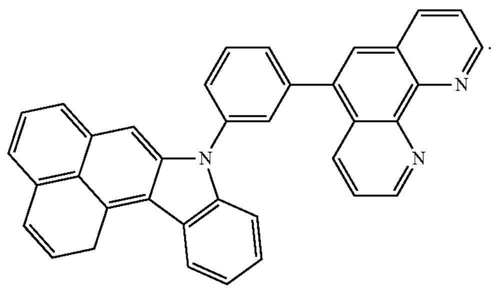

Pd(dba)$_3$ (0.03 eq), (t-Bu)$_3$P (0.06 eq), and toluene (0.1M) were added to a flask containing Int-2 (1 eq) and 5-(3-bromophenyl)-1,10-phenanthroline (1.2 eq), and then, the mixed solution was stirred under reflux for 12 hours. The resulting solution was cooled to room temperature, and then subjected to an extraction process using MC, and washed with distilled water. The resulting products obtained therefrom were dried by using $MgSO_4$, and distilled under reduced pressure, and then, the resulting products were purified by column chromatography, thereby obtaining Compound 1 (yield: 86.4%). Compound 1 was identified by performing elemental analysis and HRMS.

Elemental Analysis for $C_{37}H_{23}N_3$ calcd: C, 87.20; H, 4.55; N, 8.25.

HRMS for $C_{37}H_{23}N_3$ [M]+: calcd: 509.61. found: 508.

Synthesis Example 2: Synthesis of Compound 3

3

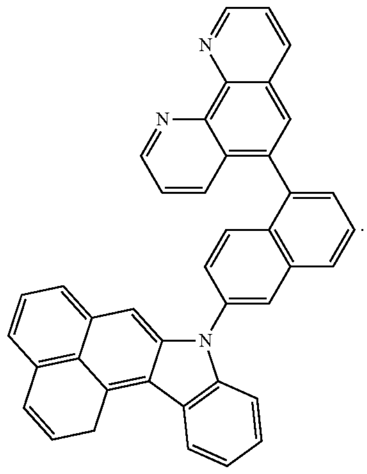

Compound 3 (yield: 71%) was synthesized in the same (or substantially the same) manner as in Synthesis Example 1, except that 5-(6-bromonaphthalen-1-yl)-1,10-phenanthroline was used instead of 5-(3-bromophenyl)-1,10-phenanthroline. Compound 3 was identified by performing elemental analysis and HRMS.

Elemental Analysis for $C_{41}H_{25}N_3$ calcd: C, 87.99; H, 4.50; N, 7.51.

HRMS for $C_{41}H_{25}N_3$ [M]+: calcd: 559.67. found: 558.

Synthesis Example 3: Synthesis of Compound 5

5

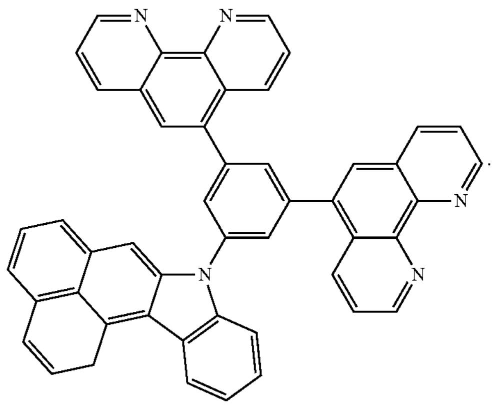

Compound 5 (yield: 82.6%) was synthesized in the same (or substantially the same) manner as in Synthesis Example 1, except that 5,5'-(5-bromo-1,3-phenylene)bis(1,10-phenanthroline) was used instead of 5-(3-bromophenyl)-1,10-phenanthroline. Compound 5 was identified by performing elemental analysis and HRMS.

Elemental Analysis for $C_{49}H_{29}N_5$ calcd: C, 85.57; H, 4.25; N, 10.18.

HRMS for $C_{49}H_{29}N_5$ [M]+: calcd: 687.81. found: 686.

Synthesis Example 4: Synthesis of Compound 7

7

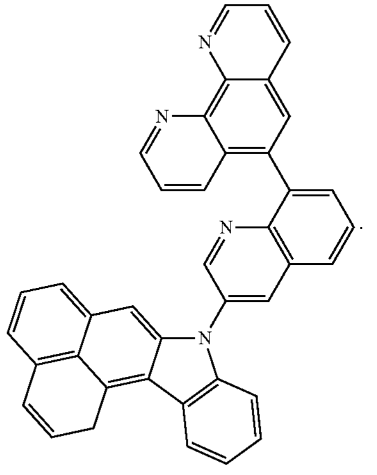

Compound 7 (yield: 77.4%) was synthesized in the same (or substantially the same) manner as in Synthesis Example 1, except that 5-(3-bromoquinolin-8-yl)-1,10-phenanthroline was used instead of 5-(3-bromophenyl)-1,10-phenanthroline. Compound 7 was identified by performing elemental analysis and HRMS.

Elemental Analysis for $C_{40}H_{24}N_4$ calcd: C, 85.69; H, 4.31; N, 9.99.

HRMS for $C_{40}H_{24}N_4$ [M]+: calcd: 560.66. found: 559.

Synthesis Example 5: Synthesis of Compound 9

9

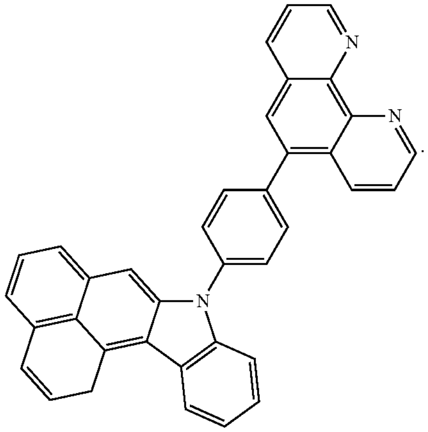

Compound 9 (yield: 84.7%) was synthesized in the same (or substantially the same) manner as in Synthesis Example 1, except that 5-(4-bromophenyl)-1,10-phenanthroline was used instead of 5-(3-bromophenyl)-1,10-phenanthroline. Compound 9 was identified by performing elemental analysis and HRMS.

Elemental Analysis for $C_{37}H_{23}N_3$ calcd: C, 87.20; H, 4.55; N, 8.25.

HRMS for $C_{37}H_{23}N_3$ [M]+: calcd: 509.61. found: 508.

Synthesis Example 6: Synthesis of Compound 20

20

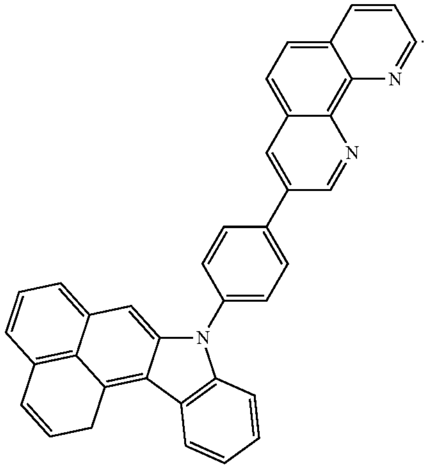

Compound 20 (yield: 71.4%) was synthesized in the same (or substantially the same) manner as in Synthesis Example 1, except that 3-(4-bromophenyl)-1,10-phenanthroline was used instead of 5-(3-bromophenyl)-1,10-phenanthroline. Compound 20 was identified by performing elemental analysis and HRMS.

Elemental Analysis for $C_{37}H_{23}N_3$ calcd: C, 87.20; H, 4.55; N, 8.25.

HRMS for $C_{37}H_{23}N_3$ [M]+: calcd: 509.61. found: 508.

Synthesis Example 7: Synthesis of Compound 22

22

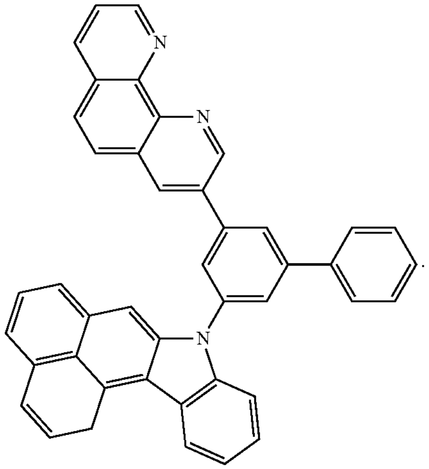

Compound 22 (yield: 77.1%) was synthesized in the same (or substantially the same) manner as in Synthesis Example 1, except that 3-(5-bromo-[1,1'-biphenyl]-3-yl)-1,10-phenanthroline was used instead of 5-(3-bromophenyl)-1,10-phenanthroline. Compound 22 was identified by performing elemental analysis and HRMS.

Elemental Analysis for $C_{43}H_{27}N_3$ calcd: C, 88.18; H, 4.65; N, 7.17.

HRMS for $C_{43}H_{27}N_3$ [M]+: calcd: 585.71. found: 584.

Synthesis Example 8: Synthesis of Compound 24

24

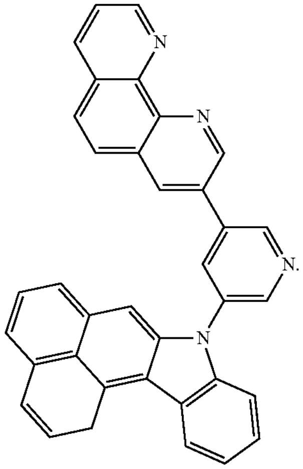

Compound 24 (yield: 72%) was synthesized in the same (or substantially the same) manner as in Synthesis Example 1, except that 3-(5-bromopyridin-3-yl)-1,10-phenanthroline was used instead of 5-(3-bromophenyl)-1,10-phenanthroline. Compound 24 was identified by performing elemental analysis and HRMS.

Elemental Analysis for $C_{36}H_{22}N_4$ calcd: C, 84.68; H, 4.34; N, 10.97.

HRMS for $C_{36}H_{22}N_4$ [M]+: calcd: 510.60. found: 509.

Synthesis Example 9: Synthesis of Compound 26

26

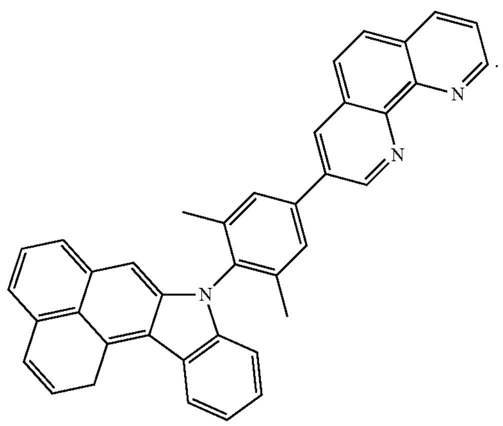

Compound 26 (yield: 73%) was synthesized in the same (or substantially the same) manner as in Synthesis Example 1, except that 3-(4-bromo-3,5-dimethylphenyl)-1,10-phenanthroline was used instead of 5-(3-bromophenyl)-1,10-phenanthroline. Compound 26 was identified by performing elemental analysis and HRMS.

Elemental Analysis for $C_{39}H_{27}N_3$ calcd: C, 87.12; H, 5.06; N, 7.82.

HRMS for $C_{39}H_{27}N_3$ [M]+: calcd: 537.67. found: 536.

Synthesis Example 10: Synthesis of Compound 28

28

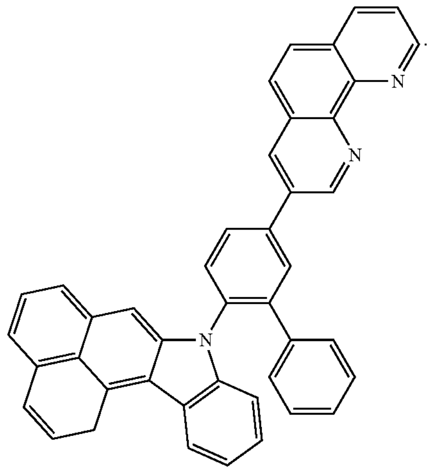

Compound 28 (yield: 72.6%) was synthesized in the same (or substantially the same) manner as in Synthesis Example 1, except that 3-(6-bromo-[1,1'-biphenyl]-3-yl)-1,10-phenanthroline was used instead of 5-(3-bromophenyl)-1,10-phenanthroline. Compound 28 was identified by performing elemental analysis and HRMS.

Elemental Analysis for $C_{43}H_{27}N_3$ calcd: C, 88.18; H, 4.65; N, 7.17.

HRMS for $C_{43}H_{27}N_3$ [M]+: calcd: 585.71. found: 584.

Synthesis Example 11: Synthesis of Compound 30

30

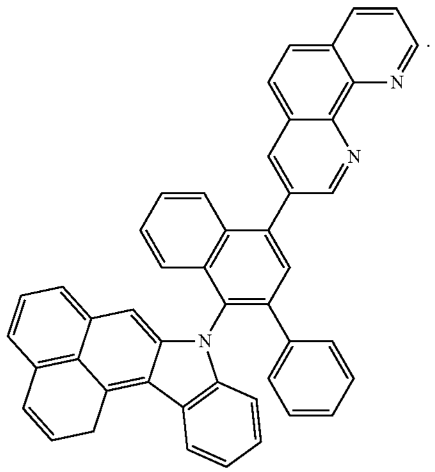

Compound 30 (yield: 72.6%) was synthesized in the same (or substantially the same) manner as in Synthesis Example 1, except that 3-(4-bromo-isoquinolin-1-yl)-1,10-phenanthroline was used instead of 5-(3-bromophenyl)-1,10-phenanthroline. Compound 30 was identified by performing elemental analysis and HRMS.

Elemental Analysis for $C_{43}H_{27}N_3$ calcd: C, 88.18; H, 4.65; N, 7.17.

HRMS for $C_{43}H_{27}N_3$ [M]+: calcd: 585.71. found: 584.

Example 1

As a substrate and an anode, a 15 $\Omega/cm^2$ (1,200 Å) glass substrate, on which an indium tin oxide (ITO) anode (manufactured by Corning, Inc.) was formed, was cut into a size of 50 mm×50 mm×0.7 mm, ultrasonically washed with isopropyl alcohol and pure water, each for 5 minutes. Afterwards, the ITO glass substrate was irradiated by UV light for 30 minutes, cleaned by exposure to ozone, and then, mounted on a vacuum depositor.

2-TNATA was vacuum-deposited on the ITO anode of the glass substrate to form an HIL having a thickness of 600 Å, and then, 4,4'-bis[N-(1-naphthyl)-N-phenylamino]biphenyl (hereinafter, referred to as NPB) was vacuum-deposited on the HIL to form an HTL having a thickness of 300 Å.

CBP (as a host) and $Ir(ppy)_3$ (as a dopant) were co-deposited at a weight ratio of 85:15 on the HTL to form an emission layer having a thickness of 300 Å.

Compound 1 was deposited on the emission layer to form an ETL having a thickness of 300 Å, and LiF was deposited on the ETL to form an EIL having a thickness of 10 Å. Then, Al was deposited on the EIL to form a cathode having a thickness of 1,200 Å, thereby manufacturing an organic light-emitting device.

Examples 2 to 14 and Comparative Examples 1 and 2

Organic light-emitting devices were manufactured in the same (or substantially the same) manner as in Example 1, except that in forming the ETL or the emission layer, compounds listed in Table 1 were respectively used instead of Compound 1 or CBP.

Evaluation Example 1

The efficiency and lifespan ($T_{95}$) of the organic light-emitting devices of Examples 1 to 14 and Comparative Examples 1 and 2 were evaluated by using a Keithley SMU 236 and a luminance meter PR650. The results are shown in Table 1. Here, the lifespan ($T_{95}$) results were obtained by measuring the time at which the luminance (@ 6,000 nit) of an organic light-emitting device was 95% of the initial luminance.

TABLE 1

| | Host in emission layer | ETL | Efficiency (cd/A) | Lifespan ($T_{95}$) (hr @ 6,000 nit) |
|---|---|---|---|---|
| Example 1 | CBP | Compound 1 | 47.3 | 970 |
| Example 2 | CBP | Compound 3 | 44.1 | 921 |
| Example 3 | CBP | Compound 5 | 45 | 943 |
| Example 4 | CBP | Compound 7 | 49.5 | 921 |
| Example 5 | CBP | Compound 9 | 50.2 | 991 |
| Example 6 | CBP | Compound 20 | 41.5 | 937 |
| Example 7 | CBP | Compound 22 | 46.8 | 897 |
| Example 8 | CBP | Compound 24 | 43.9 | 911 |
| Example 9 | CBP | Compound 26 | 46.1 | 956 |
| Example 10 | CBP | Compound 28 | 45.7 | 971 |
| Example 11 | Compound 1 | $Alq_3$ | 56.1 | 726 |
| Example 12 | Compound 5 | $Alq_3$ | 57.4 | 744 |
| Example 13 | Compound 26 | $Alq_3$ | 49.1 | 710 |
| Example 14 | Compound 30 | $Alq_3$ | 52.7 | 684 |
| Comparative Example 1 | CBP | $Alq_3$ | 39.8 | 456 |
| Comparative Example 2 | CBP | Compound A | 41.4 | 667 |

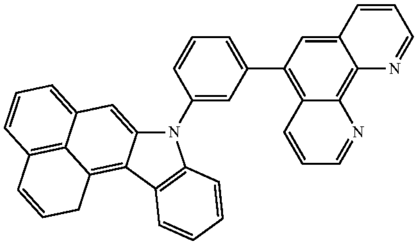

1

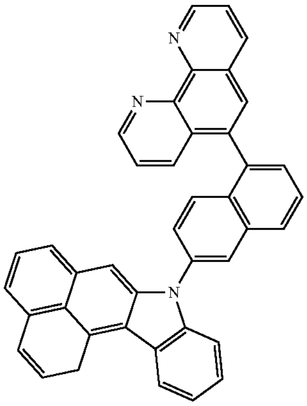

3

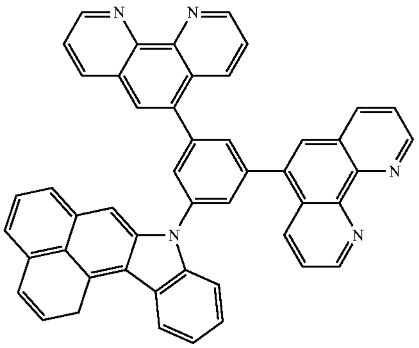

5

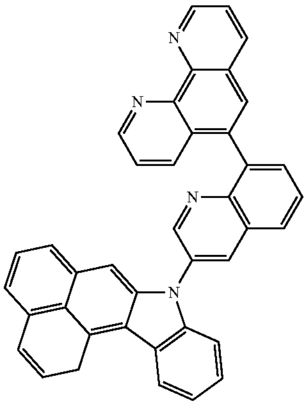

TABLE 1-continued
| Host in emission layer | ETL | Efficiency (cd/A) | Lifespan ($T_{95}$) (hr @ 6,000 nit) |
|---|---|---|---|
| 7 | 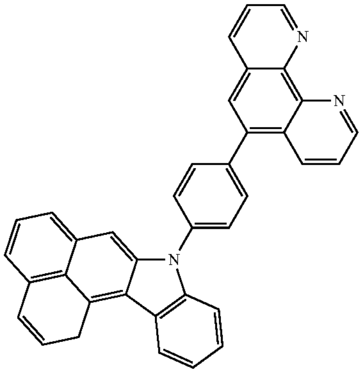 | | |
| 9 | 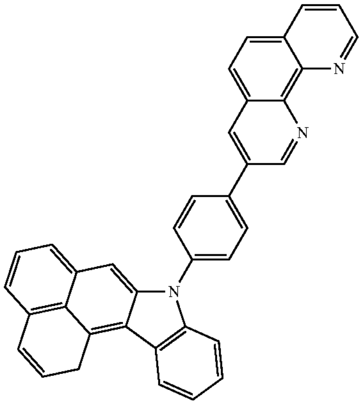 | | |
| 20 | 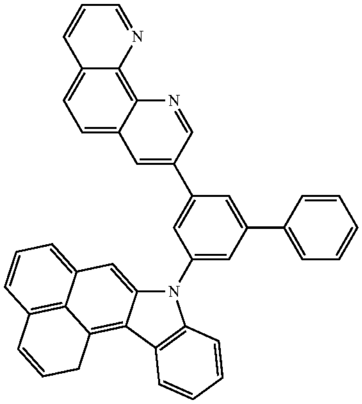 | | |
| 22 | | | |
TABLE 1-continued
| Host in emission layer | ETL | Efficiency (cd/A) | Lifespan ($T_{95}$) (hr @ 6,000 nit) |
|---|---|---|---|
| | 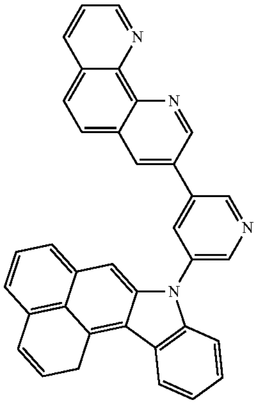 | | |
| 24 | 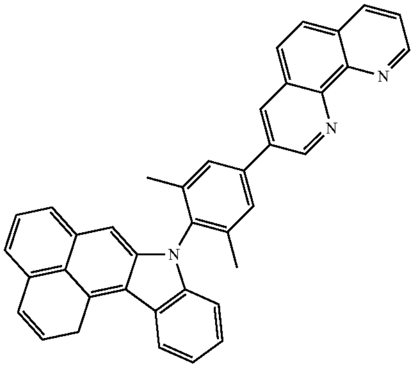 | | |
| 26 | 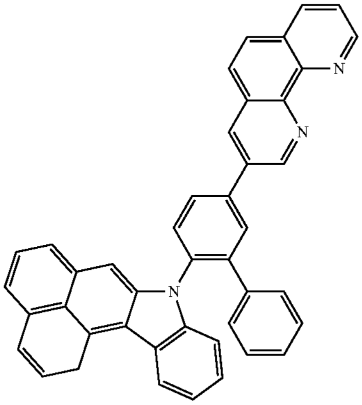 | | |
| 28 | | | |

TABLE 1-continued

| Host in emission layer | ETL | Efficiency (cd/A) | Lifespan ($T_{95}$) (hr @ 6,000 nit) |
|---|---|---|---|
| 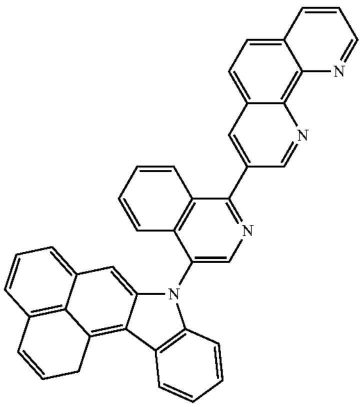 [SMILES: C1=Cc2cccc3cc4c(c(c23)C1)c1ccccc1n4-c1cnc(-c2cnc3c(ccc4cccnc43)c2)c2ccccc12] 30 | 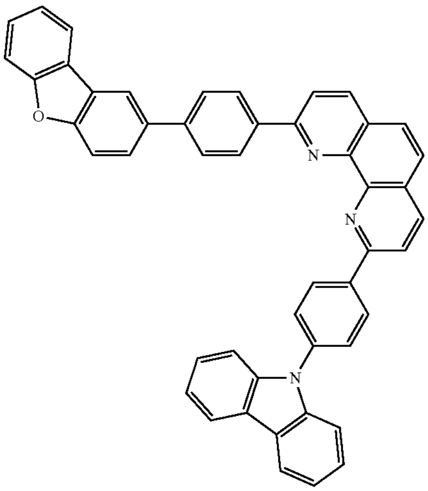 A | | |

Referring to Table 1, it can be seen that the organic light-emitting devices of Examples 1 to 10 had excellent efficiencies and lifespans compared to those of the organic light-emitting devices of Comparative Examples 1 and 2, and that the organic light-emitting devices of Examples 11 to 14 had excellent efficiencies and lifespans compared to those of the organic light-emitting device of Comparative Example 1.

As described above, according to certain embodiments, an organic light-emitting device including a condensed cyclic compound may exhibit low driving voltage, high efficiency, high luminance, and long lifespan characteristics.

As used herein, the terms “use,” “using,” and “used” may be considered synonymous with the terms “utilize,” “utilizing,” and “utilized,” respectively.

In addition, the terms “substantially,” “about,” and similar terms are used as terms of approximation and not as terms of degree, and are intended to account for the inherent deviations in measured or calculated values that would be recognized by those of ordinary skill in the art.

Also, any numerical range recited herein is intended to include all sub-ranges of the same numerical precision subsumed within the recited range. For example, a range of “1.0 to 10.0” is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

It will be further understood that the terms, such as “comprises,” “comprising,” “includes”, and/or “including”, when used in this specification, specify the presence of stated features, integers, steps, operations, elements, and/or components, but do not preclude the presence or addition of one or more other features, integers, steps, operations, elements, components, and/or groups thereof.

It should be understood that example embodiments described herein should be considered in a descriptive sense only and not for purposes of limitation. Descriptions of features or aspects within each example embodiment should typically be considered as available for other similar features or aspects in other example embodiments.

While one or more example embodiments have been described with reference to the drawings, it will be understood by those of ordinary skill in the art that various changes in form and details may be made therein without departing from the spirit and scope of the present disclosure as defined by the following claims and equivalents thereof.

What is claimed is:

1. A condensed cyclic compound represented by Formula 1:

Formula 1

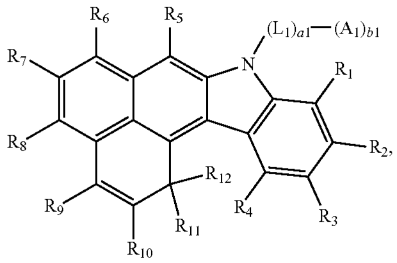

wherein, in Formula 1, $L_1$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 is 0, 1, 2, or 3, and when a1 is 2 or more, a plurality of $L_1$s are identical to or different from each other, $A_1$ is selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, b1 is 1, 2, or 3, and when b1 is 2 or more, a plurality of $A_1$s are identical to or different from each other, $R_1$ to $R_{12}$ are each independently selected from hydrogen, deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, and —$B(Q_6)(Q_7)$, and at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$, wherein $Q_1$ to $Q_7$, $Q_{11}$ to $Q_{17}$, $Q_{21}$ to $Q_{27}$, and $Q_{31}$ to $Q_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

2. The condensed cyclic compound of claim 1, wherein $L_1$ is selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —$Si(Q_{33})(Q_{34})(Q_{35})$, wherein $Q_{33}$ to $Q_{35}$ are each independently selected from a $C_1$-$C_{10}$ alkyl group, a $C_1$-$C_{10}$ alkoxy group, a phenyl group, a biphenyl group, a terphenyl group, and a naphthyl group.

3. The condensed cyclic compound of claim 1, wherein $L_1$ is selected from groups represented by Formulae 3-1 to 3-46:

Formula 3-1

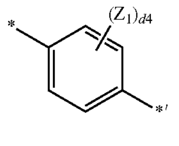

Formula 3-2

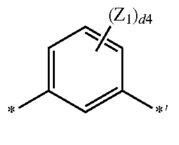

Formula 3-3

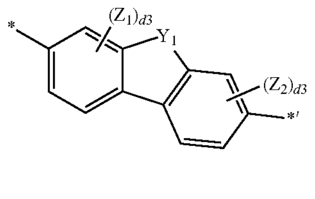

-continued
Formula 3-4
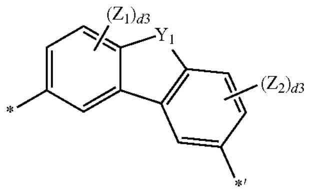
Formula 3-5
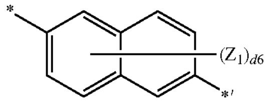
Formula 3-6
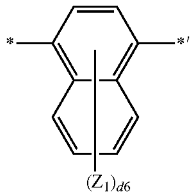
Formula 3-7
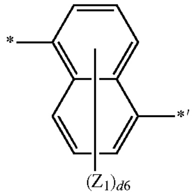
Formula 3-8
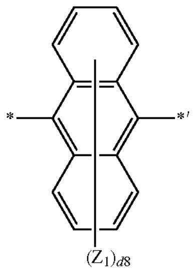
Formula 3-9
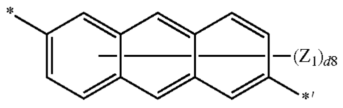
Formula 3-10
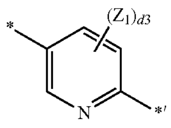
Formula 3-11
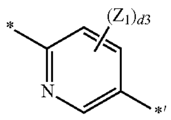
Formula 3-12
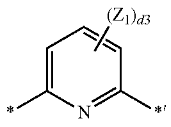
-continued
Formula 3-13
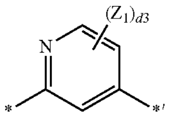
Formula 3-14
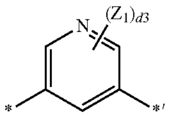
Formula 3-15
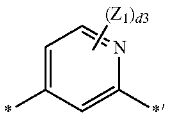
Formula 3-16
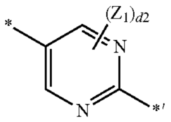
Formula 3-17
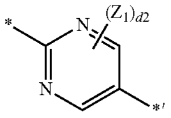
Formula 3-18
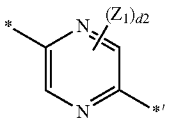
Formula 3-19
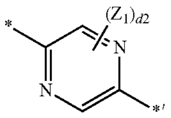
Formula 3-20
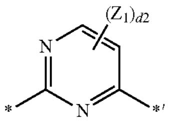
Formula 3-21
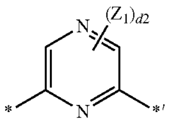
Formula 3-22
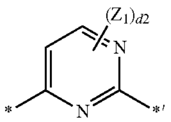
Formula 3-23
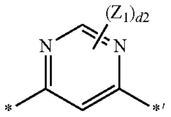
Formula 3-24
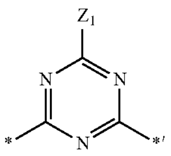

-continued
Formula 3-25
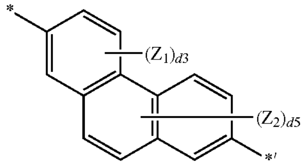
Formula 3-26
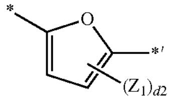
Formula 3-27
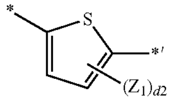
Formula 3-28
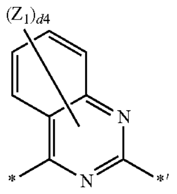
Formula 3-29
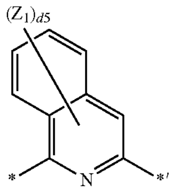
Formula 3-30
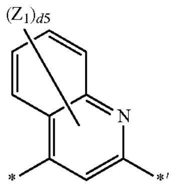
Formula 3-31
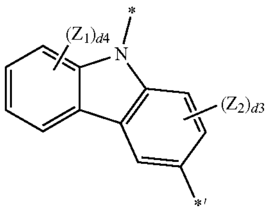
Formula 3-32
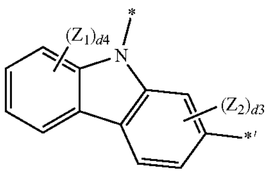
Formula 3-33
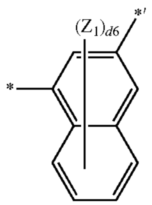
-continued
Formula 3-34
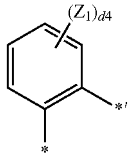
Formula 3-35
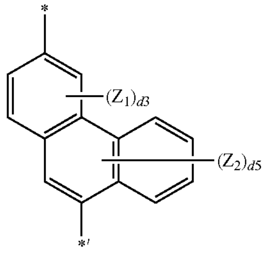
Formula 3-36
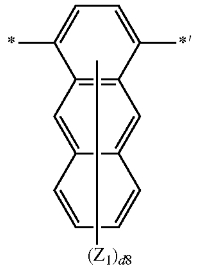
Formula 3-37
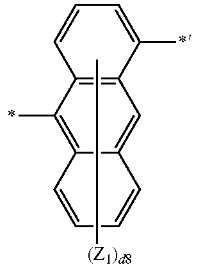
Formula 3-38
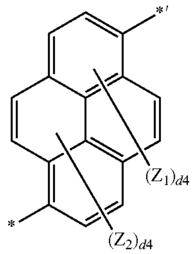
Formula 3-39
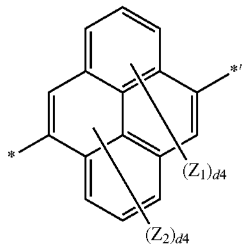

-continued

Formula 3-40

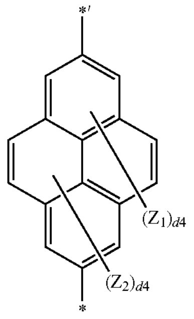

Formula 3-41

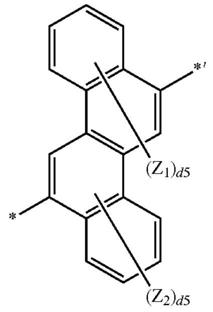

Formula 3-42

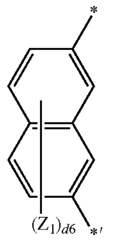

Formula 3-43

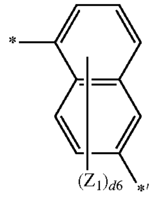

Formula 3-44

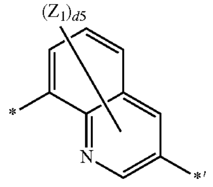

Formula 3-45

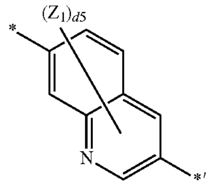

-continued

Formula 3-46

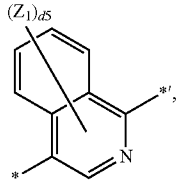

wherein, in Formulae 3-1 to 3-46, $Y_1$ is selected from O, S, $C(Z_3)(Z_4)$, $N(Z_5)$, and $Si(Z_6)(Z_7)$, $Z_1$ to $Z_7$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a benzoimidazolyl group, a phenanthrolinyl group, and $—Si(Q_{33})(Q_{34})(Q_{35})$, wherein $Q_{33}$ to $Q_{35}$ are each independently selected from a $C_1$-$C_{10}$ alkyl group, a $C_1$-$C_{10}$ alkoxy group, a phenyl group, a biphenyl group, a terphenyl group, and a naphthyl group, d2 is 1 or 2, d3 is an integer selected from 1 to 3, d4 is an integer selected from 1 to 4, d5 is an integer selected from 1 to 5, d6 is an integer selected from 1 to 6, d8 is an integer selected from 1 to 8, and

* and *' each indicate a binding site to a neighboring atom.

4. The condensed cyclic compound of claim 1, wherein $L_1$ is selected from groups represented by Formulae 4-1 to 4-45:

Formula 4-1

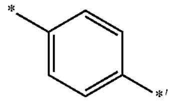

Formula 4-2

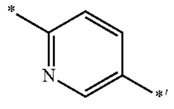

Formula 4-3

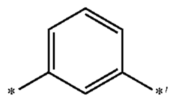

Formula 4-4

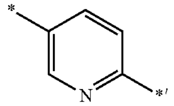

-continued
Formula 4-5
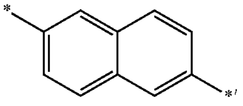
Formula 4-6
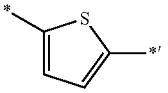
Formula 4-7
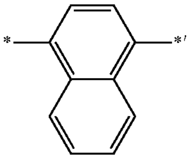
Formula 4-8
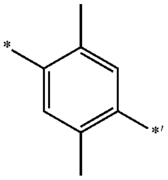
Formula 4-9
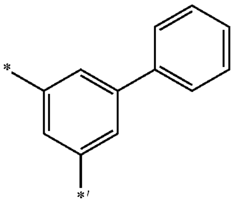
Formula 4-10
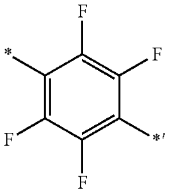
Formula 4-11
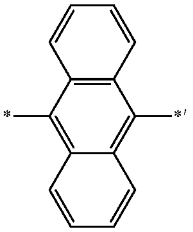
Formula 4-12
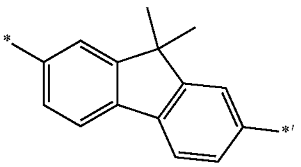
Formula 4-13
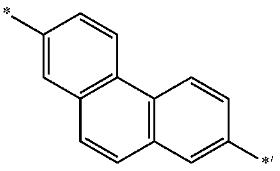
-continued
Formula 4-14
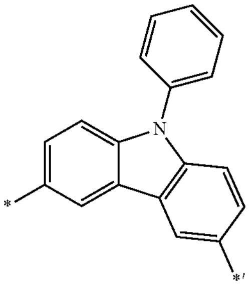
Formula 4-15
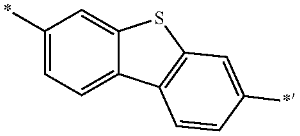
Formula 4-16
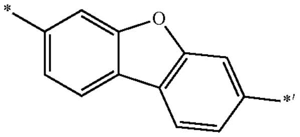
Formula 4-17
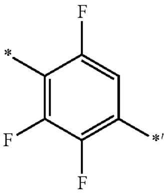
Formula 4-18
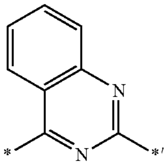
Formula 4-19
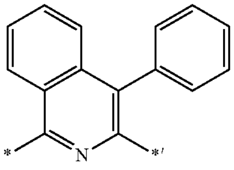
Formula 4-20
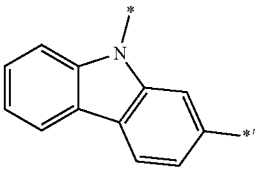
Formula 4-21
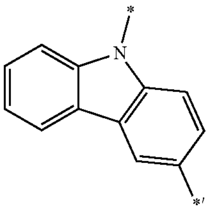

-continued
Formula 4-22
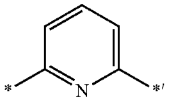
Formula 4-23
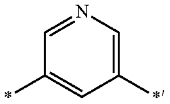
Formula 4-24
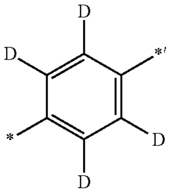
Formula 4-25
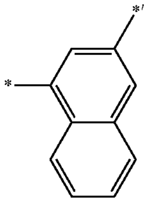
Formula 4-26
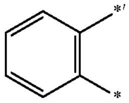
Formula 4-27
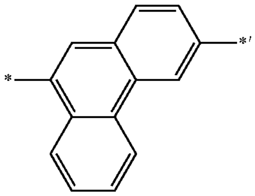
Formula 4-28
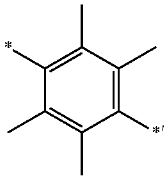
Formula 4-29
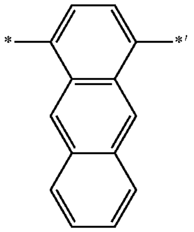
Formula 4-30
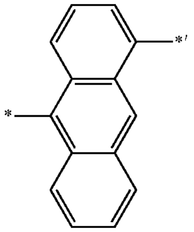
-continued
Formula 4-31
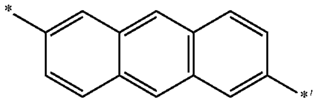
Formula 4-32
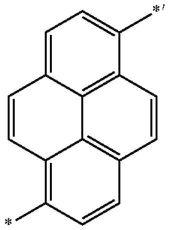
Formula 4-33
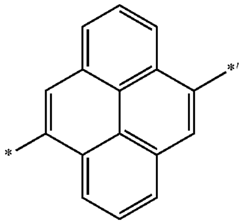
Formula 4-34
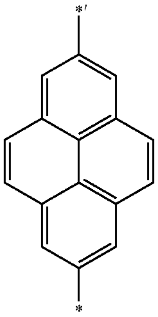
Formula 4-35
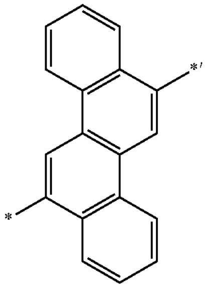
Formula 4-36
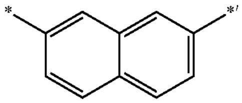
Formula 4-37
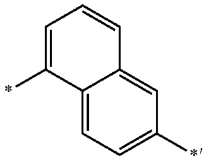

-continued

Formula 4-38

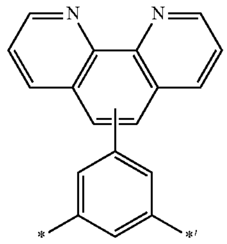

Formula 4-39

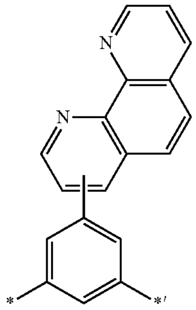

Formula 4-40

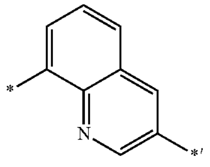

Formula 4-41

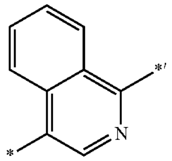

Formula 4-42

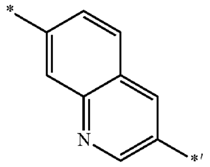

Formula 4-43

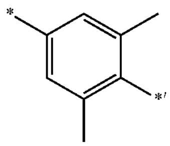

Formula 4-44

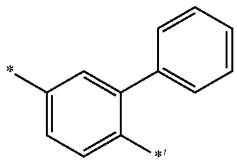

Formula 4-45

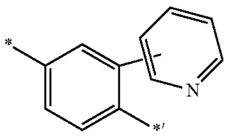

, wherein, in Formulae 4-1 to 4-45, * and *' each indicate a binding site to a neighboring atom.

5. The condensed cyclic compound of claim 1, wherein a1 is 0, 1, or 2.

6. The condensed cyclic compound of claim 1, wherein $A_1$ is selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{33}$)($Q_{34}$)($Q_{35}$), wherein $Q_{33}$ to $Q_{35}$ are each independently selected from a $C_1$-$C_{10}$ alkyl group, a $C_1$-$C_{10}$ alkoxy group, a phenyl group, a biphenyl group, a terphenyl group, and a naphthyl group.

7. The condensed cyclic compound of claim 1, wherein $A_1$ is selected from:

an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an oxadiazolyl group, a triazinyl group, an imidazopyridinyl group, and an imidazopyrimidinyl group; and an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an oxadiazolyl group, a triazinyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an oxadiazolyl group, a triazinyl group, an imidazopyridinyl group, an imidazopyrimidinyl group, and —Si($Q_{33}$)($Q_{34}$)($Q_{35}$), wherein $Q_{33}$ to $Q_{35}$ are each independently selected from a $C_1$-$C_{10}$ alkyl group, a $C_1$-$C_{10}$ alkoxy group, a phenyl group, a biphenyl group, a terphenyl group, and a naphthyl group.

8. The condensed cyclic compound of claim 1, wherein $A_1$ is selected from groups represented by Formulae 5-1 to 5-79:

Formula 5-1

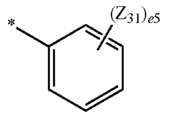

Formula 5-2

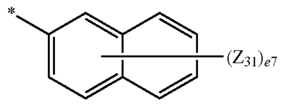

Formula 5-3

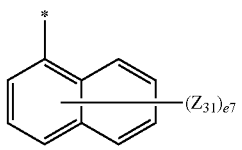

Formula 5-4

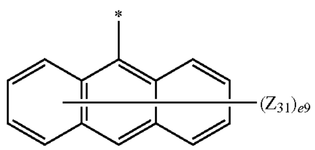

-continued
Formula 5-5
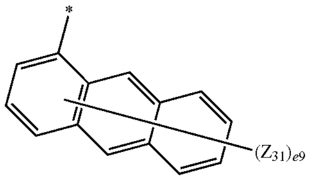
Formula 5-6
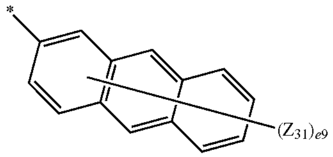
Formula 5-7
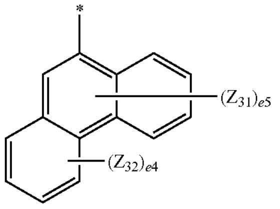
Formula 5-8
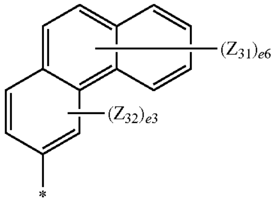
Formula 5-9
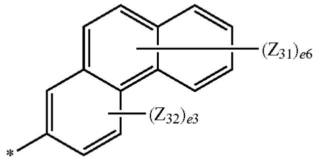
Formula 5-10
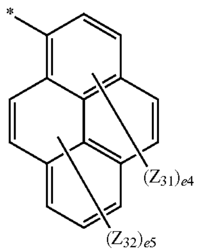
Formula 5-11
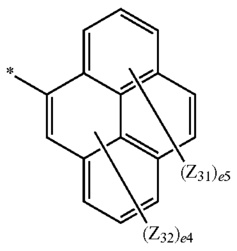
Formula 5-12
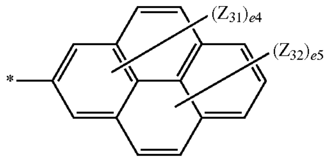
-continued
Formula 5-13
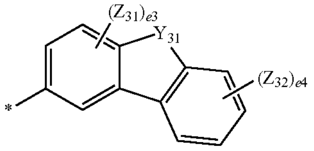
Formula 5-14
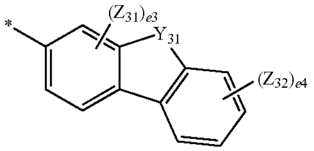
Formula 5-15
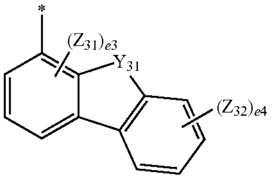
Formula 5-16
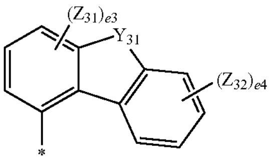
Formula 5-17
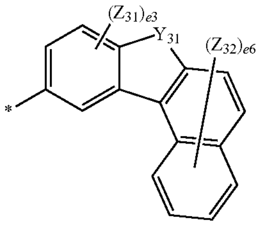
Formula 5-19
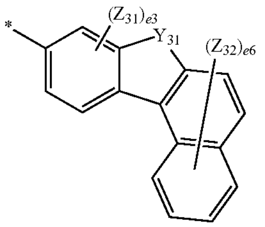
Formula 5-19
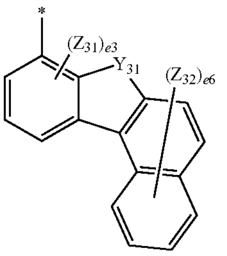
Formula 5-20
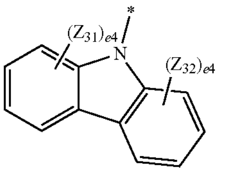

-continued
Formula 5-21
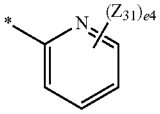
Formula 5-22
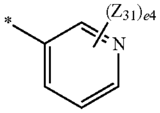
Formula 5-23
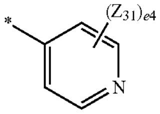
Formula 5-24
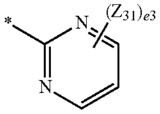
Formula 5-25
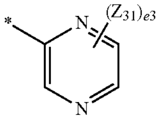
Formula 5-26
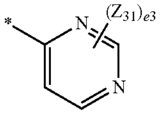
Formula 5-27
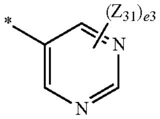
Formula 5-28
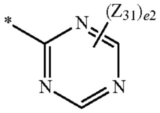
Formula 5-29
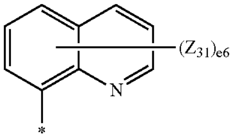
Formula 5-30
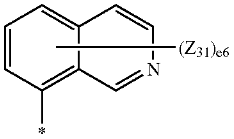
Formula 5-31
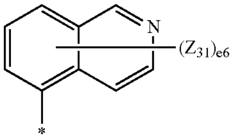
-continued
Formula 5-32
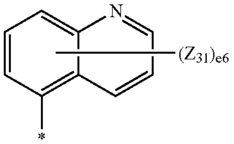
Formula 5-33
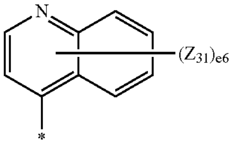
Formula 5-34
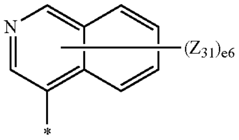
Formula 5-35
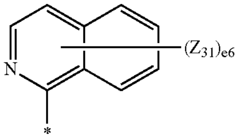
Formula 5-36
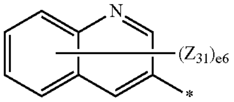
Formula 5-37
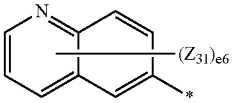
Formula 5-38
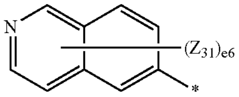
Formula 5-39
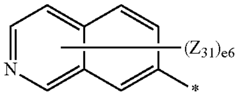
Formula 5-40
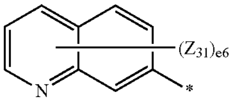
Formula 5-41
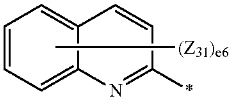
Formula 5-42
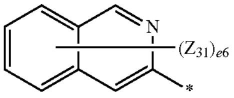
Formula 5-43
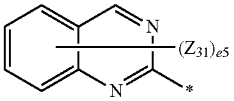

-continued
Formula 5-44
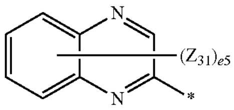
Formula 5-45
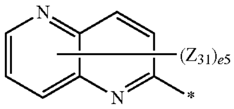
Formula 5-46
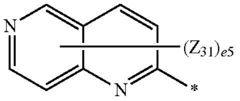
Formula 5-47
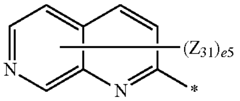
Formula 5-48
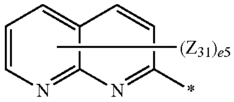
Formula 5-49
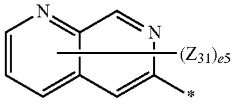
Formula 5-50
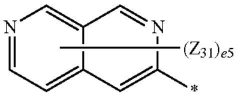
Formula 5-51
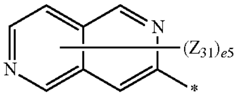
Formula 5-52
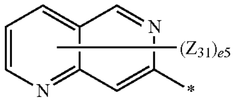
Formula 5-53
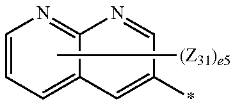
Formula 5-54
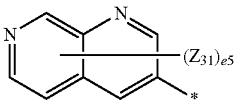
Formula 5-55
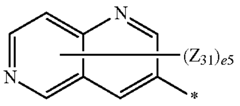
Formula 5-56
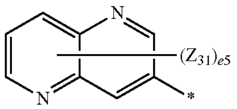
-continued
Formula 5-57
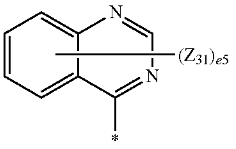
Formula 5-58
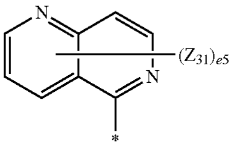
Formula 5-59
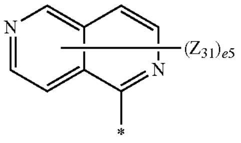
Formula 5-60
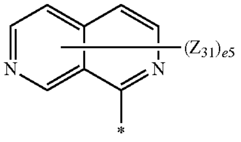
Formula 5-61
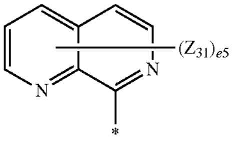
Formula 5-62
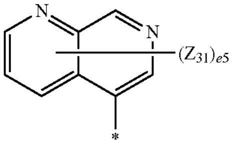
Formula 5-63
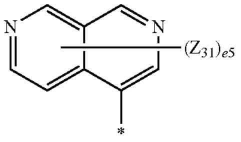
Formula 5-64
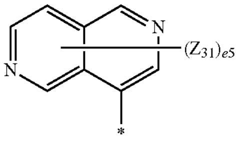
Formula 5-65
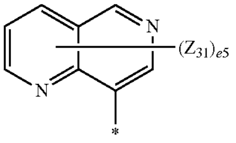
Formula 5-66
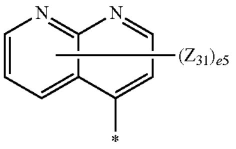

-continued

Formula 5-67

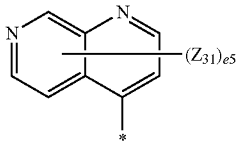

Formula 5-68

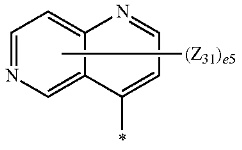

Formula 5-69

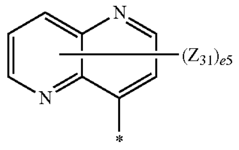

Formula 5-70

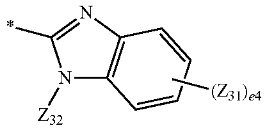

Formula 5-71

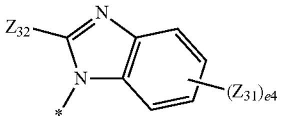

Formula 5-72

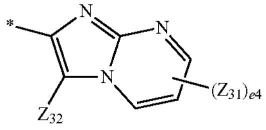

Formula 5-73

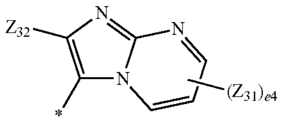

Formula 5-74

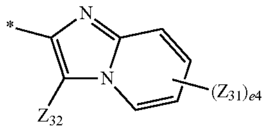

Formula 5-75

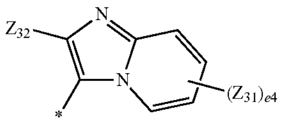

Formula 5-76

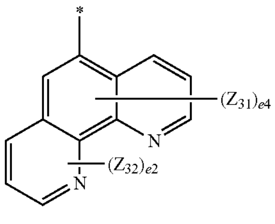

-continued

Formula 5-77

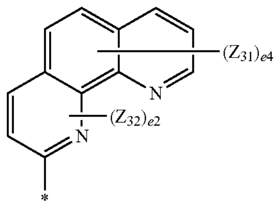

Formula 5-78

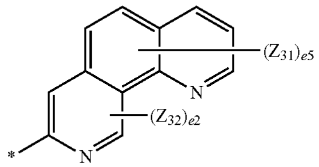

Formula 5-79

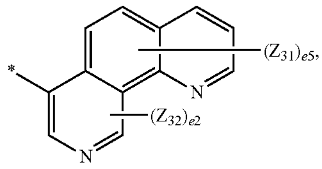

wherein, in Formulae 5-1 to 5-79, $Y_{31}$ is selected from O, S, $C(Z_{33})(Z_{34})$, $N(Z_{35})$, and $Si(Z_{36})(Z_{37})$, $Z_{31}$ to $Z_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a benzoimidazolyl group, a phenanthrolinyl group, a triazinyl group, and $—Si(Q_{33})(Q_{34})(Q_{35})$, wherein $Q_{33}$ to $Q_{35}$ are each independently selected from a $C_1$-$C_{10}$ alkyl group, a $C_1$-$C_{10}$ alkoxy group, a phenyl group, a biphenyl group, a terphenyl group, and a naphthyl group, e2 is 1 or 2, e3 is an integer selected from 1 to 3, e4 is an integer selected from 1 to 4, e5 is an integer selected from 1 to 5, e6 is an integer selected from 1 to 6, e7 is an integer selected from 1 to 7, e9 is an integer selected from 1 to 9, and

* indicates a binding site to a neighboring atom.

9. The condensed cyclic compound of claim 8, wherein $A_1$ is selected from groups represented by Formulae 5-21 to 5-79.

10. The condensed cyclic compound of claim 1, wherein $A_1$ is selected from groups represented by Formulae 6-1 to 6-43 and Formulae 10-1 to 10-121:

Formula 6-1
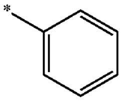
Formula 6-2
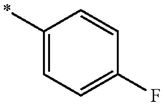
Formula 6-3
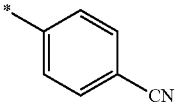
Formula 6-4
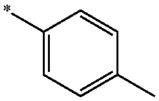
Formula 6-5
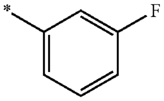
Formula 6-6
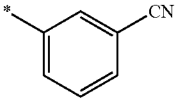
Formula 6-7
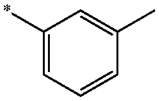
Formula 6-8
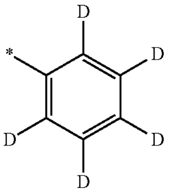
Formula 6-9
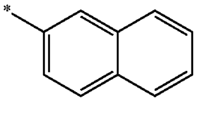
Formula 6-10
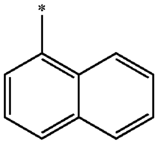
Formula 6-11
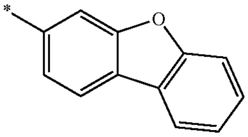
Formula 6-12
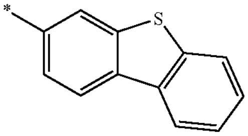
-continued
Formula 6-13
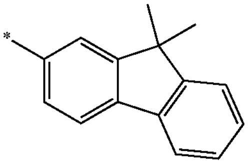
Formula 6-14
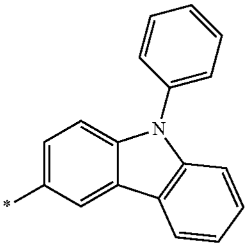
Formula 6-15
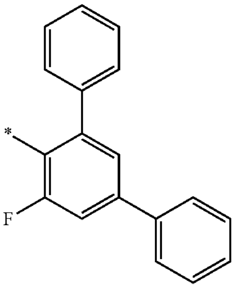
Formula 6-16
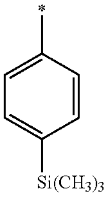
Formula 6-17
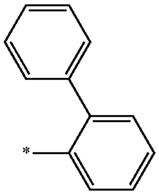
Formula 6-18
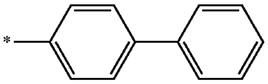
Formula 6-19
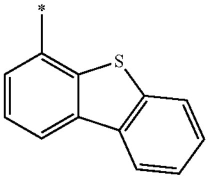
Formula 6-20
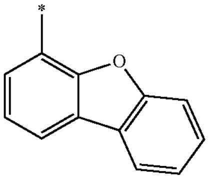

Formula 6-21
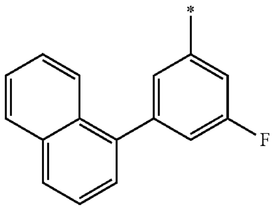
Formula 6-22
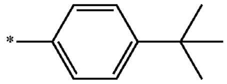
Formula 6-23
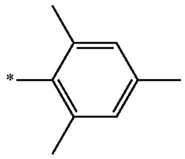
Formula 6-24
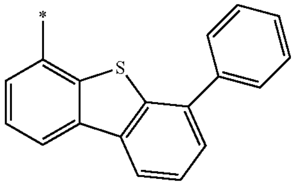
Formula 6-25
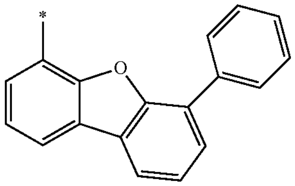
Formula 6-26
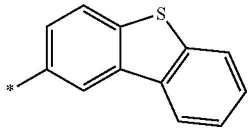
Formula 6-27
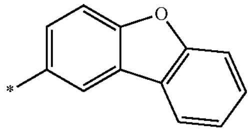
Formula 6-28
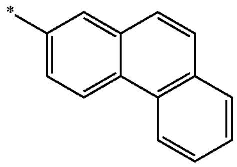
Formula 6-29
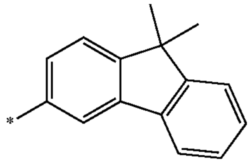
Formula 6-30
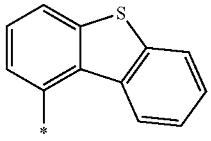
Formula 6-31
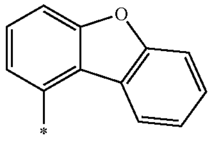
Formula 6-32
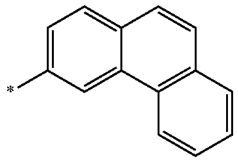
Formula 6-33
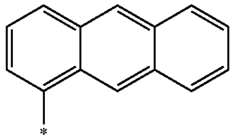
Formula 6-34
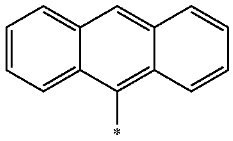
Formula 6-35
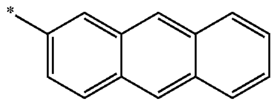
Formula 6-36
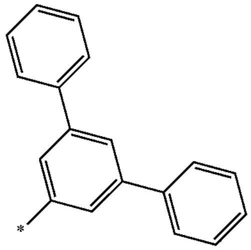
Formula 6-37
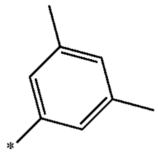
Formula 6-38
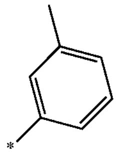
Formula 6-39
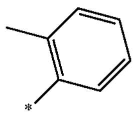

-continued
Formula 6-40
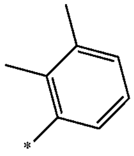
Formula 6-41
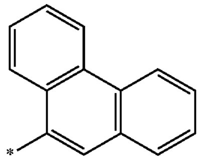
Formula 6-42
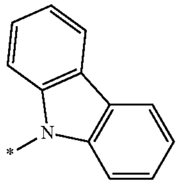
Formula 6-43
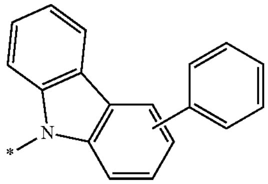
Formula 10-1
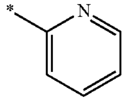
Formula 10-2
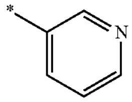
Formula 10-3
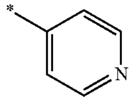
Formula 10-4
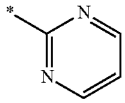
Formula 10-5
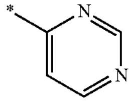
Formula 10-6
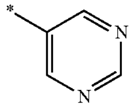
Formula 10-7
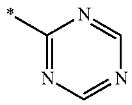
-continued
Formula 10-8
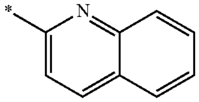
Formula 10-9
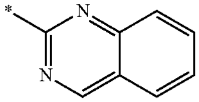
Formula 10-10
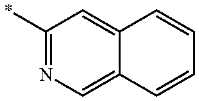
Formula 10-11
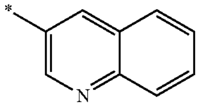
Formula 10-12
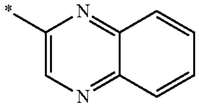
Formula 10-13
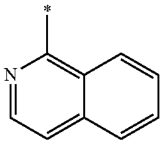
Formula 10-14
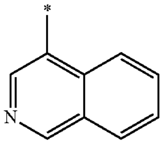
Formula 10-15
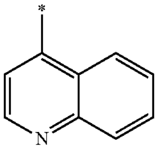
Formula 10-16
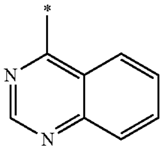
Formula 10-17
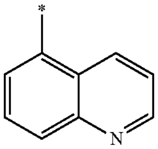
Formula 10-18
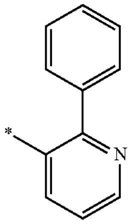

-continued
Formula 10-19
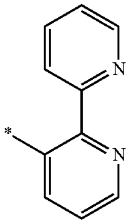
Formula 10-20
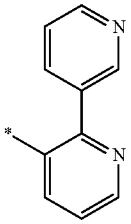
Formula 10-21
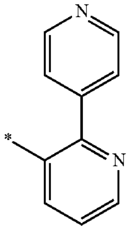
Formula 10-22
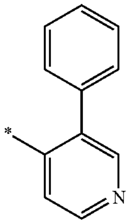
Formula 10-23
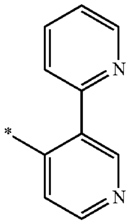
Formula 10-24
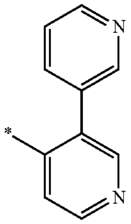
Formula 10-25
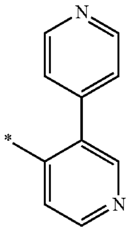
-continued
Formula 10-26
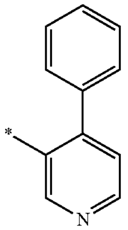
Formula 10-27
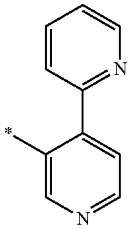
Formula 10-28
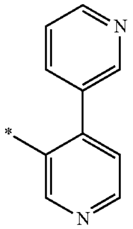
Formula 10-29
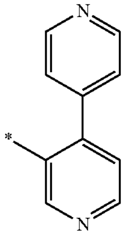
Formula 10-30
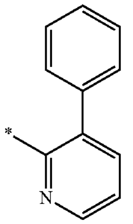
Formula 10-31
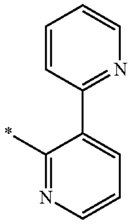

Formula 10-32
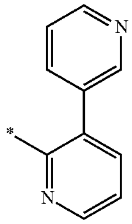
Formula 10-33
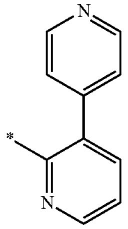
Formula 10-34
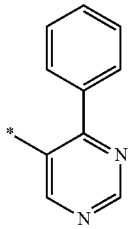
Formula 10-35
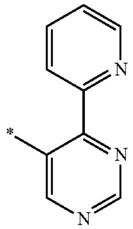
Formula 10-36
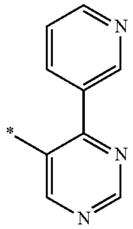
Formula 10-37
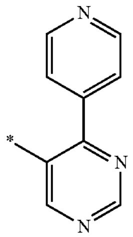
Formula 10-38
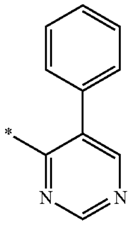
Formula 10-39
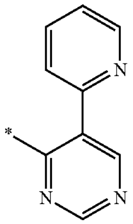
Formula 10-40
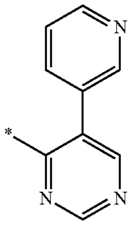
Formula 10-41
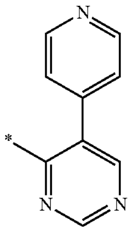
Formula 10-42
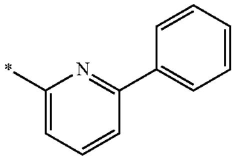
Formula 10-43
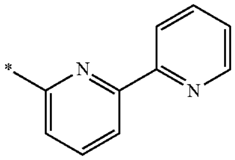
Formula 10-44
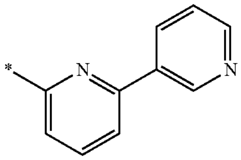
Formula 10-45
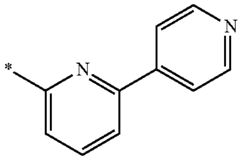

-continued
Formula 10-46
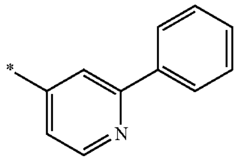
Formula 10-47
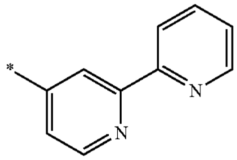
Formula 10-48
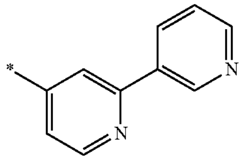
Formula 10-49
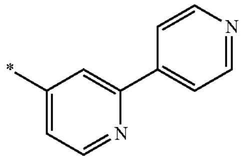
Formula 10-50
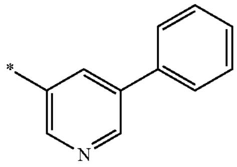
Formula 10-51
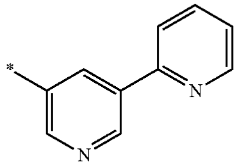
Formula 10-52
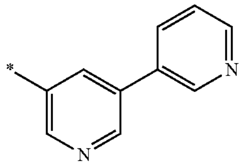
Formula 10-53
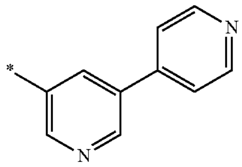
Formula 10-54
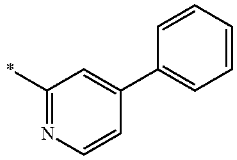
-continued
Formula 10-55
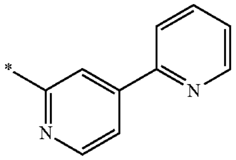
Formula 10-56
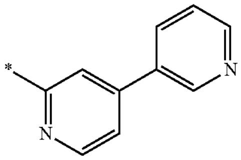
Formula 10-57
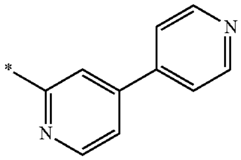
Formula 10-58
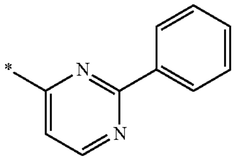
Formula 10-59
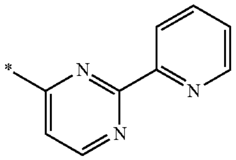
Formula 10-60
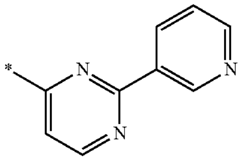
Formula 10-61
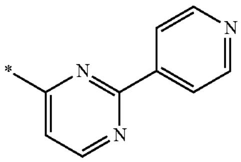
Formula 10-62
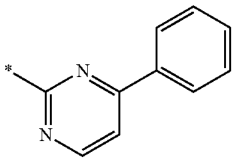
Formula 10-63
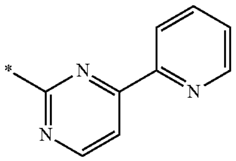

-continued
Formula 10-64
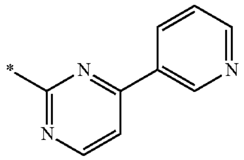
Formula 10-65
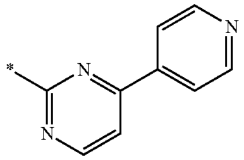
Formula 10-66
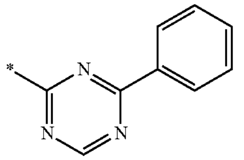
Formula 10-67
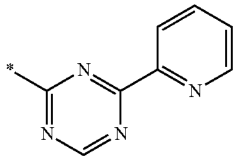
Formula 10-68
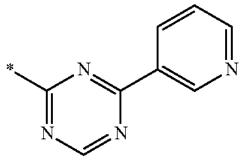
Formula 10-69
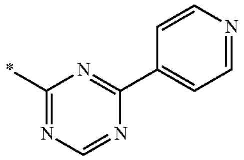
Formula 10-70
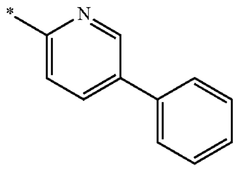
Formula 10-71
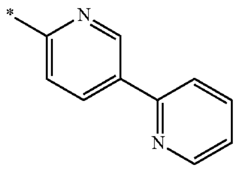
Formula 10-72
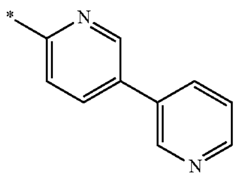
-continued
Formula 10-73
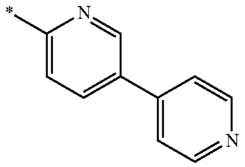
Formula 10-74
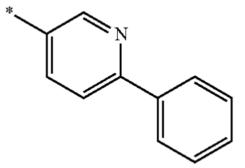
Formula 10-75
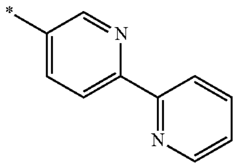
Formula 10-76
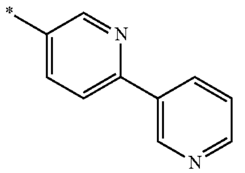
Formula 10-77
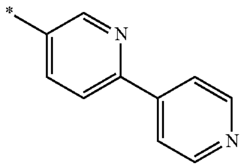
Formula 10-78
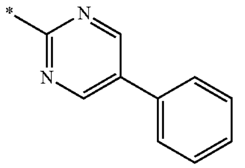
Formula 10-79
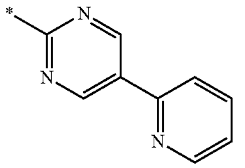
Formula 10-80
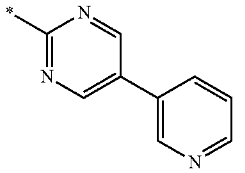
Formula 10-81
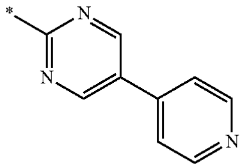

-continued
Formula 10-82
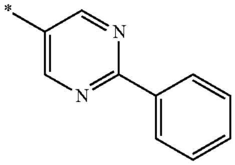
Formula 10-83
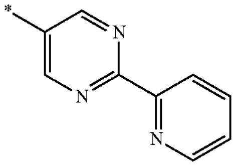
Formula 10-84
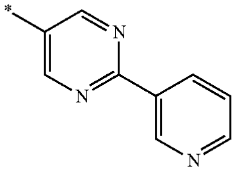
Formula 10-85
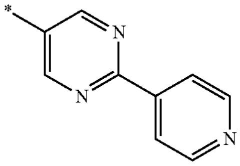
Formula 10-86
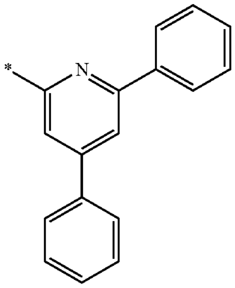
Formula 10-87
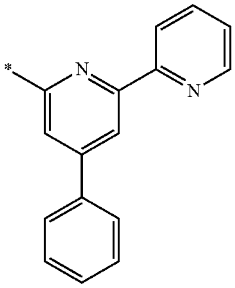
Formula 10-88
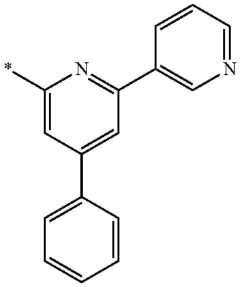
-continued
Formula 10-89
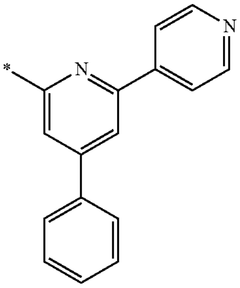
Formula 10-90
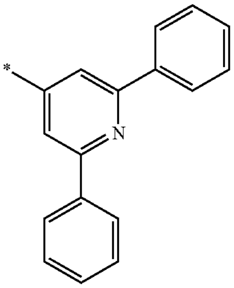
Formula 10-91
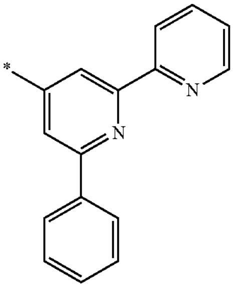
Formula 10-92
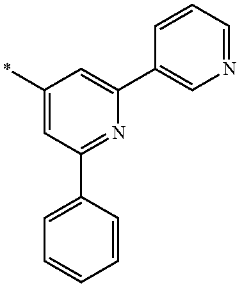
Formula 10-93
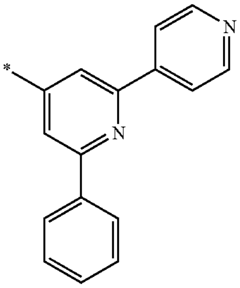

-continued
Formula 10-94
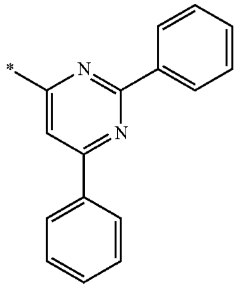
Formula 10-95
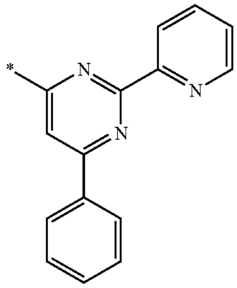
Formula 10-96
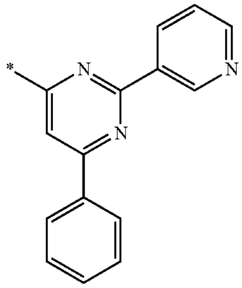
Formula 10-97
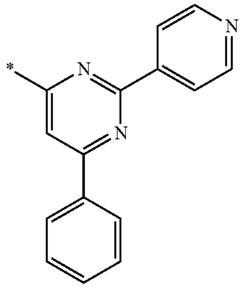
Formula 10-98
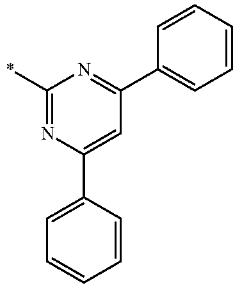
-continued
Formula 10-99
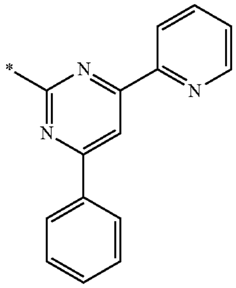
Formula 10-100
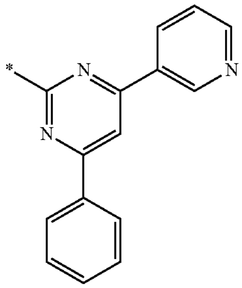
Formula 10-101
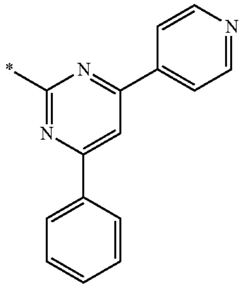
Formula 10-102
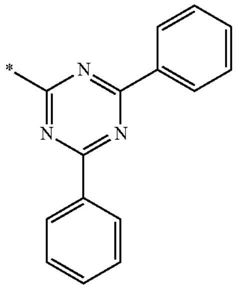
Formula 10-103
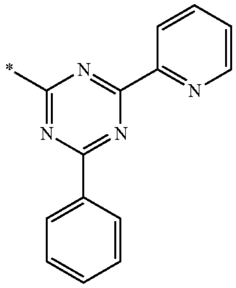

-continued
Formula 10-104
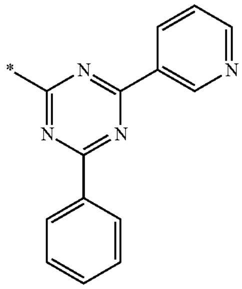
Formula 10-105
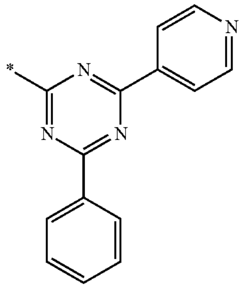
Formula 10-106
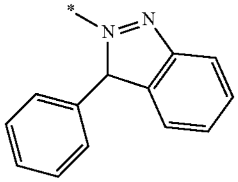
Formula 10-107
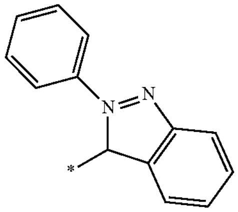
Formula 10-108
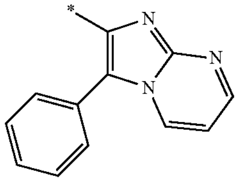
Formula 10-109
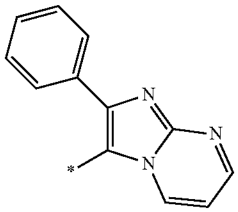
Formula 10-110
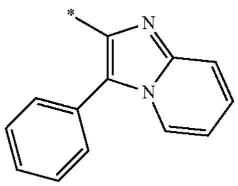
-continued
Formula 10-111
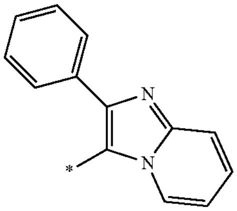
Formula 10-112
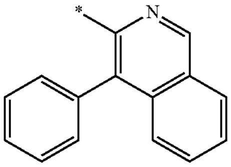
Formula 10-113
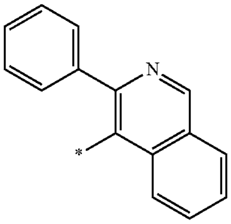
Formula 10-114
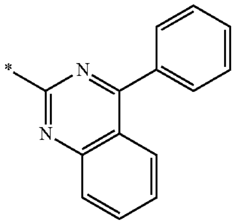
Formula 10-115
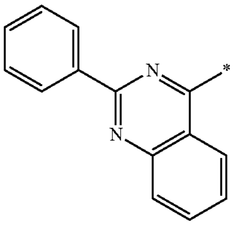
Formula 10-116
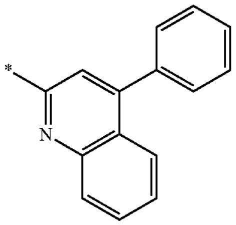
Formula 10-117
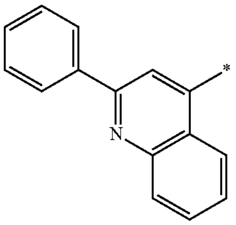

-continued

Formula 10-118

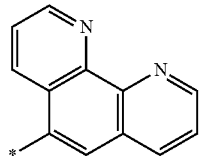

Formula 10-119

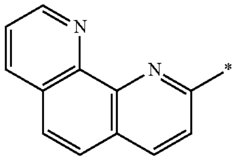

Formula 10-120

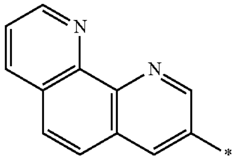

Formula 10-121

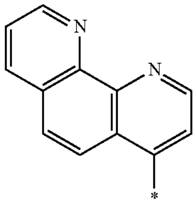

, wherein, in Formulae 6-1 to 6-43 and 10-1 to 10-121, * indicates a binding site to a neighboring atom.

11. The condensed cyclic compound of claim 1, wherein b1 is 1 or 2.

12. The condensed cyclic compound of claim 1, wherein $R_1$ to $R_{12}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, and —Si($Q_3$)($Q_4$)($Q_5$), wherein $Q_3$ to $Q_5$ are each independently selected from a $C_1$-$C_{10}$ alkyl group, a $C_1$-$C_{10}$ alkoxy group, a phenyl group, a biphenyl group, a terphenyl group, and a naphthyl group.

13. The condensed cyclic compound of claim 12, wherein $L_1$ is selected from:

a phenylene group, a naphthylene group, a phenanthrenylene group, an anthracenylene group, a fluoranthenylene group, a triphenylenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a phenanthrolinylene group, a triazinylene group, a benzoimidazolylene group, an imidazopyridinylene group, and an imidazopyrimidinylene group; and a phenylene group, a naphthylene group, a phenanthrenylene group, an anthracenylene group, a fluoranthenylene group, a triphenylenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a phenanthrolinylene group, a triazinylene group, a benzoimidazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a phenanthrolinyl group, a triazinyl group, a benzoimidazolyl group, an imidazopyridinyl group, an imidazopyrimidinyl group, and —Si($Q_{33}$)($Q_{34}$)($Q_{35}$), a1 is 0, 1, or 2, $A_1$ is selected from:

a phenyl group, a biphenyl group, a terphenyl group, a naphthyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a phenanthrolinyl group, a triazinyl group, a benzoimidazolyl group, an imidazopyridinyl group, and an imidazopyrimidinyl group; and a phenyl group, a biphenyl group, a terphenyl group, a naphthyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a phenanthrolinyl group, a triazinyl group, a benzoimidazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a phenanthrolinyl group, a triazinyl group, a benzoimidazolyl group, an imidazopyridinyl group, an imidazopyrimidinyl group, and —Si($Q_{33}$)($Q_{34}$)($Q_{35}$), and b1 is 1 or 2, wherein $Q_{33}$ to $Q_{35}$ are each independently selected from a $C_1$-$C_{10}$ alkyl group, a $C_1$-$C_{10}$ alkoxy group, a phenyl group, a biphenyl group, a terphenyl group, and a naphthyl group.

14. The condensed cyclic compound of claim 1, wherein the condensed cyclic compound is selected from Compounds 1 to 56:

-continued
1
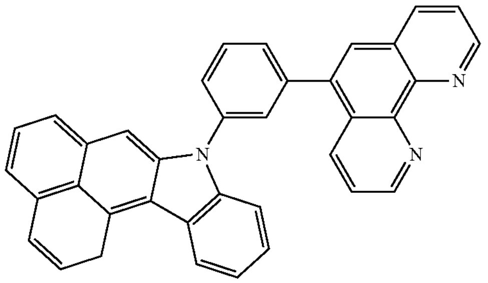
2
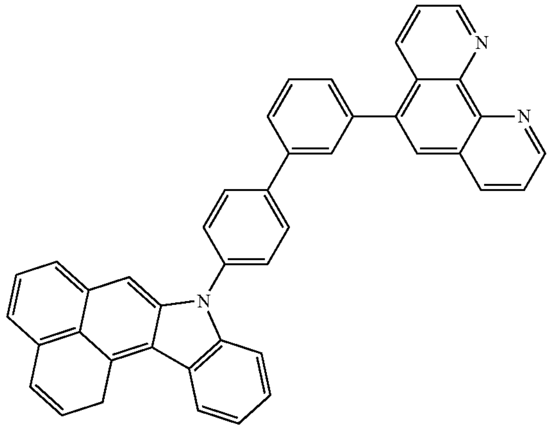
3
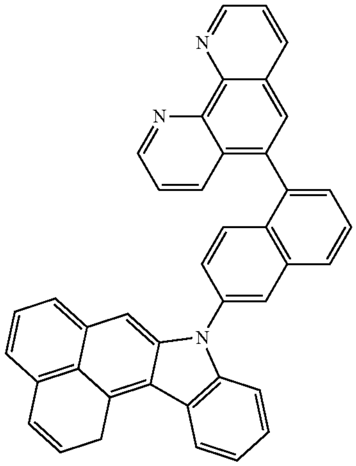
4
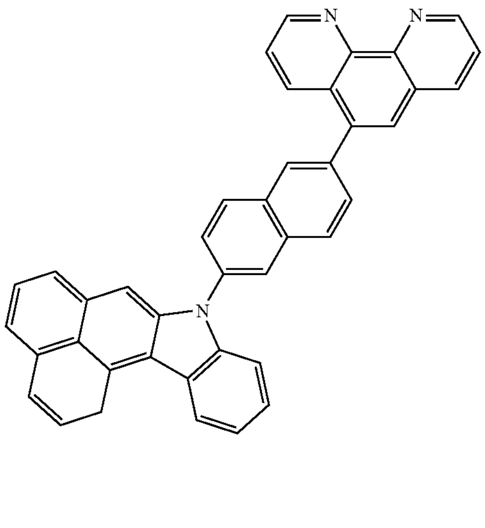
5
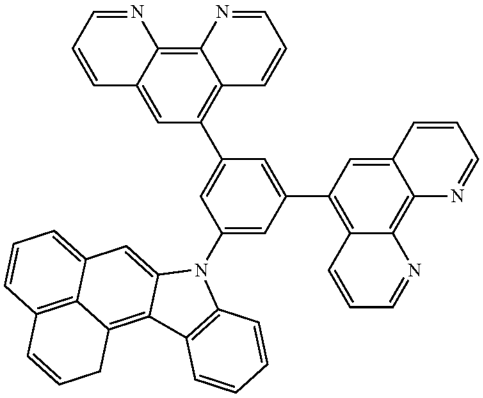
6
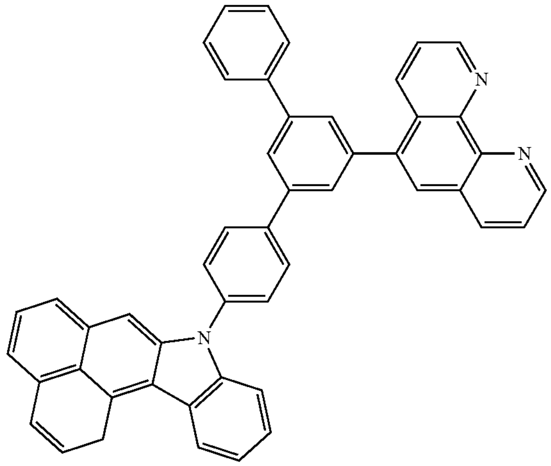
7
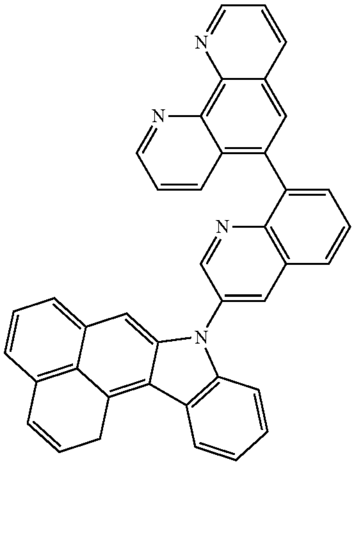

-continued
8
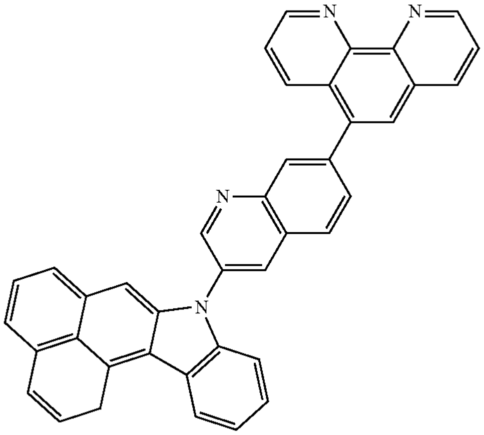
9
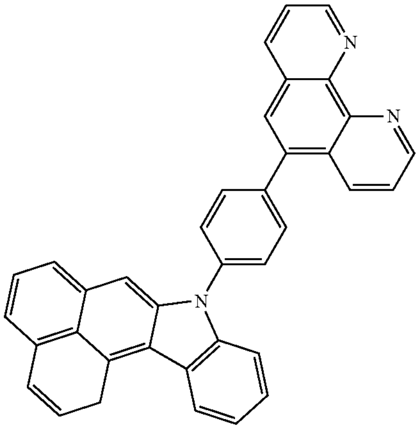
10
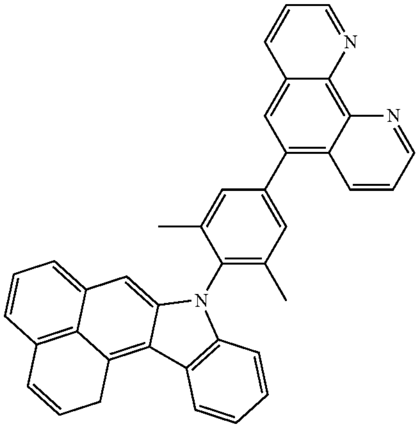
-continued
11
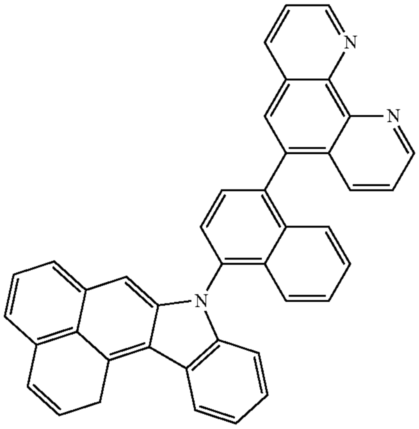
12
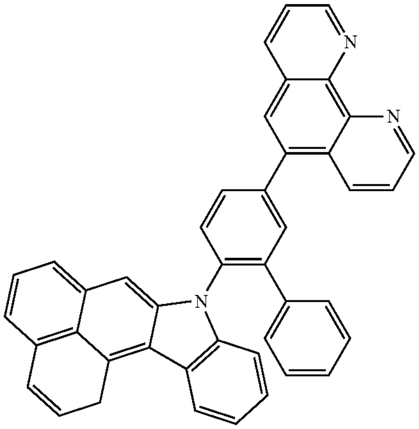
13
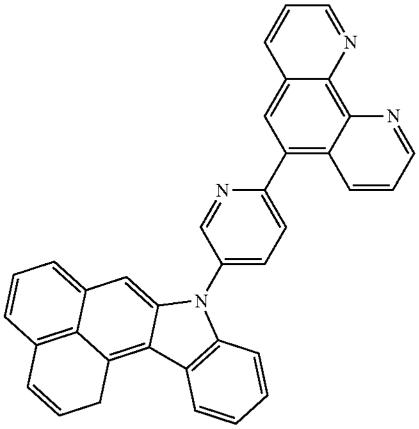

-continued
14
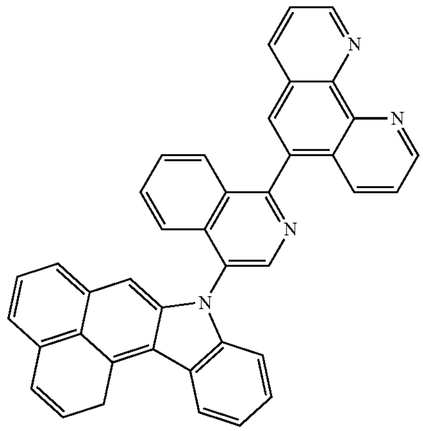
15
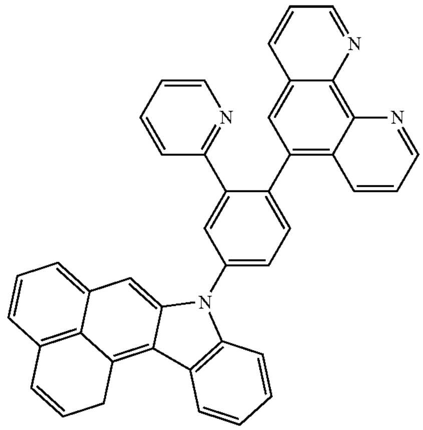
16
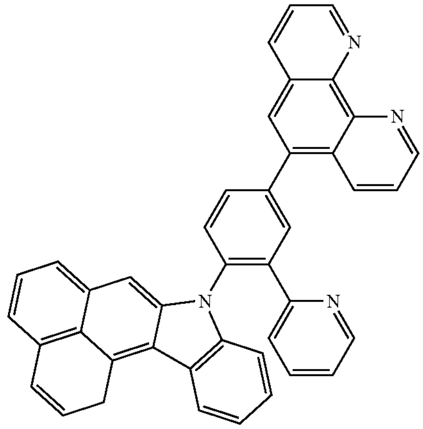
17
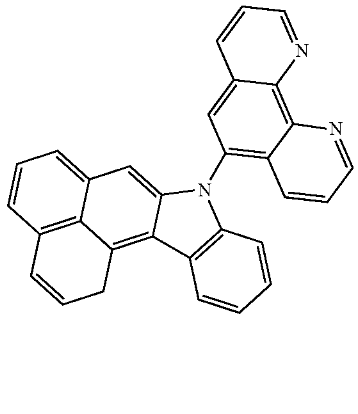
-continued
18
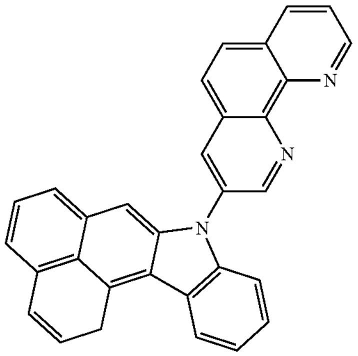
19
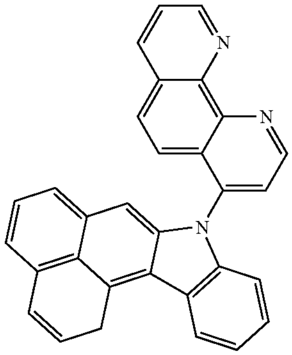
20
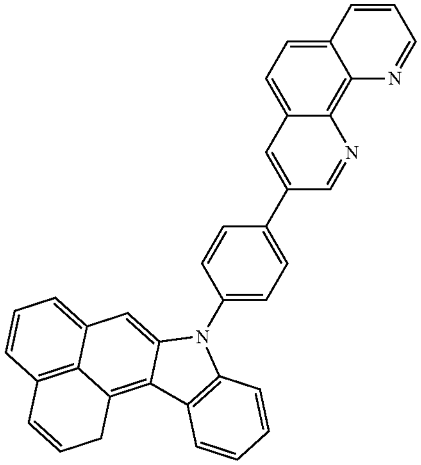
21
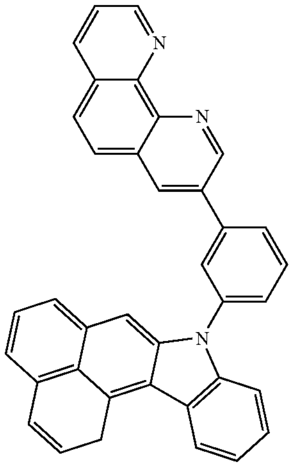

-continued
22
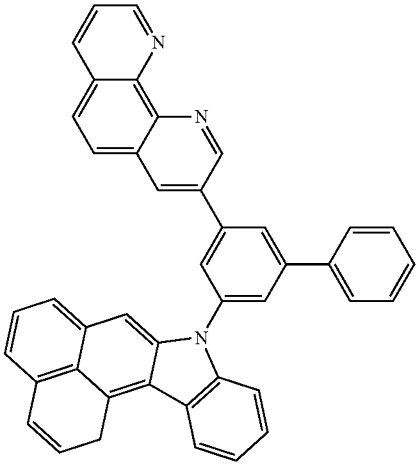
25
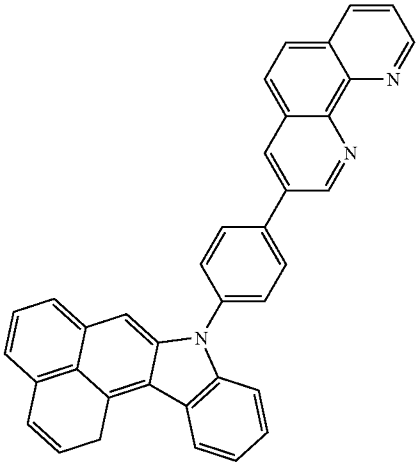
23
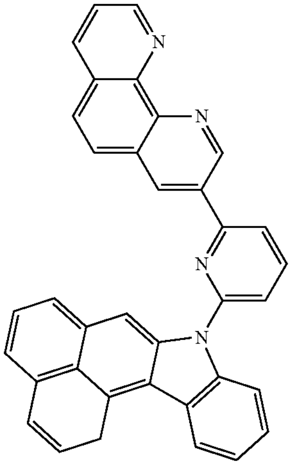
26
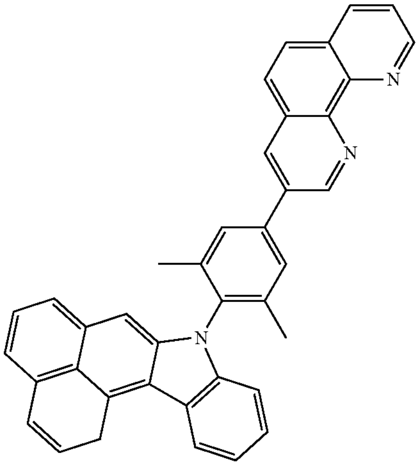
24
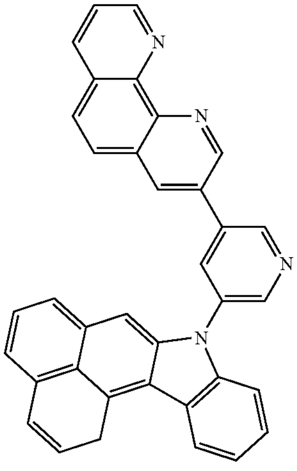
27
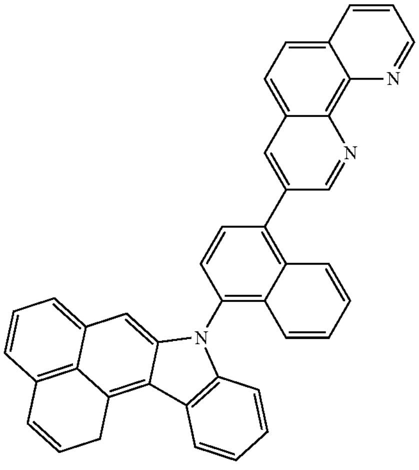

-continued
28
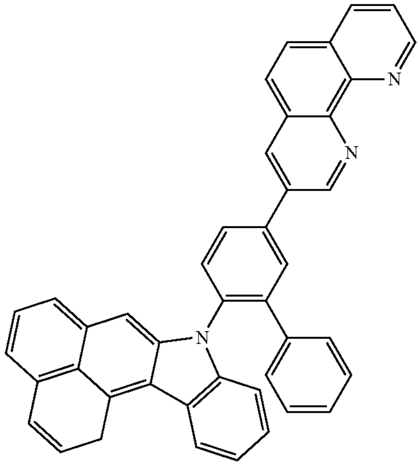
29
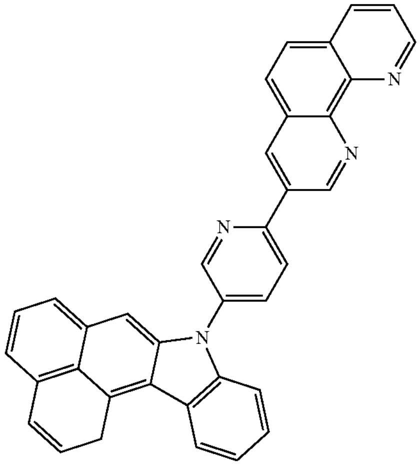
30
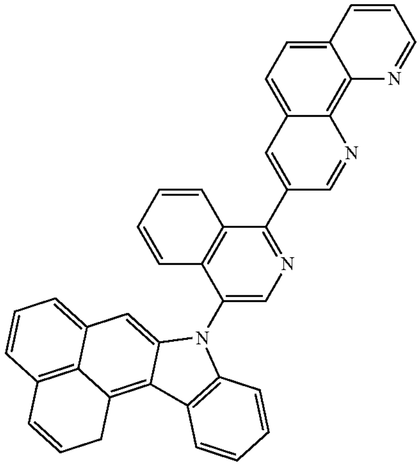
-continued
31
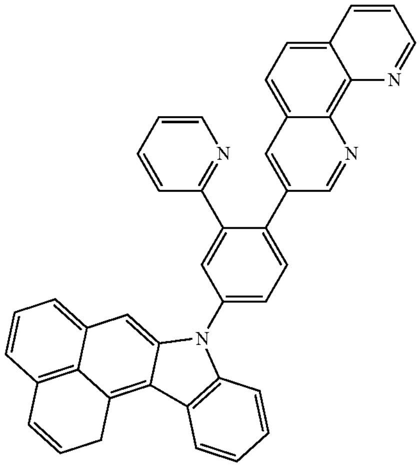
32
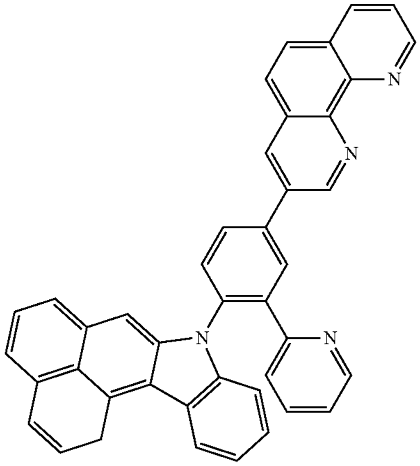
33
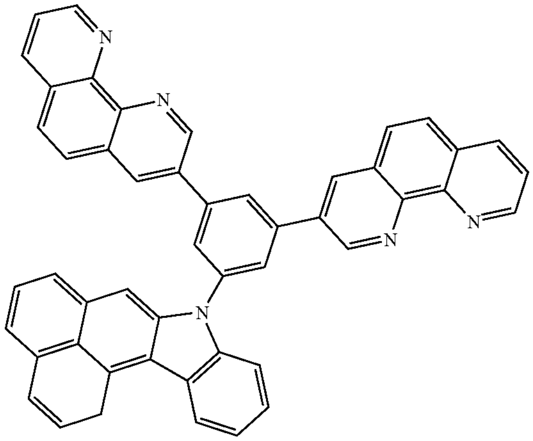

-continued
34
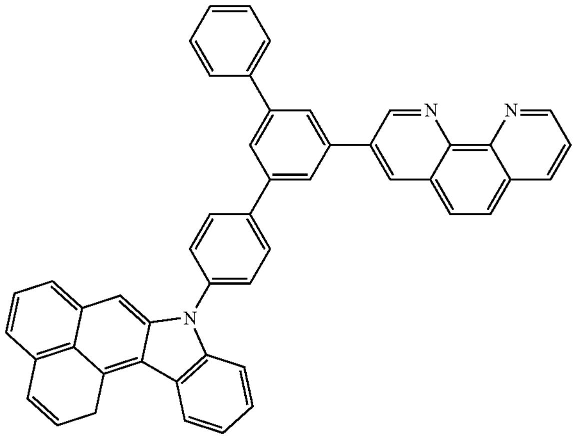
35
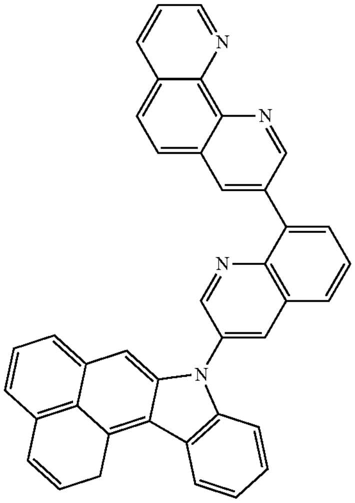
36
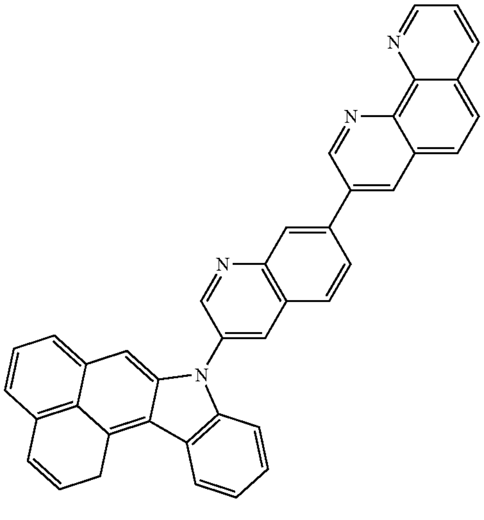
-continued
37
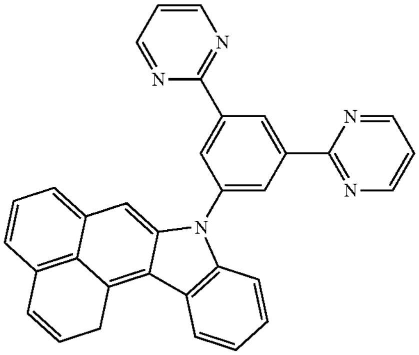
38
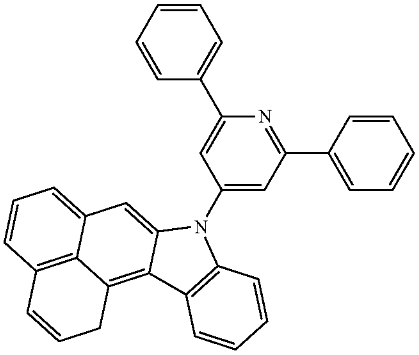
39
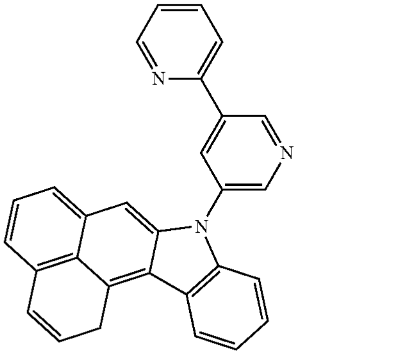
40
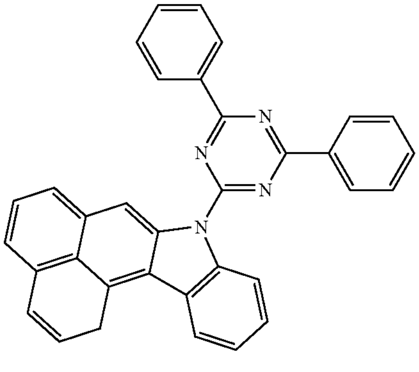

-continued
41
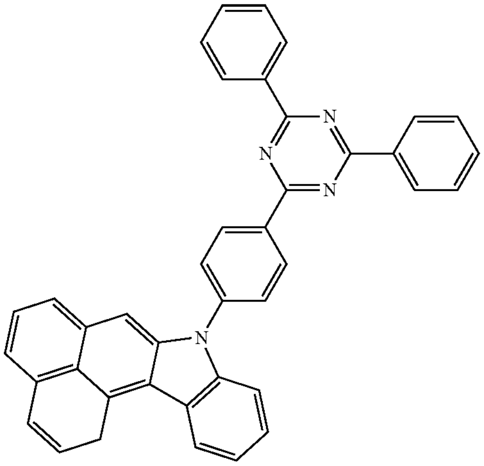
42
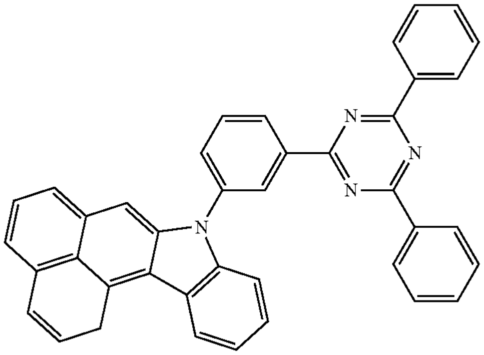
43
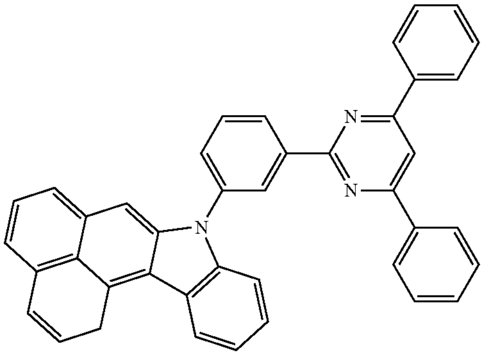
44
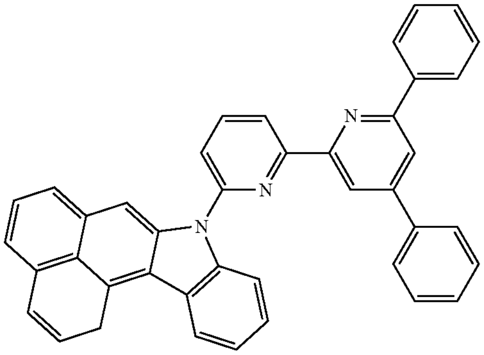
-continued
45
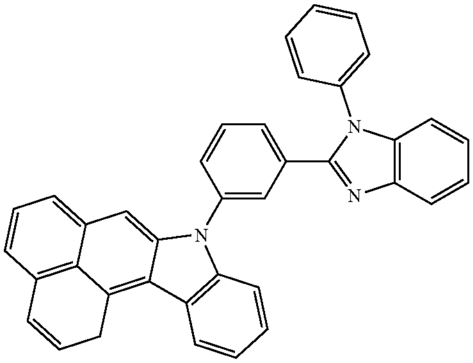
46
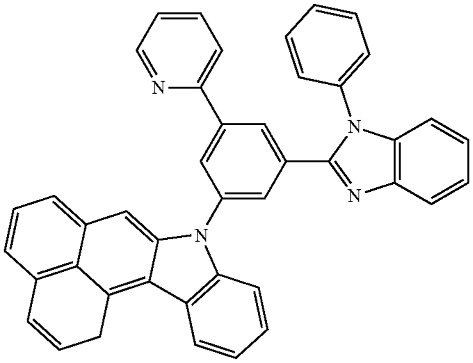
47
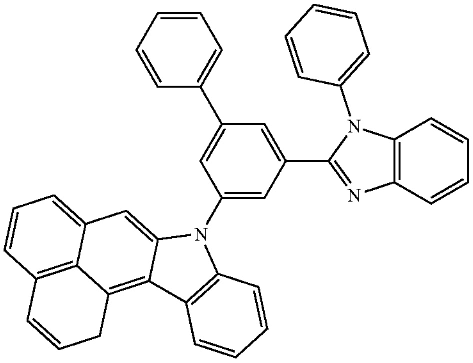
48
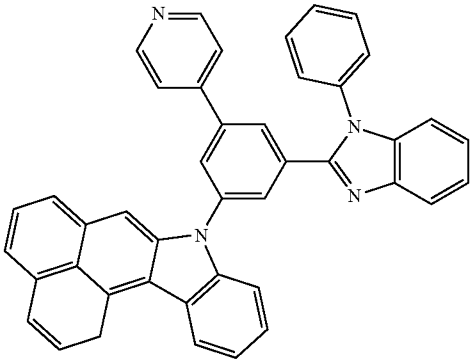

-continued
49
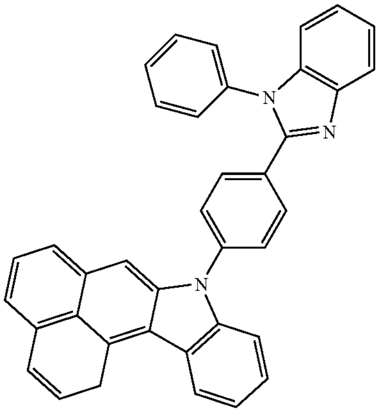
50
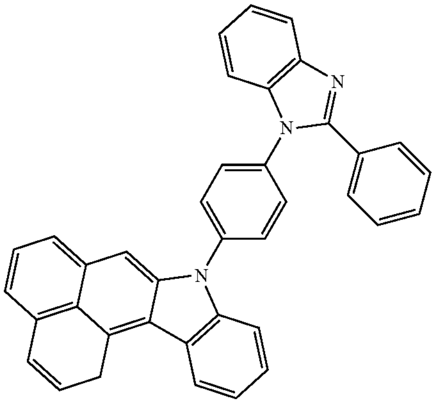
51
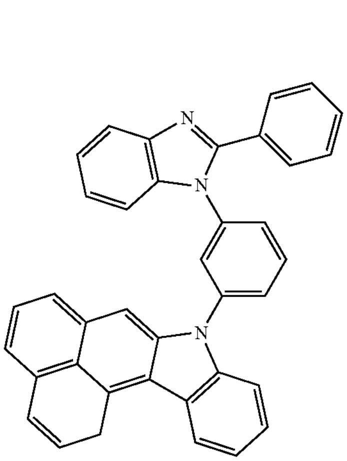
-continued
52
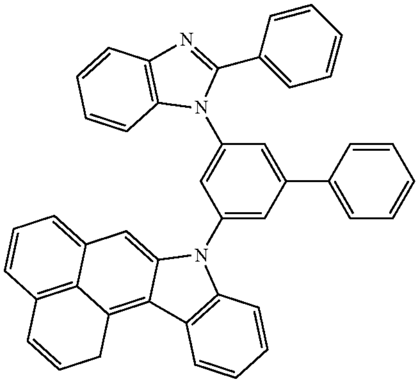
53
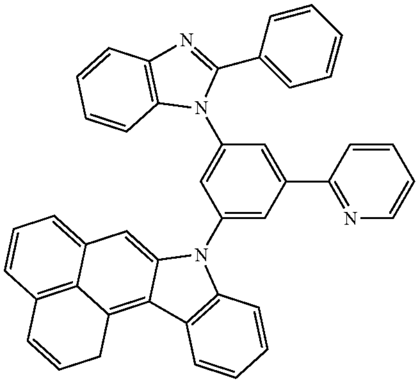
54
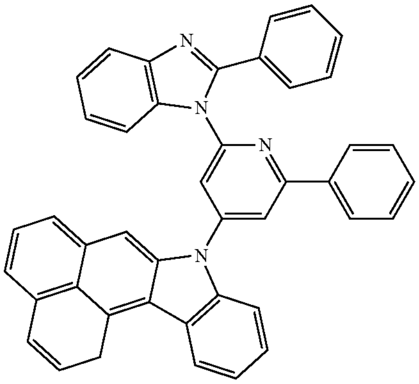
55
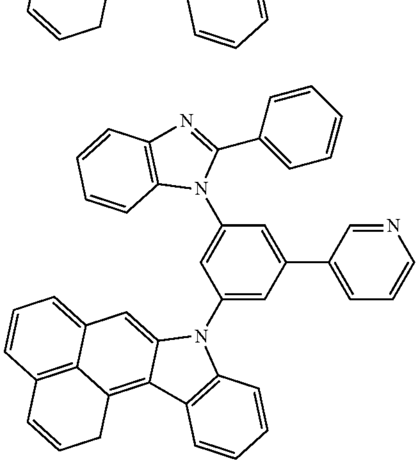

-continued

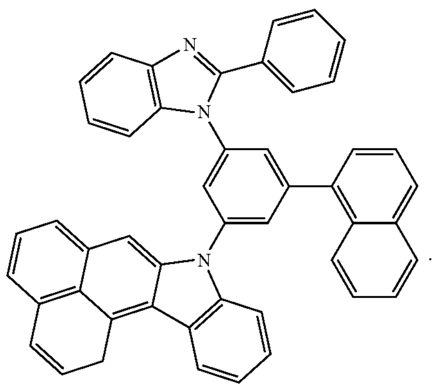

56

15. An organic light-emitting device comprising:

a first electrode;

a second electrode facing the first electrode; and an organic layer between the first electrode and the second electrode, the organic layer comprising an emission layer;

wherein the organic layer comprises the condensed cyclic compound of claim 1.

16. The organic light-emitting device of claim 15, wherein
the first electrode is an anode,
the second electrode is a cathode, and
the organic layer comprises a hole transport region between the first electrode and the emission layer, and an electron transport region between the emission layer and the second electrode,
wherein the hole transport region comprises at least one selected from a hole injection layer, a hole transport layer, a buffer layer, and an electron blocking layer; and the electron transport region comprises at least one selected from a hole blocking layer, an electron transport layer, and an electron injection layer.

17. The organic light-emitting device of claim 16, wherein at least one selected from the emission layer and the electron transport region comprises the condensed cyclic compound.

18. The organic light-emitting device of claim 16, wherein the electron transport region comprises the electron transport layer, and the electron transport layer comprises the condensed cyclic compound.

19. The organic light-emitting device of claim 17, wherein the emission layer comprises the condensed cyclic compound.

20. The organic light-emitting device of claim 19, wherein the emission layer further comprises a dopant, and wherein an amount of the condensed cyclic compound in the emission layer is greater than an amount of the dopant in the emission layer.

* * * * *